(12) United States Patent
Yamaguchi et al.

(10) Patent No.: US 9,957,516 B2
(45) Date of Patent: May 1, 2018

(54) METHOD FOR MODULATING EXPRESSION OF SPECIFIC PROTEIN USING SPECIFIC TRANSCRIPTION FACTOR, ISOPRENOID-PRODUCING PLANT HAVING TRANSGENE ENCODING SPECIFIC TRANSCRIPTION FACTOR, AND METHOD FOR PRODUCING POLYISOPRENOID USING ISOPRENOID-PRODUCING PLANT

(71) Applicant: SUMITOMO RUBBER INDUSTRIES, LTD., Kobe-shi, Hyogo (JP)

(72) Inventors: Haruhiko Yamaguchi, Kobe (JP); Yukino Inoue, Kobe (JP); Satoshi Kuroda, Kobe (JP)

(73) Assignee: SUMITOMO RUBBER INDUSTRIES, LTD., Kobe-Shi, Hyogo (JP)

( * ) Notice: Subject to any disclaimer, the term of this patent is extended or adjusted under 35 U.S.C. 154(b) by 108 days.

(21) Appl. No.: 14/758,166

(22) PCT Filed: Jan. 9, 2014

(86) PCT No.: PCT/JP2014/050176
§ 371 (c)(1),
(2) Date: Jun. 26, 2015

(87) PCT Pub. No.: WO2014/109342
PCT Pub. Date: Jul. 17, 2014

(65) Prior Publication Data
US 2016/0083739 A1 Mar. 24, 2016

(30) Foreign Application Priority Data

Jan. 10, 2013 (JP) .................................. 2013-002918
Mar. 5, 2013 (JP) .................................. 2013-043212
Mar. 5, 2013 (JP) .................................. 2013-043213

(51) Int. Cl.
*C12N 15/82* (2006.01)
*C12N 9/04* (2006.01)
*C07K 14/415* (2006.01)
*C12P 5/00* (2006.01)

(52) U.S. Cl.
CPC ........ *C12N 15/8216* (2013.01); *C07K 14/415* (2013.01); *C12N 9/0006* (2013.01); *C12N 15/8243* (2013.01); *C12P 5/007* (2013.01); *C12Y 101/01034* (2013.01)

(58) Field of Classification Search
None
See application file for complete search history.

(56) References Cited

PUBLICATIONS

Wei et al., 2010, Plant Physiology 153: 1031-1045, with supplemental data.*
Skirycz et al., 2007, New Phytologist 175: 425-438.*
Yang et al., 2012, Journal of Integrative Plant Biology 54: 703-712.*
Yanagisawa, 2002, Trends in Plant Science 7: 555-560.*
*Arabidopsis thaliana* OBF binding protein (OBP4), GenBank, published Sep. 30, 2016.*
Zhang et al., 2016, Frontiers in Plant Science, Article 1360, pp. 1-9.*
Abe et al., "*Arabidopsis* AtMYC2 (bHLH) and AtMYB2 (MYB) Function as Transcriptional Activators in Abscisic Acid Signaling," The Plant Cell, vol. 15, Jan. 2003 (published online Dec. 19, 2002), pp. 63-78.
De Nigris et al., "New insights in the transcriptional activity and coregulator molecules in the arterial wall," International Journal of Cardiology, vol. 86, 2002, pp. 153-168.
Gardiner et al., "Expression of DOF genes identifies early stages of vascular development in *Arabidopsis* leaves," The International Journal of Developmental Biology, vol. 54, 2010, pp. 1389-1396.
Hao et al., "Laticifer Differentiation in Hevea brasiliensis: Induction by Exogenous Jasmonic Acid and Linolenic Acid," Annals of Botany, vol. 85, 2000, pp. 37-43.
Imaizumi et al., "FKF1 F-Box Protein Mediates Cyclic Degradation of a Repressor of CONSTANS in *Arabidopsis*," Science, vol. 309, Jul. 8, 2005, pp. 293-297.
Mahjoub et al., "Overexpression of a grapevine R2R3-MYB factor in tomato affects vegetative development, flower morphology and flavonoid and terpenoid metabolism," Plant Physiology and Biochemistry, vol. 47, 2009 (available online Mar. 10, 2009), pp. 551-561.
Mayer et al., "*Arabidopsis thaliana* transcription repressor MYB6 (MYB6) mRNA, complete cds," NCBI Reference Sequence NM_117014.2, May 28, 2011, 2 pages.
Sano et al., "Over-expression of transcription associated factor genes co-expressed with genes of the mevalonate pathway, upstream of isoprenoid biosynthesis, in *Arabidopsis* cultured cells," Plant Biotechnology, vol. 25, 2008, pp. 583-587.
Shimano et al., "Overproduction of Cholesterol and Fatty Acids Causes Massive Liver Enlargement in Transgenic Mice Expressing Truncated SREBP-1a," The Journal of Clinical Investigation, vol. 98, No. 7, Oct. 1996, pp. 1575-1584.

(Continued)

*Primary Examiner* — Amjad Abraham
*Assistant Examiner* — Bratislav Stankovic
(74) *Attorney, Agent, or Firm* — Birch, Stewart, Kolasch & Birch, LLP

(57) ABSTRACT

The present invention provides methods for enhancing the polyisoprenoid biosynthesis pathway. The present invention further provides isoprenoid-producing plants having an enhanced polyisoprenoid biosynthesis pathway, and methods for producing a polyisoprenoid using such an isoprenoid-producing plant. The present invention relates to methods for regulating the expression of specific protein(s) by a specific transcription factor; isoprenoid-producing plants into which has been introduced a gene encoding a specific transcription factor; and methods for producing a polyisoprenoid using such an isoprenoid-producing plant.

2 Claims, 1 Drawing Sheet

(56) References Cited

PUBLICATIONS

Swarbreck et al., "*Arabidopsis thaliana* transcription factor ILR3 (ILR3) mRNA, complete cds," NCBI Reference Sequence: NM_124849.3, May 28, 2011, 2 pages.

Theologis et al., "*Arabidopsis thalian* early-phytochrome-responsive1 (EPR1) mRNA, complete cds," NCBI Reference Sequence: NM_001123832.1, May 28, 2011, 2 pages.

Theologis et al., "*Arabidopsis thaliana* transcription factor EGL1 (EGL3) mRNA, complete cds," NCBI Reference Sequence: NM_001198373.1, May 26, 2011, 2 pages.

Theologis et al., "*Arabidopsis thaliana* transcription factor HFR1 (HFR1) mRNA, complete cds," NCBI Reference Sequence: NM_100115.2, May 28, 2011, 2 pages.

Theologis et al., "*Arabidopsis thaliana* transcription factor MYB3 (MYB3) mRNA, complete cds," NCBI Reference Sequence: NM_102111.3, May 28, 2011, 2 pages.

Wei et al., "Overexpression of AtDOF4.7, an *Arabidopsis* DOF Family Transcription Factor, Induces Floral Organ Abscission Deficiency in *Arabidopsis*," Plant Physiology, vol. 153, Jul. 2010, pp. 1031-1045.

Yang et al., "Overexpression of a Mutant Basic Helix-Loop-Helix Protein HFR1, HFR1-ΔN105, Activates a Branch Pathway of Light Signaling in *Arabidopsis*," Plant Physiology, vol. 133, 2003, pp. 1630-1642.

* cited by examiner

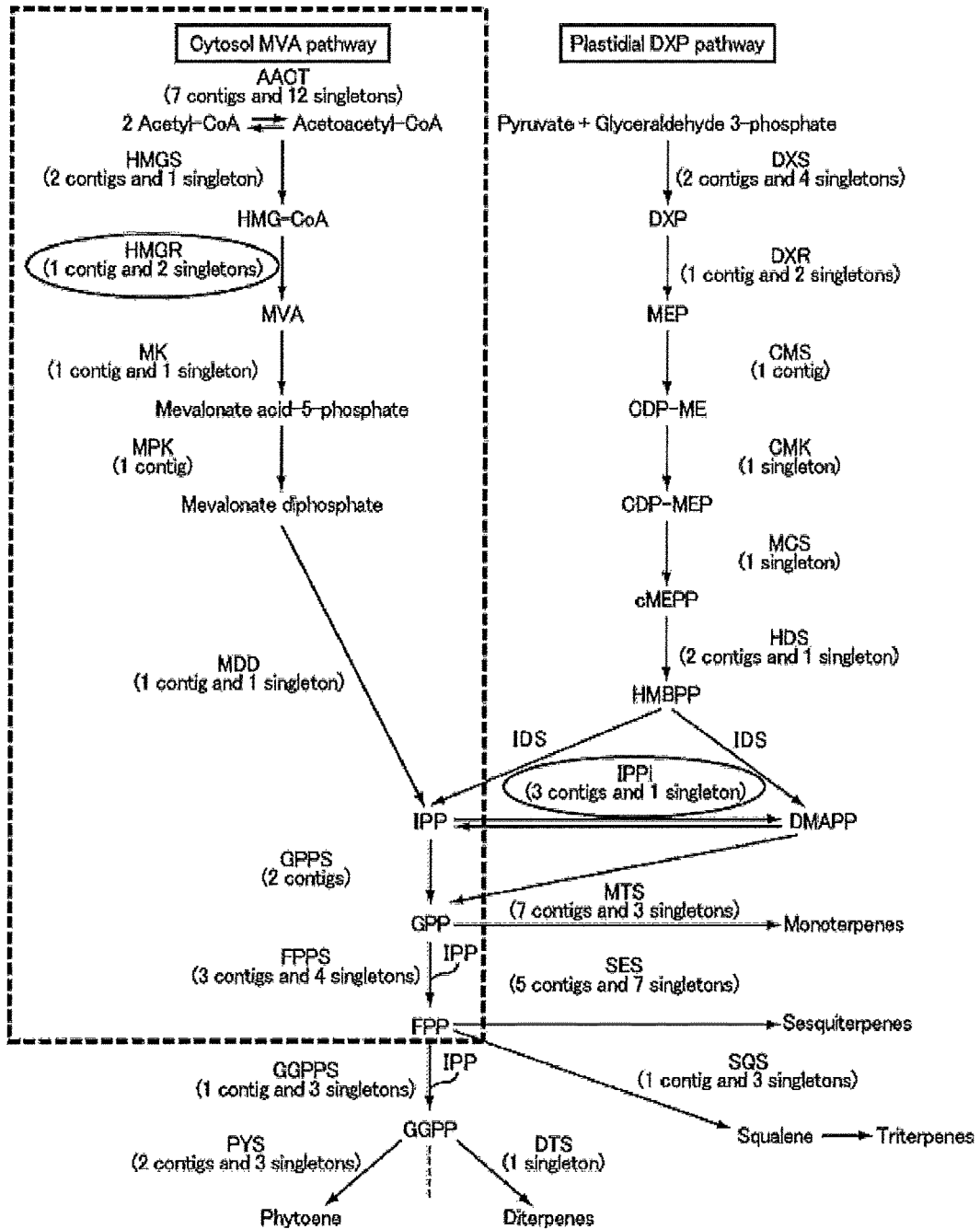

METHOD FOR MODULATING EXPRESSION OF SPECIFIC PROTEIN USING SPECIFIC TRANSCRIPTION FACTOR, ISOPRENOID-PRODUCING PLANT HAVING TRANSGENE ENCODING SPECIFIC TRANSCRIPTION FACTOR, AND METHOD FOR PRODUCING POLYISOPRENOID USING ISOPRENOID-PRODUCING PLANT

REFERENCE TO SEQUENCE LISTING SUBMITTED VIA EFS-WEB

This application includes an electronically submitted sequence listing in .txt format. The .txt file contains a sequence listing entitled "2015-10-28_5051-0359PUS1_ST25.txt" created on Oct. 28, 2015 and is 91,855 bytes in size. The sequence listing contained in this .txt file is part of the specification and is hereby incorporated by reference herein in its entirety.

TECHNICAL FIELD

The present invention relates to methods for regulating the expression of specific protein(s) by a specific transcription factor; isoprenoid-producing plants into which has been introduced a gene encoding a specific transcription factor; and methods for producing a polyisoprenoid using such an isoprenoid-producing plant.

BACKGROUND ART

Nowadays natural rubber (one example of polyisoprenoids) for use in industrial rubber products can be harvested from rubber-producing plants, such as *Hevea brasiliensis* (Para rubber tree) belonging to the family Euphorbiaceae, or *Ficus elastica* (Indian rubber tree) belonging to the family Moraceae.

At present, *Hevea brasiliensis* is practically the only one source of natural rubber for industrial rubber products. *Hevea brasiliensis* is a plant that can grow only in limited areas such as in Southeast Asia and South America. Moreover, *Hevea brasiliensis* requires about seven years from planting to mature enough for rubber extraction, and the period during which natural rubber can be extracted is limited to 20 to 30 years. Although more natural rubber is expected to be needed mainly by developing countries in years to come, for the reason mentioned above it is difficult to greatly increase the production of natural rubber using *Hevea brasiliensis*. Depletion of natural rubber sources is therefore of concern, and there are needs for stable natural rubber sources other than mature *Hevea brasiliensis* and for improvement in productivity of natural rubber from *Hevea brasiliensis*.

For example, an approach to improve productivity of natural rubber from *Hevea brasiliensis* is to extract more latex to produce more natural rubber. Specifically, such methods include a method of stimulating the trunk of rubber trees with ethylene or ethephon (2-chloroethylphosphonic acid); and a method of promoting laticifer differentiation by lanolin containing jasmonic acid, linolenic acid which is a precursor of jasmonic acid, or the like (see, for example, Non Patent Literature 1).

Unfortunately, if the method of increasing latex production via ethylene stimulation is applied to the trunk for a long term, then cracks may easily be formed in the bark. In addition, the aim of the ethylene stimulation is to allow latex to exude more smoothly from laticifers and is not to directly improve the tree's ability to produce latex. Therefore, this method provides only a limited and insufficient increase in latex production.

Although jasmonic acid or the like can be used to promote laticifer formation and thereby increase the number of laticifers, this method also has the problem that latex exuding from laticifers can coagulate at the cuts during the collection of latex by tapping, and therefore the produced latex may not be sufficiently collected.

Moreover, some factors, including light responses, wound responses, and cold treatment, are known to affect polyisoprenoid biosynthesis. However, it is not known specifically which transcription factor is activated in such a response to regulate polyisoprenoid biosynthesis.

CITATION LIST

Non Patent Literature

Non Patent Literature 1: Hao et al., Annals of Botany, 2000, Vol. 85, pp. 37-43

SUMMARY OF INVENTION

Technical Problem

The present invention was made to overcome the above problems, and an object of the present invention is to provide methods for enhancing the polyisoprenoid biosynthesis pathway. Further objects of the present invention are to provide isoprenoid-producing plants having an enhanced polyisoprenoid biosynthesis pathway, and methods for producing a polyisoprenoid using such an isoprenoid-producing plant.

Solution to Problem

The first aspect of the present invention relates to a method for regulating by a Dof transcription factor the expression of at least one protein selected from the group consisting of hydroxymethylglutaryl-CoA reductase, isopentenyl diphosphate isomerase, cis-prenyltransferase, and small rubber particle protein.

Preferably, the method includes introducing a gene encoding the Dof transcription factor into a host to regulate the expression of the protein in the host.

The gene is preferably either of the following DNAs:
[1] a DNA having the base sequence of SEQ ID NO:1, 3, or 5; and
[2] a DNA encoding a protein with transcription factor activity and capable of hybridizing under stringent conditions to a DNA having a base sequence complementary to the base sequence of SEQ ID NO:1, 3, or 5.

The method is preferably used to enhance the expression of at least one protein selected from the group consisting of hydroxymethylglutaryl-CoA reductase, cis-prenyltransferase, and small rubber particle protein, and more preferably to enhance the expression of hydroxymethylglutaryl-CoA reductase, cis-prenyltransferase, and small rubber particle protein.

The Dof transcription factor is preferably any of the following proteins:
[1] a protein having the amino acid sequence of SEQ ID NO:2, 4, or 6;
[2] a protein having transcription factor activity and having an amino acid sequence containing one or more amino acid substitutions, deletions, insertions and/or additions relative to the amino acid sequence of SEQ ID NO:2, 4, or 6; and

[3] a protein having transcription factor activity and having an amino acid sequence that has at least 80% sequence identity to the amino acid sequence of SEQ ID NO:2, 4, or 6.

The host is preferably an isoprenoid-producing plant.

The first aspect of the present invention also relates to an isoprenoid-producing plant, into which has been introduced a gene encoding a Dof transcription factor.

The gene is preferably either of the following DNAs:
[1] a DNA having the base sequence of SEQ ID NO:1, 3, or 5; and
[2] a DNA encoding a protein with transcription factor activity and capable of hybridizing under stringent conditions to a DNA having a base sequence complementary to the base sequence of SEQ ID NO:1, 3, or 5.

The first aspect of the present invention further relates to a method for producing a polyisoprenoid using the isoprenoid-producing plant.

The second aspect of the present invention relates to a method for regulating the expression of hydroxymethylglutaryl-CoA reductase by an Myb transcription factor.

Preferably, the method includes introducing a gene encoding the Myb transcription factor into a host to regulate the expression of hydroxymethylglutaryl-CoA reductase in the host.

The gene is preferably either of the following DNAs:
[1] a DNA having the base sequence of SEQ ID NO:25, 27, or 29; and
[2] a DNA encoding a protein with transcription factor activity and capable of hybridizing under stringent conditions to a DNA having a base sequence complementary to the base sequence of SEQ ID NO:25, 27, or 29.

The method is more preferably used to enhance the expression of hydroxymethylglutaryl-CoA reductase.

The Myb transcription factor is preferably any of the following proteins:
[1] a protein having the amino acid sequence of SEQ ID NO:26, 28, or 30;
[2] a protein having transcription factor activity and having an amino acid sequence containing one or more amino acid substitutions, deletions, insertions and/or additions relative to the amino acid sequence of SEQ ID NO:26, 28, or 30; and
[3] a protein having transcription factor activity and having an amino acid sequence that has at least 80% sequence identity to the amino acid sequence of SEQ ID NO:26, 28, or 30.

The host is preferably an isoprenoid-producing plant.

The second aspect of the present invention also relates to an isoprenoid-producing plant, into which has been introduced a gene encoding an Myb transcription factor.

The gene is preferably either of the following DNAs:
[1] a DNA having the base sequence of SEQ ID NO:25, 27, or 29; and
[2] a DNA encoding a protein with transcription factor activity and capable of hybridizing under stringent conditions to a DNA having a base sequence complementary to the base sequence of SEQ ID NO:25, 27, or 29.

The second aspect of the present invention further relates to a method for producing a polyisoprenoid using the isoprenoid-producing plant.

The third aspect of the present invention relates to a method for regulating the expression of hydroxymethylglutaryl-CoA reductase by a basic-helix-loop-helix (bHLH) transcription factor.

Preferably, the method includes introducing a gene encoding the bHLH transcription factor into a host to regulate the expression of hydroxymethylglutaryl-CoA reductase in the host.

The gene is preferably either of the following DNAs:
[1] a DNA having the base sequence of SEQ ID NO:40, 42, or 44; and
[2] a DNA encoding a protein with transcription factor activity and capable of hybridizing under stringent conditions to a DNA having a base sequence complementary to the base sequence of SEQ ID NO:40, 42, or 44.

The method is more preferably used to enhance the expression of hydroxymethylglutaryl-CoA reductase.

The bHLH transcription factor is preferably any of the following proteins:
[1] a protein having the amino acid sequence of SEQ ID NO:41, 43, or 45;
[2] a protein having transcription factor activity and having an amino acid sequence containing one or more amino acid substitutions, deletions, insertions and/or additions relative to the amino acid sequence of SEQ ID NO: 41, 43, or 45; and
[3] a protein having transcription factor activity and having an amino acid sequence that has at least 80% sequence identity to the amino acid sequence of SEQ ID NO: 41, 43, or 45.

The host is preferably an isoprenoid-producing plant.

The third aspect of the present invention also relates to an isoprenoid-producing plant, into which has been introduced a gene encoding a bHLH transcription factor.

The gene is preferably either of the following DNAs:
[1] a DNA having the base sequence of SEQ ID NO: 40, 42, or 44; and
[2] a DNA encoding a protein with transcription factor activity and capable of hybridizing under stringent conditions to a DNA having a base sequence complementary to the base sequence of SEQ ID NO:40, 42, or 44.

The third aspect of the present invention further relates to a method for producing a polyisoprenoid using the isoprenoid-producing plant.

Advantageous Effects of Invention

The method of the first aspect of the present invention, which is a method for regulating by a Dof transcription factor the expression of at least one protein selected from the group consisting of hydroxymethylglutaryl-CoA reductase, isopentenyl diphosphate isomerase, cis-prenyltransferase, and small rubber particle protein, is capable of enhancing the overall polyisoprenoid biosynthesis pathway. Moreover, the isoprenoid-producing plant of the first aspect of the present invention, into which has been introduced a gene encoding a Dof transcription factor, has an overall enhanced polyisoprenoid biosynthesis pathway. The use of the isoprenoid-producing plant in the production of polyisoprenoids increases polyisoprenoid production.

Since the method of the second aspect of the present invention is a method for regulating by an Myb transcription factor the expression of hydroxymethylglutaryl-CoA reductase that is a rate-limiting factor in the mevalonic acid (MVA) pathway, which is upstream in the polyisoprenoid biosynthesis pathway, the method enhances the rate-limiting step of isopentenyl diphosphate (IPP) biosynthesis in the MVA pathway, so that the polyisoprenoid biosynthesis pathway can be suitably enhanced. Moreover, the isoprenoid-producing plant of the second aspect of the present invention, into which has been introduced a gene encoding an Myb transcription factor, has a suitably enhanced polyisoprenoid biosynthesis pathway. The use of the isoprenoid-producing plant in the production of polyisoprenoids increases polyisoprenoid production.

Since the method of the third aspect of the present invention is a method for regulating by a basic-helix-loop-helix (bHLH) transcription factor the expression of hydroxymethylglutaryl-CoA reductase that is a rate-limiting factor in the mevalonic acid (MVA) pathway, which is upstream in the polyisoprenoid biosynthesis pathway, the method enhances the rate-limiting step of isopentenyl diphosphate (IPP) biosynthesis in the MVA pathway, so that the polyisoprenoid biosynthesis pathway can be suitably enhanced. Moreover, the isoprenoid-producing plant of the third aspect of the present invention, into which has been introduced a gene encoding a bHLH transcription factor, has a suitably enhanced polyisoprenoid biosynthesis pathway. The use of the isoprenoid-producing plant in the production of polyisoprenoids increases, polyisoprenoid production.

BRIEF DESCRIPTION OF DRAWINGS

FIG. 1 is a schematic view of a part of the polyisoprenoid biosynthesis pathway.

DESCRIPTION OF EMBODIMENTS (First Aspect of the Present Invention)

The present inventors have studied various ways to enhance the overall polyisoprenoid biosynthesis pathway. FIG. 1 shows a part of the polyisoprenoid biosynthesis pathway. There are two known pathways, the mevalonic acid (MVA) pathway (cytosol MVA pathway as shown in FIG. 1) and the MEP pathway (plastidial DXP pathway as shown in FIG. 1), for biosynthesis of isopentenyl diphosphate (IPP), which is an important member of the polyisoprenoid biosynthesis pathway.

The present inventors focused on the MVA pathway which is a common pathway that supplies IPP in rubber latex synthesis, and selected, from various proteins involved in the polyisoprenoid biosynthesis pathway, some proteins that are expected to have important roles in view of enhancing the entire pathway enclosed in the dotted line in FIG. 1 or the entire downstream pathway.

Specifically, the following four proteins were selected: hydroxymethylglutaryl-CoA reductase (HMG-CoA reductase) that is a rate-limiting factor in the MVA pathway, which is a pathway to IPP biosynthesis; isopentenyl diphosphate isomerase (IPP isomerase) that is involved in isomerization of IPP; cis-prenyltransferase that is thought to be involved in isoprenoid chain elongation; and small rubber particle protein (SRPP) that is known to be involved in polyisoprenoid biosynthesis.

In order to simultaneously regulate the expression of the four proteins, that is, to comprehensively regulate the expression of the four proteins, the present inventors sought a transcription factor capable of regulating (or comprehensively regulating) the expression of all the four proteins. Specifically, DNA fragments from leaves of *Hevea brasiliensis* which contain genes encoding the four proteins (the amino acid sequences of cis-prenyltransferase, HMG-CoA reductase, IPP isomerase, and SRPP are set forth in the sequence listing as SEQ ID NOs:8, 10, 12, and 14, respectively) (the base sequences of the genes encoding cis-prenyltransferase, HMG-CoA reductase, IPP isomerase, and SRPP are set forth in the sequence listing as SEQ ID NOs:7, 9, 11, and 13, respectively) and their promoter regions were cloned (see EXAMPLES for details). The base sequences of the resulting DNA fragments were analyzed to reveal the base sequences of the promoter regions of the genes encoding the proteins.

Additionally, the revealed base sequences of the promoter regions of the four proteins were analyzed using a plant promoter database (a database of plant cis-acting regulatory DNA elements (PLACE)). The analysis revealed that the sequences contain a lot of Dof transcription factor binding sites, and all the promoter sequences of the four genes analyzed are similarly rich in the DOFCOREZM (AAAG) motif to which Dof transcription factors bind. The number of DOFCOREZM motifs is the highest for HMG-CoA reductase, IPP isomerase, and SRPP, and the third highest for cis-prenyltransferase, among the transcription factor binding motifs found in each case.

These results strongly suggest that Dof transcription factors are transcription factors capable of regulating the expression of all the four proteins, or in other words, transcription factors that can regulate the overall polyisoprenoid biosynthesis pathway. Then, a validation test using yeast cells was performed to confirm that the expression of the four proteins is enhanced by the use of Dof5.4 (the base sequence and the amino acid sequence of Dof5.4 from *Arabidopsis thaliana* are set forth in the sequence listing as SEQ ID NOs:1 and 2, respectively), Dof2.2 (the base sequence and the amino acid sequence of Dof2.2 from *Arabidopsis thaliana* are set forth in the sequence listing as SEQ ID NOs:3 and 4, respectively), or Dof5.3 (the base sequence and the amino acid sequence of Dof5.3 from *Arabidopsis thaliana* are set forth in the sequence listing as SEQ ID NOs:5 and 6, respectively) among Dof transcription factors.

As described above, the present inventors have found that Dof transcription factors are capable of comprehensively enhancing the expression of HMG-CoA reductase, IPP isomerase, cis-prenyltransferase, and SRPP, and thus can enhance the overall polyisoprenoid biosynthesis pathway. Another finding is that since the Dof transcription factors can enhance the overall polyisoprenoid biosynthesis pathway, an isoprenoid-producing plant into which has been introduced a gene encoding such a Dof transcription factor can be used in the production of polyisoprenoids to increase polyisoprenoid production.

Theoretically, it is desirable to enhance the expression of HMG-CoA reductase, cis-prenyltransferase and SRPP while suppressing the expression of IPP isomerase. However, although the Dof transcription factors enhance the expression of IPP isomerase as well as the expression of HMG-CoA reductase, cis-prenyltransferase and SRPP, polyisoprenoid production can be successfully increased because the overall polyisoprenoid biosynthesis pathway is enhanced.

As used herein, "hydroxymethylglutaryl-CoA reductase (HMG-CoA reductase)" is a rate-limiting enzyme of the mevalonic acid pathway and is intended to include both hydroxymethylglutaryl-CoA reductase (NADPH) (EC 1.1.1.34) and hydroxymethylglutaryl-CoA reductase (EC 1.1.1.88).

As used herein, "isopentenyl diphosphate isomerase (IPP isomerase)" is an enzyme that catalyzes the isomerization between isopentenyl diphosphate (IPP) and its isomer, dimethylallyl pyrophosphate (DMAPP).

As used herein, "cis-prenyltransferase" is an enzyme that catalyzes cis-chain elongation of isoprenoid compounds.

As used herein, "small rubber particle protein (SRPP)" is a small rubber particle-associated protein which is associated with small rubber particles of 10 μm or less in diameter in the latex of *Hevea brasiliensis* or the like.

The method of the first aspect of the present invention is a method for regulating by a Dof transcription factor the expression of at least one protein selected from the group consisting of hydroxymethylglutaryl-CoA reductase, isopentenyl diphosphate isomerase, cis-prenyltransferase, and small rubber particle protein.

The Dof transcription factor is not particularly limited, as long as it is a transcription factor that contains a C2C2 zinc finger DNA binding domain (Dof domain). Examples include Dof5.4 (the base sequence and the amino acid sequence of Dof5.4 from *Arabidopsis thaliana* are set forth in the sequence listing as SEQ ID NOs: 1 and 2, respectively), Dof2.2 (the base sequence and the amino acid sequence of Dof2.2 from *Arabidopsis thaliana* are set forth in the sequence listing as SEQ ID NOs:3 and 4, respectively), Dof5.3 (the base sequence and the amino acid sequence of Dof5.3 from *Arabidopsis thaliana* are set forth in the sequence listing as SEQ ID NOs: 5 and 6, respectively), Dof1, and Dof4.6.

The term "transcription factor" as used herein refers to a protein having an activity of increasing or decreasing the rate of transcription of a gene or genes.

The origin of the Dof transcription factor is not particularly limited, but the Dof transcription factor is preferably a transcription factor from *Hevea brasiliensis, Sonchus oleraceus, Parthenium argentatum, Taraxacum koksaghyz,* or *Arabidopsis thaliana*.

(Amino Acid Sequence of Dof Transcription Factor)

The following protein [1] is a specific example of the Dof transcription factor:

[1] a protein having the amino acid sequence of SEQ ID NO:2, 4, or 6.

Moreover, it is known that some transcription factors have transcription factor activity even when one or more amino acid substitutions, deletions, insertions, or additions are introduced into their original amino acid sequences. Considering this fact, another specific example of the Dof transcription factor is the following protein [2]:

[2] a protein having transcription factor activity and having an amino acid sequence containing one or more amino acid substitutions, deletions, insertions and/or additions relative to the amino acid sequence of SEQ ID NO:2, 4, or 6.

The term "transcription factor activity" as used herein refers to an activity of increasing or decreasing the rate of transcription of at least one gene selected from the group consisting of genes encoding hydroxymethylglutaryl-CoA reductase, isopentenyl diphosphate isomerase, cis-prenyltransferase, and small rubber particle protein.

For maintenance of transcription factor activity, the number of amino acid substitutions, deletions, insertions, and/or additions relative to the amino acid sequence of SEQ ID NO:2 is preferably 1 or more, more preferably 1 to 61, still more preferably 1 to 46, particularly preferably 1 to 31, most preferably 1 to 15, even most preferably 1 to 6, and still even most preferably 1 to 3.

Also for maintenance of transcription factor activity, the number of amino acid substitutions, deletions, insertions, and/or additions relative to the amino acid sequence of SEQ ID NO:4 is preferably 1 or more, more preferably 1 to 68, still more preferably 1 to 51, particularly preferably 1 to 34, most preferably 1 to 17, even most preferably 1 to 7, and still even most preferably 1 to 3.

Also for maintenance of transcription factor activity, the number of amino acid substitutions, deletions, insertions, and/or additions relative to the amino acid sequence of SEQ ID NO:6 is preferably 1 or more, more preferably 1 to 51, still more preferably 1 to 39, particularly preferably 1 to 26, most preferably 1 to 13, even most preferably 1 to 5, and still even most preferably 1 to 3.

Among other amino acid substitutions, conservative substitutions are preferred. Specific examples include substitutions within each of the following groups in the parentheses: (glycine, alanine), (valine, isoleucine, leucine), (aspartic acid, glutamic acid), (asparagine, glutamine), (serine, threonine), (lysine, arginine), (phenylalanine, tyrosine), and the like.

The amino acid substitutions, deletions, insertions, and/or additions are preferably introduced into regions other than Dof transcription factor activity domains, binding domains that bind to transcription factor binding sites, and other important portions involved in transcription factor activity. Those skilled in the art can appropriately identify such domains by homology analysis with known Dof transcription factors.

It is also known that some proteins with amino acid sequences having high sequence identity to the amino acid sequence of a transcription factor also have similar activity. Considering this fact, another specific example of the Dof transcription factor is the following protein [3]:

[3] a protein having transcription factor activity and having an amino acid sequence that has at least 80% sequence identity to the amino acid sequence of SEQ ID NO:2, 4, or 6.

For maintenance of transcription factor activity, the sequence identity to the amino acid sequence of SEQ ID NO:2, 4, or 6 is preferably at least 85%, more preferably at least 90%, still more preferably at least 95%, particularly preferably at least 98%, and most preferably at least 99%.

The sequence identity between amino acid sequences or base sequences may be determined using the algorithm BLAST® [Pro. Natl. Acad. Sci. USA, 90, 5873 (1993)] developed by Karlin and Altschul or FASTA [Methods Enzymol., 183, 63 (1990)].

Whether a protein has transcription factor activity may be determined by conventionally known techniques, such as gel shift assays, or reporter assays using a reporter gene encoding β-galactosidase, luciferase, green fluorescent protein (GFP), or the like.

The Dof transcription factor is preferably any of the following proteins:

[1-1] a protein having the amino acid sequence of SEQ ID NO:2 or 4;

[2-1] a protein having transcription factor activity and having an amino acid sequence containing one or more amino acid substitutions, deletions, insertions and/or additions relative to the amino acid sequence of SEQ ID NO:2 or 4; and

[3-1] a protein having transcription factor activity and having an amino acid sequence that has at least 80% sequence identity to the amino acid sequence of SEQ ID NO:2 or 4.

The Dof transcription factor is more preferably any of the following proteins:

[1-2] a protein having the amino acid sequence of SEQ ID NO:2;

[2-2] a protein having transcription factor activity and having an amino acid sequence containing one or more amino acid substitutions, deletions, insertions, and/or additions relative to the amino acid sequence of SEQ ID NO:2; and

[3-2] a protein having transcription factor activity and having an amino acid sequence that has at least 80% sequence identity to the amino acid sequence of SEQ ID NO:2.

(DNA Encoding Dof Transcription Factor)

Moreover, the DNA encoding the Dof transcription factor may be either of the following DNAs:

[1] a DNA having the base sequence of SEQ ID NO:1, 3, or 5; and

[2] a DNA encoding a protein with transcription factor activity and capable of hybridizing under stringent conditions to a DNA having a base sequence complementary to the base sequence of SEQ ID NO:1, 3, or 5.

In this context, the term "hybridizing" means a process in which the DNA hybridizes to a DNA having a particular base sequence or a part of the DNA. Thus, the DNA having a particular base sequence or part of the DNA may have a base sequence long enough to be usable as a probe in Northern or Southern blot analysis or as an oligonucleotide primer in polymerase chain reaction (PCR) analysis. The DNA used as a probe may have a length of at least 100 bases, preferably at least 200 bases, and more preferably at least 500 bases although it may be a DNA of at least 10 bases, and preferably of at least 15 bases in length.

Techniques to perform DNA hybridization experiments are well known. The hybridization conditions under which experiments are performed may be determined according to, for example, Molecular Cloning, 2nd ed. and 3rd ed. (2001); Methods for General and Molecular Bacteriology, ASM Press (1994); Immunology methods manual, Academic press (Molecular); and many other standard textbooks.

The stringent conditions may include, for example, an overnight incubation at 42° C. of a DNA-immobilized filter and a DNA probe in a solution containing 50% formamide, 5×SSC (750 mM sodium chloride and 75 mM sodium citrate), 50 mM sodium phosphate (pH 7.6), 5×Denhardt's solution, 10% dextran sulfate, and 20 µg/l denatured salmon sperm DNA, followed by washing the filter for example in a 0.2×SSC solution at approximately 65° C. Less stringent conditions may also be used. Changes in the stringency may be accomplished through the manipulation of formamide concentration (lower percentages of formamide result in lower stringency), salt concentrations or temperature. For example, low stringent conditions include an overnight incubation at 37° C. in a solution containing 6×SSCE (20×SSCE: 3 mol/l sodium chloride, 0.2 mol/l sodium dihydrogen phosphate, 0.02 mol/l EDTA, pH 7.4), 0.5% SDS, 30% formamide, and 100 µg/l denatured salmon sperm DNA, followed by washing in a 1×SSC solution containing 0.1% SDS at 50° C. Moreover, to achieve even lower stringency, washes performed following hybridization may be done at higher salt concentrations (e.g. 5×SSC) in the above-mentioned low stringent conditions.

Variations in the above various conditions may be accomplished through the inclusion or substitution of blocking reagents used to suppress background in hybridization experiments. The inclusion of blocking reagents may require modification of the hybridization conditions for compatibility.

The DNA capable of hybridization under stringent conditions as described above may be a DNA having a base sequence that has at least 80%, preferably at least 90%, more preferably at least 95%, even more preferably at least 98%, and particularly preferably at least 99% sequence identity to the base sequence of SEQ ID NO: 1, 3, or 5 as calculated using a program such as BLAST® or FASTA with the parameters mentioned above.

Whether the DNA capable of hybridizing under stringent conditions to the DNA mentioned above encodes a protein with transcription factor activity may be determined by conventionally known techniques, such as gel shift assays, or reporter assays using a reporter gene encoding β-galactosidase, luciferase, green fluorescent protein (GFP), or the like.

The DNA encoding the Dof transcription factor is preferably either of the following DNAs:

[1-1] a DNA having the base sequence of SEQ ID NO:1 or 3; and

[2-1] a DNA encoding a protein with transcription factor activity and capable of hybridizing under stringent conditions to a DNA having a base sequence complementary to the base sequence of SEQ ID NO:1 or 3.

More preferred is either of the following DNAs:

[1-1] a DNA having the base sequence of SEQ ID NO:1; and

[2-1] a DNA encoding a protein with transcription factor activity and capable of hybridizing under stringent conditions to a DNA having a base sequence complementary to the base sequence of SEQ ID NO:1.

The Dof transcription factor and the DNA encoding the Dof transcription factor may be obtained by site-directed mutagenesis of, for example, the base sequence of SEQ ID NO:1, 3, or 5 (the base sequence of Dof5.4 from *Arabidopsis thaliana*, the base sequence of Dof2.2 from *Arabidopsis thaliana*, or the base sequence of Dof5.3 from *Arabidopsis thaliana*) according to site-directed mutagenesis techniques described in Molecular Cloning, A Laboratory Manual, Second Edition, Cold Spring Harbor Laboratory Press (1989); Current Protocols in Molecular Biology, John Wiley & Sons (1987-1997); Nucleic Acids Research, 10, 6487 (1982); Proc. Natl. Acad. Sci. USA, 79, 6409 (1982); Gene, 34, 315 (1985); Nucleic Acids Research, 13, 4431 (1985); Proc. Natl. Acad. Sci. USA, 82, 488 (1985), etc.

(Transformant)

The gene encoding the Dof transcription factor can be introduced into a host to create an organism (transformant) that is transformed to express the Dof transcription factor. Then this transformant expresses the Dof transcription factor, which regulates (enhances) the expression of at least one protein selected from the group consisting of hydroxymethylglutaryl-CoA reductase, isopentenyl diphosphate isomerase, cis-prenyltransferase, and small rubber particle protein (preferably at least one protein selected from the group consisting of hydroxymethylglutaryl-CoA reductase, cis-prenyltransferase, and small rubber particle protein).

More specifically, it comprehensively enhances the expression of the four proteins: hydroxymethylglutaryl-CoA reductase, isopentenyl diphosphate isomerase, cis-prenyltransferase, and small rubber particle protein (preferably the three proteins: hydroxymethylglutaryl-CoA reductase, cis-prenyltransferase, and small rubber particle protein). Therefore, the transformant has an overall enhanced polyisoprenoid biosynthesis pathway and is thereby capable of producing more polyisoprenoids.

The following briefly describes how to prepare an organism (transformant) that is transformed to express a Dof transcription factor. The brief description below mainly focuses on how to prepare a transformant that is transformed to express the above-mentioned Dof transcription factor. Once a Dof transcription factor-encoding gene to be introduced has been determined, such a transformant can be prepared by conventionally known methods.

Specifically, for example, a DNA containing the base sequence of SEQ ID NO:1, 3, or 5 (the base sequence of Dof5.4 from *Arabidopsis thaliana*, the base sequence of Dof2.2 from *Arabidopsis thaliana*, or the base sequence of Dof5.3 from *Arabidopsis thaliana*) is inserted downstream of a promoter of an appropriate expression vector using appropriate restriction enzymes and the like to prepare a recombinant DNA, which is then introduced into host cells compatible with the expression vector to obtain a transformant.

Although the above description relates to the cases where a DNA containing the base sequence of SEQ ID NO: 1, 3, or 5 (the base sequence of Dof5.4 from *Arabidopsis thaliana*, the base sequence of Dof2.2 from *Arabidopsis thaliana*, or the base sequence of Dof5.3 from *Arabidopsis thaliana*) is used, DNAs encoding other Dof transcription factors from *Arabidopsis thaliana* or Dof transcription factors from organisms other than *Arabidopsis thaliana* may be used. In such cases, screening may be performed by known techniques, such as using a part of the base sequence of SEQ ID NO:1 as a probe, to identify and isolate such DNAs encoding the Dof transcription factors. The method for isolating a DNA molecule of interest using a DNA molecule as a probe is described in, for example, Molecular Cloning, 2nd edition, Cold Spring Harbor Press (1989). DNAs obtained by mutagenesis of the DNAs mentioned above may also be used.

Any of microorganisms, yeasts, animal cells, insect cells, plant cells, and the like can be used as the host (host cells), as long as they are capable of expressing a gene of interest. Since the only organisms currently known to biosynthesize polyisoprenoids are plants (isoprenoid-producing plants), the host is preferably a plant (an isoprenoid-producing plant), and the host cells are preferably plant cells (cells of an isoprenoid-producing plant). Note that if a future advance in technology allows cells other than plant cells to biosynthesize polyisoprenoids, the gene encoding the Dof transcription factor can be suitably introduced into such cells.

The isoprenoid-producing plant is not particularly limited, as long as it is capable of producing an isoprenoid. Examples include plants of the genus *Hevea*, such as *Hevea brasiliensis*; plants of the genus *Sonchus*, such as *Sonchus oleraceus, Sonchus asper*, and *Sonchus brachyotus*; plants of the genus *Solidago*, such as *Solidago altissima, Solidago virgaurea* subsp. *asiatica, Solidago virgaurea* subsp. *leipcarpa, Solidago virgaurea* subsp. *leipcarpa* f. *paludosa, Solidago virgaurea* subsp. *gigantea*, and *Solidago gigantea* Ait. var. *leiophylla* Fernald; plants of the genus *Helianthus*, such as *Helianthus annuus, Helianthus argophyllus, Helianthus atrorubens, Helianthus debilis, Helianthus decapetalus*, and *Helianthus giganteus*; plants of the genus *Taraxacum*, such as *Taraxacum, Taraxacum venustum* H. Koidz, *Taraxacum hondoense* Nakai, *Taraxacum platycarpum* Dahlst, *Taraxacum japonicum, Taraxacum officinale* Weber, and *Taraxacum koksaghyz*; plants of the genus *Ficus*, such as *Ficus carica, Ficus elastica, Ficus pumila* L., *Ficus erecta* Thumb., *Ficus ampelas* Burm. f., *Ficus benguetensis* Merr., *Ficus irisana* Elm., *Ficus microcarpa* L.f., *Ficus septica* Burm. f., and *Ficus benghalensis*; plants of the genus *Parthenium*, such as *Parthenium argentatum, Parthenium hysterophorus*, and *Parthenium hysterophorus*; and *Lactuca serriola* and *Ficus benghalensis*. In particular, the isoprenoid-producing plant is preferably at least one selected from the group consisting of plants of the genera *Hevea, Sonchus, Taraxacum*, and *Parhenium*, and more preferably at least one selected from the group consisting of *Hevea brasiliensis, Sonchus oleraceus, Parthenium argentatum*, and *Taraxacum koksaghyz*.

Examples of expression vectors that can be used include vectors that are capable of autonomous replication in the host cells or of being incorporated into a chromosome thereof and contain a promoter at a position that permits transcription of the recombinant DNA.

In the case where plant cells are used as host cells, a pBI vector, a pUC vector, a Ti plasmid or tobacco mosaic virus vector, for example, may be used as an expression vector.

Any promoter that functions in plant cells can be used. Examples include cauliflower mosaic virus (CaMV) 35S promoter, rice actin-1 promoter, nopaline synthase gene promoter, tobacco mosaic virus 35S promoter, and rice actin gene promoter.

Preferred are expression vectors with promoters that are specifically expressed in tissues in which isoprenoid compounds are biosynthesized, such as laticifers. If the promoters are specifically expressed in tissues in which polyisoprenoids are biosynthesized, retardation of plant growth and other adverse effects can be prevented.

The recombinant vector can be introduced by any method that allows the DNA to be introduced into plant cells. Examples include methods using *Agrobacterium* (JP S59-140885 A, JP S60-70080 A, WO94/00977), electroporation (JP S60-251887 A), and methods using a particle gun (gene gun) (JP 2606856 B, JP 2517813 B).

Transformants (transgenic plant cells) into which has been introduced a gene encoding a Dof transcription factor can be prepared by these methods or the like.

The first aspect of the present invention provides an isoprenoid-producing plant into which has been introduced a gene encoding a Dof transcription factor. The isoprenoid-producing plant is not particularly limited, as long as it is an isoprenoid-producing plant containing the transgenic plant cells. It is intended to include, for example, in addition to transgenic plant cells prepared by the above-described methods, for example, all of their progeny or clones and even progeny plants obtained by passaging these cells. Once transgenic plant cells into which the DNA or vector has been introduced in the genome are obtained, progeny or clones can be obtained from the transgenic plant cells by sexual or asexual reproduction, tissue culture, cell culture, cell fusion, or the like. Further, the transgenic plant cells, or their progeny or clones may be used to obtain reproductive materials (e.g. seeds, fruits, cuttings, stem tubers, root tubers, shoots, adventitious buds, adventitious embryos, calluses, protoplasts), which can then be used to produce the isoprenoid-producing plant on a large scale.

Techniques to regenerate plants from transgenic plant cells are already known; for example, Doi et al. disclose techniques for eucalyptus (JP 2000-316403 A), Fujimura et al. disclose techniques for rice (Fujimura et al., (1995), Plant Tissue Culture Lett., vol. 2: p 74-), Shillito et al. disclose techniques for corn (Shillito et al., (1989), Bio/Technology, vol. 7: p 581-), Visser et al. disclose techniques for potato (Visser et al., (1989), Theor. Appl. Genet., vol. 78: p 589-), and Akama et al. disclose techniques for *Arabidopsis thaliana* (Akama et al., (1992), Plant Cell Rep., vol. 12: p 7-). Those skilled in the art can regenerate plants from transgenic plant cells according to these documents.

Whether a target transcription factor gene is expressed in a regenerated plant may be determined by well-known methods. For example, western blot analysis may be used to assess the expression of a target transcription factor.

Seeds can be obtained from the transgenic plant, for example, as follows: the transgenic plant is rooted in an appropriate medium and then transplanted to water-containing soil in a pot, and grown under proper cultivation conditions so as to finally produce seeds, which are then collected. Further, plants can be grown from seeds, for example, as follows: seeds obtained from the transgenic plant as described above are sown in water-containing soil, and grown under proper cultivation conditions into plants.

According to the first aspect of the present invention, the isoprenoid-producing plant into which has been introduced a gene encoding a Dof transcription factor can be used in the production of polyisoprenoids to increase polyisoprenoid production. Specifically, polyisoprenoids can be produced by culturing transgenic plant cells prepared as described above, calluses obtained from such transgenic plant cells, cells redifferentiated from such calluses, or the like in an appropriate medium, or by growing transgenic plants regenerated from the transgenic plant cells, plants grown from seeds collected from such transgenic plants, or the like under proper cultivation conditions. The isoprenoid-producing plant of the first aspect of the present invention has a polyisoprenoid biosynthesis pathway enhanced overall by the Dof transcription factor introduced therein, and is thereby capable of producing more polyisoprenoids.

The term "polyisoprenoid" as used herein is a generic term used to refer to polymers having isoprene ($C_5H_8$) units. Examples of polyisoprenoids include polymers such as monoterpenes ($C_{10}$), sesquiterpenes ($C_{15}$), diterpenes ($C_{20}$), sesterterpenes ($C_{25}$), triterpenes ($C_{30}$), tetraterpenes ($C_{40}$), and natural rubber.

As described above, the first aspect of the present invention enables to regulate (enhance) by a Dof transcription factor the expression of at least one protein selected from the group consisting of hydroxymethylglutaryl-CoA reductase, isopentenyl diphosphate isomerase, cis-prenyltransferase, and small rubber particle protein, and thereby to enhance the overall polyisoprenoid biosynthesis pathway to increase polyisoprenoid production.

Moreover, the isoprenoid-producing plant of the first aspect of the present invention into which has been introduced a gene encoding a Dof transcription factor has an overall enhanced polyisoprenoid biosynthesis pathway. The use of the isoprenoid-producing plant in the production of polyisoprenoids increases polyisoprenoid production.

Thus, the method of the first aspect of the present invention, the isoprenoid-producing plant of the first aspect of the present invention, and the method of producing a polyisoprenoid of the first aspect of the present invention, all of which are capable of increasing polyisoprenoid production, can be effective for natural rubber source depletion that is of concern.

(Second Aspect of the Present Invention)

The present inventors have studied various ways to enhance the polyisoprenoid biosynthesis pathway. FIG. 1 shows a part of the polyisoprenoid biosynthesis pathway. There are two known pathways, the mevalonic acid (MVA) pathway (cytosol MVA pathway as shown in FIG. 1) and the MEP pathway (plastidial DXP pathway as shown in FIG. 1), for biosynthesis of isopentenyl diphosphate (IPP), which is an important member of the polyisoprenoid biosynthesis pathway.

The present inventors focused on the MVA pathway which is a common pathway that supplies IPP in rubber latex synthesis, and selected, from various proteins involved in the polyisoprenoid biosynthesis pathway, some proteins that are expected to have important roles in view of enhancing the pathway enclosed in the dotted line in FIG. 1. Further, they found out that, among these proteins, hydroxymethylglutaryl-CoA reductase (HMG-CoA reductase) is a rate-limiting factor in the MVA pathway.

In order to regulate the expression of HMG-CoA reductase, the present inventors then sought a transcription factor capable of regulating the expression of HMG-CoA reductase. Specifically, a DNA fragment from leaves of *Hevea brasiliensis* which contains a gene encoding HMG-CoA reductase (the amino acid sequence of HMG-CoA reductase is set forth in the sequence listing as SEQ ID NO:32) (the base sequence of the gene is set forth in the sequence listing as SEQ ID NO:31) and its promoter region was cloned (see EXAMPLES for details). The base sequence of the resulting DNA fragment was analyzed to reveal the base sequence of the promoter region of the gene encoding HMG-CoA reductase.

Additionally, the revealed base sequence of the promoter region was analyzed using a plant promoter database (a database of plant cis-acting regulatory DNA elements (PLACE)). The analysis revealed that the sequence contains a lot of Myb transcription factor binding (recognition) sites (WAACCA, CCWACC, CANNTG).

These results strongly suggest that Myb transcription factors are transcription factors capable of regulating the expression of HMG-CoA reductase, or in other words, transcription factors that enhance the rate-limiting step of IPP biosynthesis in the MVA pathway and can thereby suitably regulate the polyisoprenoid biosynthesis pathway. Then, a validation test using yeast cells was performed to confirm that the expression of HMG-CoA reductase is enhanced by the use of Myb6 (the base sequence and the amino acid sequence of Myb6 from *Arabidopsis thaliana* are set forth in the sequence listing as SEQ ID NOs:25 and 26, respectively), Myb3 (the base sequence and the amino acid sequence of Myb3 from *Arabidopsis thaliana* are set forth in the sequence listing as SEQ ID NOs:27 and 28, respectively), or EPR1 (the base sequence and the amino acid sequence of EPR1 from *Arabidopsis thaliana* are set forth in the sequence listing as SEQ ID NOs:29 and 30, respectively) among Myb transcription factors.

As described above, the present inventors have found that Myb transcription factors can suitably enhance the expression of HMG-CoA reductase, and thus enhance the rate-limiting step of IPP biosynthesis in the MVA pathway and can thereby suitably enhance the polyisoprenoid biosynthesis pathway. Another finding is that since the Myb transcription factors enhance the rate-limiting step of IPP biosynthesis in the MVA pathway and can thereby suitably enhance the polyisoprenoid biosynthesis pathway, an isoprenoid-producing plant into which has been introduced a gene encoding such an Myb transcription factor can be used in the production of polyisoprenoids to increase polyisoprenoid production.

As used herein, "hydroxymethylglutaryl-CoA reductase (HMG-CoA reductase)" is a rate-limiting enzyme of the mevalonic acid pathway and is intended to include both hydroxymethylglutaryl-CoA reductase (NADPH) (EC 1.1.1.34) and hydroxymethylglutaryl-CoA reductase (EC 1.1.1.88).

The method of the second aspect of the present invention is a method for regulating the expression of hydroxymethylglutaryl-CoA reductase by an Myb transcription factor.

Although Myb transcription factors are classified into three major types based on the structural features, any type of Myb transcription factor can be used as long as, for example, it has the structural features of the R1R2R3 type which regulates cell proliferation by regulating cell cycles, the structural features of the R2R3 type which regulates various biological phenomena such as pigment synthesis, morphogenesis, and environmental response, or the structural features of the type having one R1-like or R3-like domain which is involved in photoregulation, morphogenesis, and diseases and disorders. Examples include Myb6 (the base sequence and the amino acid sequence of Myb6 from *Arabidopsis thaliana* are set forth in the sequence listing as SEQ ID NOs:25 and 26, respectively), Myb3 (the base sequence and the amino acid sequence of Myb3 from *Arabidopsis thaliana* are set forth in the sequence listing as SEQ ID NOs: 27 and 28, respectively), and EPR1 (the base sequence and the amino acid sequence of EPR1 from *Arabidopsis thaliana* are set forth in the sequence listing as SEQ ID NOs:29 and 30, respectively).

The term "transcription factor" as used herein refers to a protein having an activity of increasing or decreasing (preferably increasing) the rate of transcription of a gene or genes.

The origin of the Myb transcription factor is not particularly limited, but the Myb transcription factor is preferably a transcription factor from *Hevea brasiliensis*, *Sonchus oleraceus*, *Parthenium argentatum*, *Taraxacum koksaghyz*, or *Arabidopsis thaliana*.

(Amino Acid Sequence of Myb Transcription Factor)

The following protein [1] is a specific example of the Myb transcription factor:

[1] a protein having the amino acid sequence of SEQ ID NO:26, 28, or 30.

Moreover, it is known that some transcription factors have transcription factor activity even when one or more amino acid substitutions, deletions, insertions, or additions are introduced into their original amino acid sequences. Considering this fact, another specific example of the Myb transcription factor is the following protein [2]:

[2] a protein having transcription factor activity and having an amino acid sequence containing one or more amino acid substitutions, deletions, insertions and/or additions relative to the amino acid sequence of SEQ ID NO:26, 28, or 30.

The term "transcription factor activity" as used herein refers to an activity of increasing or decreasing (preferably increasing) the rate of transcription of a gene encoding hydroxymethylglutaryl-CoA reductase.

For maintenance of transcription factor activity, the number of amino acid substitutions, deletions, insertions, and/or additions relative to the amino acid sequence of SEQ ID NO:26 is preferably 1 or more, more preferably 1 to 47, still more preferably 1 to 35, particularly preferably 1 to 24, most preferably 1 to 12, even most preferably 1 to 5, and still even most preferably 1 or 2.

For maintenance of transcription factor activity, the number of amino acid substitutions, deletions, insertions, and/or additions relative to the amino acid sequence of SEQ ID NO:28 is preferably 1 or more, more preferably 1 to 51, still more preferably 1 to 39, particularly preferably 1 to 26, most preferably 1 to 13, even most preferably 1 to 5, and still even most preferably 1 to 3.

For maintenance of transcription factor activity, the number of amino acid substitutions, deletions, insertions, and/or additions relative to the amino acid sequence of SEQ ID NO:30 is preferably 1 or more, more preferably 1 to 74, still more preferably 1 to 56, particularly preferably 1 to 37, most preferably 1 to 19, even most preferably 1 to 7, and still even most preferably 1 to 4.

Among other amino acid substitutions, conservative substitutions are preferred. Specific examples include substitutions within each of the following groups in the parentheses: (glycine, alanine), (valine, isoleucine, leucine), (aspartic acid, glutamic acid), (asparagine, glutamine), (serine, threonine), (lysine, arginine), (phenylalanine, tyrosine), and the like.

The amino acid substitutions, deletions, insertions, and/or additions are preferably introduced into regions other than Myb transcription factor activity domains, binding domains that bind to transcription factor binding sites, and other important portions involved in transcription factor activity. Those skilled in the art can appropriately identify such domains by homology analysis with known Myb transcription factors.

It is also known that some proteins with amino acid sequences having high sequence identity to the amino acid sequence of a transcription factor also have similar activity. Considering this fact, another specific example of the Myb transcription factor is the following protein [3]:

[3] a protein having transcription factor activity and having an amino acid sequence that has at least 80% sequence identity to the amino acid sequence of SEQ ID NO:26, 28, or 30.

For maintenance of transcription factor activity, the sequence identity to the amino acid sequence of SEQ ID NO:26, 28, or 30 is preferably at least 85%, more preferably at least 90%, still more preferably at least 95%, particularly preferably at least 98%, and most preferably at least 99%.

The sequence identity between amino acid sequences or base sequences may be determined using the algorithm BLAST® [Pro. Natl. Acad. Sci. USA, 90, 5873 (1993)] developed by Karlin and Altschul or FASTA [Methods Enzymol., 183, 63 (1990)].

Whether a protein has transcription factor activity may be determined by conventionally known techniques, such as gel shift assays, or reporter assays using a reporter gene encoding β-galactosidase, luciferase, green fluorescent protein (GFP), or the like.

The Myb transcription factor is preferably any of the following proteins:

[1-1] a protein having the amino acid sequence of SEQ ID NO:26 or 28;

[2-1] a protein having transcription factor activity and having an amino acid sequence containing one or more amino acid substitutions, deletions, insertions and/or additions relative to the amino acid sequence of SEQ ID NO:26 or 28; and

[3-1] a protein having transcription factor activity and having an amino acid sequence that has at least 80% sequence identity to the amino acid sequence of SEQ ID NO:26 or 28.

The Myb transcription factor is more preferably any of the following proteins:

[1-2] a protein having the amino acid sequence of SEQ ID NO:26;

[2-2] a protein having transcription factor activity and having an amino acid sequence containing one or more amino acid substitutions, deletions, insertions and/or additions relative to the amino acid sequence of SEQ ID NO:26; and

[3-2] a protein having transcription factor activity and having an amino acid sequence that has at least 80% sequence identity to the amino acid sequence of SEQ ID NO:26.

(DNA Encoding Myb Transcription Factor)

Moreover, the DNA encoding the Myb transcription factor may be either of the following DNAs:

[1] a DNA having the base sequence of SEQ ID NO:25, 27, or 29; and

[2] a DNA encoding a protein with transcription factor activity and capable of hybridizing under stringent conditions to a DNA having a base sequence complementary to the base sequence of SEQ ID NO:25, 27, or 29.

In this context, the term "hybridizing" means a process in which the DNA hybridizes to a DNA having a particular base sequence or a part of the DNA. Thus, the DNA having a particular base sequence or part of the DNA may have a base sequence long enough to be usable as a probe in Northern or Southern blot analysis or as an oligonucleotide primer in polymerase chain reaction (PCR) analysis. The DNA used as a probe may have a length of at least 100 bases, preferably at least 200 bases, and more preferably at least 500 bases although it may be a DNA of at least 10 bases, and preferably of at least 15 bases in length.

Techniques to perform DNA hybridization experiments are well known. The hybridization conditions under which experiments are performed may be determined according to, for example, Molecular Cloning, 2nd ed. and 3rd ed. (2001); Methods for General and Molecular Bacteriology, ASM Press (1994); Immunology methods manual, Academic press (Molecular); and many other standard textbooks.

The stringent conditions may include, for example, an overnight incubation at 42° C. of a DNA-immobilized filter and a DNA probe in a solution containing 50% formamide, 5×SSC (750 mM sodium chloride and 75 mM sodium citrate), 50 mM sodium phosphate (pH 7.6), 5×Denhardt's solution, 10% dextran sulfate, and 20 µg/l denatured salmon sperm DNA, followed by washing the filter for example in a 0.2×SSC solution at approximately 65° C. Less stringent conditions may also be used. Changes in the stringency may be accomplished through the manipulation of formamide concentration (lower percentages of formamide result in lower stringency), salt concentrations or temperature. For example, low stringent conditions include an overnight incubation at 37° C. in a solution containing 6×SSCE (20×SSCE: 3 mol/l sodium chloride, 0.2 mol/l sodium dihydrogen phosphate, 0.02 mol/l EDTA, pH 7.4), 0.5% SDS, 30% formamide, and 100 µg/l denatured salmon sperm DNA, followed by washing in a 1×SSC solution containing 0.1% SDS at 50° C. Moreover, to achieve even lower stringency, washes performed following hybridization may be done at higher salt concentrations (e.g. 5×SSC) in the above-mentioned low stringent conditions.

Variations in the above various conditions may be accomplished through the inclusion or substitution of blocking reagents used to suppress background in hybridization experiments. The inclusion of blocking reagents may require modification of the hybridization conditions for compatibility.

The DNA capable of hybridization under stringent conditions as described above may be a DNA having a base sequence that has at least 80%, preferably at least 90%, more preferably at least 95%, even more preferably at least 98%, and particularly preferably at least 99% sequence identity to the base sequence of SEQ ID NO: 25, 27, or 29 as calculated using a program such as BLAST® or FASTA with the parameters mentioned above.

Whether the DNA capable of hybridizing under stringent conditions to the DNA mentioned above encodes a protein with transcription factor activity may be determined by conventionally known techniques, such as gel shift assays, or reporter assays using a reporter gene encoding β-galactosidase, luciferase, green fluorescent protein (GFP), or the like.

The DNA encoding the Myb transcription factor is preferably either of the following DNAs:

[1-1] a DNA having the base sequence of SEQ ID NO:25 or 27; and

[2-1] a DNA encoding a protein with transcription factor activity and capable of hybridizing under stringent conditions to a DNA having a base sequence complementary to the base sequence of SEQ ID NO:25 or 27.

More preferred is either of the following DNAs:

[1-2] a DNA having the base sequence of SEQ ID NO:25; and

[2-2] a DNA encoding a protein with transcription factor activity and capable of hybridizing under stringent conditions to a DNA having a base sequence complementary to the base sequence of SEQ ID NO:25.

The Myb transcription factor and the DNA encoding the Myb transcription factor may be obtained by site-directed mutagenesis of, for example, the base sequence of SEQ ID NO:25, 27, or 29 (the base sequence of Myb6 from *Arabidopsis thaliana*, the base sequence of Myb3 from *Arabidopsis thaliana*, or the base sequence of EPR1 from *Arabidopsis thaliana*) according to site-directed mutagenesis techniques described in Molecular Cloning, A Laboratory Manual, Second Edition, Cold Spring Harbor Laboratory Press (1989); Current Protocols in Molecular Biology, John Wiley & Sons (1987-1997); Nucleic Acids Research, 10, 6487 (1982); Proc. Natl. Acad. Sci. USA, 79, 6409 (1982); Gene, 34, 315 (1985); Nucleic Acids Research, 13, 4431 (1985); Proc. Natl. Acad. Sci. USA, 82, 488 (1985), etc.

(Transformant)

The gene encoding the Myb transcription factor can be introduced into a host to create an organism (transformant) that is transformed to express the Myb transcription factor. Then this transformant expresses the Myb transcription factor, which regulates (enhances) the expression of hydroxymethylglutaryl-CoA reductase. Consequently, the rate-limiting step of IPP biosynthesis in the MVA pathway is enhanced, whereby the polyisoprenoid biosynthesis pathway is suitably enhanced. Thus, it is possible to suitably increase polyisoprenoid production in the transformant.

The following briefly describes how to prepare an organism (transformant) that is transformed to express an Myb transcription factor. The brief description below mainly focuses on how to prepare a transformant that is transformed to express the above-mentioned Myb transcription factor. Once an Myb transcription factor-encoding gene to be introduced has been determined, such a transformant can be prepared by conventionally known methods.

Specifically, for example, a DNA containing the base sequence of SEQ ID NO:25, 27, or 29 (the base sequence of Myb6 from *Arabidopsis thaliana*, the base sequence of Myb3 from *Arabidopsis thaliana*, or the base sequence of EPR1 from *Arabidopsis thaliana*) is inserted downstream of a promoter of an appropriate expression vector using appropriate restriction enzymes and the like to prepare a recombinant DNA, which is then introduced into host cells compatible with the expression vector to obtain a transformant.

Although the above description relates to the cases where a DNA containing the base sequence of SEQ ID NO: 25, 27, or 29 (the base sequence of Myb6 from *Arabidopsis thali-* ana, the base sequence of Myb3 from *Arabidopsis thaliana*, or the base sequence of EPR1 from *Arabidopsis thaliana*) is used, DNAs encoding other Myb transcription factors from *Arabidopsis thaliana* or Myb transcription factors from organisms other than *Arabidopsis thaliana* may be used. In such cases, screening may be performed by known techniques, such as using a part of the base sequence of SEQ ID NO:25 as a probe, to identify and isolate such DNAs encoding the Myb transcription factors. The method for isolating a DNA molecule of interest using a DNA molecule as a probe is described in, for example, Molecular Cloning, 2nd edition, Cold Spring Harbor Press (1989). DNAs obtained by mutagenesis of the DNAs mentioned above may also be used.

Any of microorganisms, yeasts, animal cells, insect cells, plant cells, and the like can be used as the host (host cells), as long as they are capable of expressing a gene of interest. Since the only organisms currently known to biosynthesize polyisoprenoids are plants (isoprenoid-producing plants), the host is preferably a plant (an isoprenoid-producing plant), and the host cells are preferably plant cells (cells of an isoprenoid-producing plant). Note that if a future advance in technology allows cells other than plant cells to biosynthesize polyisoprenoids, the gene encoding the Myb transcription factor can be suitably introduced into such cells.

The isoprenoid-producing plant is not particularly limited, as long as it is capable of producing an isoprenoid. Examples include plants of the genus *Hevea*, such as *Hevea brasiliensis*; plants of the genus *Sonchus*, such as *Sonchus oleraceus, Sonchus asper*, and *Sonchus brachyotus*; plants of the genus *Solidago*, such as *Solidago altissima, Solidago virgaurea* subsp. *asiatica, Solidago virgaurea* subsp. *leipcarpa, Solidago virgaurea* subsp. *leipcarpa* f. *paludosa, Solidago virgaurea* subsp. *gigantea*, and *Solidago gigantea* Ait. var. *leiophylla* Fernald; plants of the genus *Helianthus*, such as *Helianthus annuus, Helianthus argophyllus, Helianthus atrorubens, Helianthus debilis, Helianthus decapetalus*, and *Helianthus giganteus*; plants of the genus *Taraxacum*, such as *Taraxacum, Taraxacum venustum* H. Koidz, *Taraxacum hondoense* Nakai, *Taraxacum platycarpum* Dahlst, *Taraxacum japonicum, Taraxacum officinale* Weber, and *Taraxacum koksaghyz*; plants of the genus *Ficus*, such as *Ficus carica, Ficus elastica, Ficus pumila* L., *Ficus erecta* Thumb., *Ficus ampelas* Burm. f., *Ficus benguetensis* Merr., *Ficus irisana* Elm., *Ficus microcarpa* L. f., *Ficus septica* Burm. f., and *Ficus benghalensis*; plants of the genus *Parthenium*, such as *Parthenium argentatum, Parthenium hysterophorus*, and *Parthenium hysterophorus*; and *Lactuca serriola* and *Ficus benghalensis*. In particular, the isoprenoid-producing plant is preferably at least one selected from the group consisting of plants of the genera *Hevea, Sonchus, Taraxacum*, and *Parhenium*, and more preferably at least one selected from the group consisting of *Hevea brasiliensis, Sonchus oleraceus, Parthenium argentatum*, and *Taraxacum koksaghyz*.

Examples of expression vectors that can be used include vectors that are capable of autonomous replication in the host cells or of being incorporated into a chromosome thereof and contain a promoter at a position that permits transcription of the recombinant DNA.

In the case where plant cells are used as host cells, a pBI vector, a pUC vector, a Ti plasmid or tobacco mosaic virus vector, for example, may be used as an expression vector.

Any promoter that functions in plant cells can be used. Examples include cauliflower mosaic virus (CaMV) 35S promoter, rice actin-1 promoter, nopaline synthase gene promoter, tobacco mosaic virus 35S promoter, and rice actin gene promoter.

Preferred are expression vectors with promoters that are specifically expressed in tissues in which isoprenoid compounds are biosynthesized, such as laticifers. If the promoters are specifically expressed in tissues in which polyisoprenoids are biosynthesized, retardation of plant growth and other adverse effects can be prevented.

The recombinant vector can be introduced by any method that allows the DNA to be introduced into plant cells. Examples include methods using *Agrobacterium* (JP S59-140885 A, JP S60-70080 A, WO94/00977), electroporation (JP S60-251887 A), and methods using a particle gun (gene gun) (JP 2606856 B, JP 2517813 B).

Transformants (transgenic plant cells) into which has been introduced a gene encoding an Myb transcription factor can be prepared by these methods or the like.

The second aspect of the present invention provides an isoprenoid-producing plant into which has been introduced a gene encoding an Myb transcription factor. The isoprenoid-producing plant is not particularly limited, as long as it is an isoprenoid-producing plant containing the transgenic plant cells. It is intended to include, for example, in addition to transgenic plant cells prepared by the above-described methods, all of their progeny or clones and even progeny plants obtained by passaging these cells. Once transgenic plant cells into which the DNA or vector has been introduced in the genome are obtained, progeny or clones can be obtained from the transgenic plant cells by sexual or asexual reproduction, tissue culture, cell culture, cell fusion, or the like. Further, the transgenic plant cells, or their progeny or clones may be used to obtain reproductive materials (e.g. seeds, fruits, cuttings, stem tubers, root tubers, shoots, adventitious buds, adventitious embryos, calluses, protoplasts), which can then be used to produce the isoprenoid-producing plant on a large scale.

Techniques to regenerate plants from transgenic plant cells are already known; for example, Doi et al. disclose techniques for eucalyptus (JP 2000-316403 A), Fujimura et al. disclose techniques for rice (Fujimura et al., (1995), Plant Tissue Culture Lett., vol. 2: p 74-), Shillito et al. disclose techniques for corn (Shillito et al., (1989), Bio/Technology, vol. 7: p 581-), Visser et al. disclose techniques for potato (Visser et al., (1989), Theor. Appl. Genet., vol. 78: p 589-), and Akama et al. disclose techniques for *Arabidopsis thaliana* (Akama et al., (1992), Plant Cell Rep., vol. 12: p 7-). Those skilled in the art can regenerate plants from transgenic plant cells according to these documents.

Whether a target transcription factor gene is expressed in a regenerated plant may be determined by well-known methods. For example, western blot analysis may be used to assess the expression of a target transcription factor.

Seeds can be obtained from the transgenic plant, for example, as follows: the transgenic plant is rooted in an appropriate medium and then transplanted to water-containing soil in a pot, and grown under proper cultivation conditions so as to finally produce seeds, which are then collected. Further, plants can be grown from seeds, for example, as follows: seeds obtained from the transgenic plant as described above are sown in water-containing soil, and grown under proper cultivation conditions into plants.

According to the second aspect of the present invention, the isoprenoid-producing plant into which has been introduced a gene encoding an Myb transcription factor can be used in the production of polyisoprenoids to increase polyisoprenoid production. Specifically, polyisoprenoids can be produced by culturing transgenic plant cells prepared as described above, calluses obtained from such transgenic plant cells, cells redifferentiated from such calluses, or the like in an appropriate medium, or by growing transgenic plants regenerated from the transgenic plant cells, plants grown from seeds collected from such transgenic plants, or the like under proper cultivation conditions. In the isoprenoid-producing plant of the second aspect of the present invention, the rate-limiting step of IPP biosynthesis in the MVA pathway is enhanced by the Myb transcription factor introduced therein, and therefore the polyisoprenoid biosynthesis pathway is suitably enhanced. Thus, it is possible to suitably increase polyisoprenoid production.

The term "polyisoprenoid" as used herein is a generic term used to refer to polymers having isoprene ($C_5H_8$) units. Examples of polyisoprenoids include polymers such as monoterpenes ($C_{10}$), sesquiterpenes ($C_{15}$), diterpenes ($C_{20}$), sesterterpenes ($C_{25}$), triterpenes ($C_{30}$), tetraterpenes ($C_{40}$), and natural rubber.

As described above, in the second aspect of the present invention, which enables to regulate (enhance) the expression of hydroxymethylglutaryl-CoA reductase by an Myb transcription factor, the rate-limiting step of IPP biosynthesis in the MVA pathway is enhanced, whereby the polyisoprenoid biosynthesis pathway is suitably enhanced. Thus, it is possible to suitably increase polyisoprenoid production in the transformant.

Moreover, in the isoprenoid-producing plant of the second aspect of the present invention into which has been introduced a gene encoding an Myb transcription factor, the rate-limiting step of IPP biosynthesis in the MVA pathway is enhanced by the Myb transcription factor introduced therein, and therefore the polyisoprenoid biosynthesis pathway is suitably enhanced. Accordingly, the use of the isoprenoid-producing plant in the production of polyisoprenoids suitably increases polyisoprenoid production.

Thus, the method of the second aspect of the present invention, the isoprenoid-producing plant of the second aspect of the present invention, and the method for producing a polyisoprenoid of the second aspect of the present invention, all of which are capable of increasing polyisoprenoid production, can be effective for natural rubber source depletion that is of concern.

(Third Aspect of the Present Invention)

The present inventors have studied various ways to enhance the polyisoprenoid biosynthesis pathway. FIG. 1 shows a part of the polyisoprenoid biosynthesis pathway. There are two known pathways, the mevalonic acid (MVA) pathway (cytosol MVA pathway as shown in FIG. 1) and the MEP pathway (plastidial DXP pathway as shown in FIG. 1), for biosynthesis of isopentenyl diphosphate (IPP), which is an important member of the polyisoprenoid biosynthesis pathway.

The present inventors focused on the MVA pathway which is a common pathway that supplies IPP in rubber latex synthesis, and selected, from various proteins involved in the polyisoprenoid biosynthesis pathway, some proteins that are expected to have important roles in view of enhancing the pathway enclosed in the dotted line in FIG. 1. Further, they found out that, among these proteins, hydroxymethylglutaryl-CoA reductase (HMG-CoA reductase) is a rate-limiting factor in the MVA pathway.

In order to regulate the expression of HMG-CoA reductase, the present inventors then sought a transcription factor capable of regulating the expression of HMG-CoA reductase. Specifically, a DNA fragment from leaves of *Hevea brasiliensis* which contains a gene encoding HMG-CoA reductase (the amino acid sequence of HMG-CoA reductase is set forth in the sequence listing as SEQ ID NO:47) (the base sequence of the gene is set forth in the sequence listing as SEQ ID NO:46) and its promoter region was cloned (see EXAMPLES for details). The base sequence of the resulting DNA fragment was analyzed to reveal the base sequence of the promoter region of the gene encoding HMG-CoA reductase.

Additionally, the revealed base sequence of the promoter region was analyzed using a plant promoter database (a database of plant cis-acting regulatory DNA elements (PLACE)). The analysis revealed that the sequence contains a lot of basic-helix-loop-helix (bHLH) transcription factor binding (recognition) sites (CANNTG).

These results strongly suggest that bHLH transcription factors are transcription factors capable of regulating the expression of HMG-CoA reductase, or in other words, transcription factors that enhance the rate-limiting step of IPP biosynthesis in the MVA pathway and can thereby suitably regulate the polyisoprenoid biosynthesis pathway. Then, a validation test using yeast cells was performed to confirm that the expression of HMG-CoA reductase is enhanced by the use of Myc2 (the base sequence and the amino acid sequence of Myc2 from *Arabidopsis thaliana* are set forth in the sequence listing as SEQ ID NOs:40 and 41, respectively), ILR3 (the base sequence and the amino acid sequence of ILR3 from *Arabidopsis thaliana* are set forth in the sequence listing as SEQ ID NOs:42 and 43, respectively), or HFR1 (the base sequence and the amino acid sequence of HFR1 from *Arabidopsis thaliana* are set forth in the sequence listing as SEQ ID NOs:44 and 45, respectively) among bHLH transcription factors.

As described above, the present inventors have found that bHLH transcription factors can suitably enhance the expression of HMG-CoA reductase, and thus enhance the rate-limiting step of IPP biosynthesis in the MVA pathway and can thereby suitably enhance the polyisoprenoid biosynthesis pathway. Another finding is that since the bHLH transcription factors enhance the rate-limiting step of IPP biosynthesis in the MVA pathway and can thereby suitably enhance the polyisoprenoid biosynthesis pathway, an isoprenoid-producing plant into which has been introduced a gene encoding such a bHLH transcription factor can be used in the production of polyisoprenoids to increase polyisoprenoid production.

As used herein, "hydroxymethylglutaryl-CoA reductase (HMG-CoA reductase)" is a rate-limiting enzyme of the mevalonic acid pathway and is intended to include both hydroxymethylglutaryl-CoA reductase (NADPH) (EC 1.1.1.34) and hydroxymethylglutaryl-CoA reductase (EC 1.1.1.88).

The method of the third aspect of the present invention is a method for regulating the expression of hydroxymethylglutaryl-CoA reductase by a bHLH transcription factor.

The bHLH transcription factor is not particularly limited, as long as it is a transcription factor having a basic helix-loop-helix motif as a structural feature. Examples include Myc2 (the base sequence and the amino acid sequence of Myc2 from *Arabidopsis thaliana* are set forth in the sequence listing as SEQ ID NOs:40 and 41, respectively), ILR3 (the base sequence and the amino acid sequence of ILR3 from *Arabidopsis thaliana* are set forth in the sequence listing as SEQ ID NOs:42 and 43, respectively), and HFR1 (the base sequence and the amino acid sequence of HFR1 from *Arabidopsis thaliana* are set forth in the sequence listing as SEQ ID NOs:44 and 45, respectively).

The term "transcription factor" as used herein refers to a protein having an activity of increasing or decreasing (preferably increasing) the rate of transcription of a gene or genes.

The origin of the bHLH transcaription factor is not particularly limited, but the bHLH transcription factor is preferably a transcription factor from *Hevea brasiliensis*, *Sonchus oleraceus*, *Parthenium argentatum*, *Taraxacum koksaghyz*, or *Arabidopsis thaliana*.

(Amino Acid Sequence of bHLH Transcription Factor)

The following protein [1] is a specific example of the bHLH transcription factor:

[1] a protein having the amino acid sequence of SEQ ID NO:41, 43, or 45.

Moreover, it is known that some transcription factors have transcription factor activity even when one or more amino acid substitutions, deletions, insertions, or additions are introduced into their original amino acid sequences. Considering this fact, another specific example of the bHLH transcription factor is the following protein [2]:

[2] a protein having transcription factor activity and having an amino acid sequence containing one or more amino acid substitutions, deletions, insertions and/or additions relative to the amino acid sequence of SEQ ID NO:41, 43, or 45.

The term "transcription factor activity" as used herein refers to an activity of increasing or decreasing (preferably increasing) the rate of transcription of a gene encoding hydroxymethylglutaryl-CoA reductase.

For maintenance of transcription factor activity, the number of amino acid substitutions, deletions, insertions, and/or additions relative to the amino acid sequence of SEQ ID NO:41 is preferably 1 or more, more preferably 1 to 119, still more preferably 1 to 89, particularly preferably 1 to 60, most preferably 1 to 30, even most preferably 1 to 12, and still even most preferably 1 to 6.

For maintenance of transcription factor activity, the number of amino acid substitutions, deletions, insertions, and/or additions relative to the amino acid sequence of SEQ ID NO:43 is preferably 1 or more, more preferably 1 to 47, still more preferably 1 to 35, particularly preferably 1 to 23, most preferably 1 to 12, even most preferably 1 to 5, and still even most preferably 1 or 2.

For maintenance of transcription factor activity, the number of amino acid substitutions, deletions, insertions, and/or additions relative to the amino acid sequence of SEQ ID NO:45 is preferably 1 or more, more preferably 1 to 58, still more preferably 1 to 44, particularly preferably 1 to 29, most preferably 1 to 15, even most preferably 1 to 6, and still even most preferably 1 to 3.

Among other amino acid substitutions, conservative substitutions are preferred. Specific examples include substitutions within each of the following groups in the parentheses: (glycine, alanine), (valine, isoleucine, leucine), (aspartic acid, glutamic acid), (asparagine, glutamine), (serine, threonine), (lysine, arginine), (phenylalanine, tyrosine), and the like.

The amino acid substitutions, deletions, insertions, and/or additions are preferably introduced into regions other than bHLH transcription factor activity domains, binding domains that bind to transcription factor binding sites, and other important portions involved in transcription factor activity. Those skilled in the art can appropriately identify such domains by homology analysis with known bHLH transcription factors.

It is also known that some proteins with amino acid sequences having high sequence identity to the amino acid sequence of a transcription factor also have similar activity. Considering this fact, another specific example of the bHLH transcription factor is the following protein [3]:

[3] a protein having transcription factor activity and having an amino acid sequence that has at least 80% sequence identity to the amino acid sequence of SEQ ID NO:41, 43, or 45.

For maintenance of transcription factor activity, the sequence identity to the amino acid sequence of SEQ ID NO:41, 43, or 45 is preferably at least 85%, more preferably at least 90%, still more preferably at least 95%, particularly preferably at least 98%, and most preferably at least 99%.

The sequence identity between amino acid sequences or base sequences may be determined using the algorithm BLAST® [Pro. Natl. Acad. Sci. USA, 90, 5873 (1993)] developed by Karlin and Altschul or FASTA [Methods Enzymol., 183, 63 (1990)].

Whether a protein has transcription factor activity may be determined by conventionally known techniques, such as gel shift assays, or reporter assays using a reporter gene encoding β-galactosidase, luciferase, green fluorescent protein (GFP), or the like.

The bHLH transcription factor is preferably any of the following proteins:

[1-1] a protein having the amino acid sequence of SEQ ID NO:41 or 43;

[2-1] a protein having transcription factor activity and having an amino acid sequence containing one or more amino acid substitutions, deletions, insertions and/or additions relative to the amino acid sequence of SEQ ID NO:41 or 43; and

[3-1] a protein having transcription factor activity and having an amino acid sequence that has at least 80% sequence identity to the amino acid sequence of SEQ ID NO:41 or 43.

The bHLH transcription factor is more preferably any of the following proteins:

[1-2] a protein having the amino acid sequence of SEQ ID NO:41;

[2-2] a protein having transcription factor activity and having an amino acid sequence containing one or more amino acid substitutions, deletions, insertions and/or additions relative to the amino acid sequence of SEQ ID NO:41; and

[3-2] a protein having transcription factor activity and having an amino acid sequence that has at least 80% sequence identity to the amino acid sequence of SEQ ID NO:41.

(DNA Encoding bHLH Transcription Factor)

Moreover, the DNA encoding the bHLH transcription factor may be either of the following DNAs:

[1] a DNA having the base sequence of SEQ ID NO:40, 42, or 44; and

[2] a DNA encoding a protein with transcription factor activity and capable of hybridizing under stringent conditions to a DNA having a base sequence complementary to the base sequence of SEQ ID NO:40, 42, or 44.

In this context, the term "hybridizing" means a process in which the DNA hybridizes to a DNA having a particular base sequence or a part of the DNA. Thus, the DNA having a particular base sequence or part of the DNA may have a base sequence long enough to be usable as a probe in Northern or Southern blot analysis or as an oligonucleotide primer in polymerase chain reaction (PCR) analysis. The DNA used as a probe may have a length of at least 100 bases, preferably at least 200 bases, and more preferably at least 500 bases although it may be a DNA of at least 10 bases, and preferably of at least 15 bases in length.

Techniques to perform DNA hybridization experiments are well known. The hybridization conditions under which experiments are performed may be determined according to, for example, Molecular Cloning, 2nd ed. and 3rd ed. (2001); Methods for General and Molecular Bacteriology, ASM Press (1994); Immunology methods manual, Academic press (Molecular); and many other standard textbooks.

The stringent conditions may include, for example, an overnight incubation at 42° C. of a DNA-immobilized filter and a DNA probe in a solution containing 50% formamide, 5×SSC (750 mM sodium chloride and 75 mM sodium citrate), 50 mM sodium phosphate (pH 7.6), 5×Denhardt's solution, 10% dextran sulfate, and 20 µg/l denatured salmon sperm DNA, followed by washing the filter for example in a 0.2×SSC solution at approximately 65° C. Less stringent conditions may also be used. Changes in the stringency may be accomplished through the manipulation of formamide concentration (lower percentages of formamide result in lower stringency), salt concentrations or temperature. For example, low stringent conditions include an overnight incubation at 37° C. in a solution containing 6×SSCE (20×SSCE: 3 mol/l sodium chloride, 0.2 mol/l sodium dihydrogen phosphate, 0.02 mol/l EDTA, pH 7.4), 0.5% SDS, 30% formamide, and 100 µg/l denatured salmon sperm DNA, followed by washing in a 1×SSC solution containing 0.1% SDS at 50° C. Moreover, to achieve even lower stringency, washes performed following hybridization may be done at higher salt concentrations (e.g. 5×SSC) in the above-mentioned low stringent conditions.

Variations in the above various conditions may be accomplished through the inclusion or substitution of blocking reagents used to suppress background in hybridization experiments. The inclusion of blocking reagents may require modification of the hybridization conditions for compatibility.

The DNA capable of hybridization under stringent conditions as described above may be a DNA having a base sequence that has at least 80%, preferably at least 90%, more preferably at least 95%, even more preferably at least 98%, and particularly preferably at least 99% sequence identity to the base sequence of SEQ ID NO:40, 42, or 44 as calculated using a program such as BLAST® or FASTA with the parameters mentioned above.

Whether the DNA capable of hybridizing under stringent conditions to the DNA mentioned above encodes a protein with transcription factor activity may be determined by conventionally known techniques, such as gel shift assays, or reporter assays using a reporter gene encoding β-galactosidase, luciferase, green fluorescent protein (GFP), or the like.

The DNA encoding the bHLH transcription factor is preferably either of the following DNAs:

[1-1] a DNA having the base sequence of SEQ ID NO:40 or 42; and

[2-1] a DNA encoding a protein with transcription factor activity and capable of hybridizing under stringent conditions to a DNA having a base sequence complementary to the base sequence of SEQ ID NO:40 or 42.

More preferred is either of the following DNAs:

[1-2] a DNA having the base sequence of SEQ ID NO:40; and

[2-2] a DNA encoding a protein with transcription factor activity and capable of hybridizing under stringent conditions to a DNA having a base sequence complementary to the base sequence of SEQ ID NO:40.

The bHLH transcription factor and the DNA encoding the bHLH transcription factor may be obtained by site-directed mutagenesis of, for example, the base sequence of SEQ ID NO:40, 42, or 44 (the base sequence of Myc2 from *Arabidopsis thaliana*, the base sequence of ILR3 from *Arabidopsis thaliana*, or the base sequence of HFR1 from *Arabidopsis thaliana*) according to site-directed mutagenesis techniques described in Molecular Cloning, A Laboratory Manual, Second Edition, Cold Spring Harbor Laboratory Press (1989); Current Protocols in Molecular Biology, John Wiley & Sons (1987-1997); Nucleic Acids Research, 10, 6487 (1982); Proc. Natl. Acad. Sci. USA, 79, 6409 (1982); Gene, 34, 315 (1985); Nucleic Acids Research, 13, 4431 (1985); Proc. Natl. Acad. Sci. USA, 82, 488 (1985), etc.

(Transformant)

The gene encoding the bHLH transcription factor can be introduced into a host to create an organism (transformant) that is transformed to express the bHLH transcription factor. Then this transformant expresses the bHLH transcription factor, which regulates (enhances) the expression of hydroxymethylglutaryl-CoA reductase. Consequently, the rate-limiting step of IPP biosynthesis in the MVA pathway is enhanced, whereby the polyisoprenoid biosynthesis pathway is suitably enhanced. Thus, it is possible to suitably increase polyisoprenoid production in the transformant.

The following briefly describes how to prepare an organism (transformant) that is transformed to express a bHLH transcription factor. The brief description below mainly focuses on how to prepare a transformant that is transformed to express the above-mentioned bHLH transcription factor. Once a bHLH transcription factor-encoding gene to be introduced has been determined, such a transformant can be prepared by conventionally known methods.

Specifically, for example, a DNA containing the base sequence of SEQ ID NO:40, 42, or 44 (the base sequence of Myc2 from *Arabidopsis thaliana*, the base sequence of ILR3 from *Arabidopsis thaliana*, or the base sequence of HFR1 from *Arabidopsis thaliana*) is inserted downstream of a promoter of an appropriate expression vector using appropriate restriction enzymes and the like to prepare a recombinant DNA, which is then introduced into host cells compatible with the expression vector to obtain a transformant.

Although the above description relates to the cases where a DNA containing the base sequence of SEQ ID NO:40, 42, or 44 (the base sequence of Myc2 from *Arabidopsis thaliana*, the base sequence of ILR3 from *Arabidopsis thaliana*, or the base sequence of HFR1 from *Arabidopsis thaliana*) is used, DNAs encoding other bHLH transcription factors from *Arabidopsis thaliana* or bHLH transcription factors from organisms other than *Arabidopsis thaliana* may be used. In such cases, screening may be performed by known techniques, such as using a part of the base sequence of SEQ ID NO:40 as a probe, to identify and isolate such DNAs encoding the bHLH transcription factors. The method for isolating a DNA molecule of interest using a DNA molecule as a probe is described in, for example, Molecular Cloning, 2nd edition, Cold Spring Harbor Press (1989). DNAs obtained by mutagenesis of the DNAs mentioned above may also be used.

Any of microorganisms, yeasts, animal cells, insect cells, plant cells, and the like can be used as the host (host cells), as long as they are capable of expressing a gene of interest. Since the only organisms currently known to biosynthesize polyisoprenoids are plants (isoprenoid-producing plants), the host is preferably a plant (an isoprenoid-producing plant), and the host cells are preferably plant cells (cells of an isoprenoid-producing plant). Note that if a future advance in technology allows cells other than plant cells to biosynthesize polyisoprenoids, the gene encoding the bHLH transcription factor can be suitably introduced into such cells.

The isoprenoid-producing plant is not particularly limited, as long as it is capable of producing an isoprenoid. Examples include plants of the genus *Hevea*, such as *Hevea brasiliensis*; plants of the genus *Sonchus*, such as *Sonchus oleraceus, Sonchus asper*, and *Sonchus brachyotus*; plants of the genus *Solidago*, such as *Solidago altissima, Solidago virgaurea* subsp. *asiatica, Solidago virgaurea* subsp. *leipcarpa, Solidago virgaurea* subsp. *leipcarpa* f. *paludosa, Solidago virgaurea* subsp. *gigantea*, and *Solidago gigantea* Ait. var. *leiophylla* Fernald; plants of the genus *Helianthus*, such as *Helianthus annuus, Helianthus argophyllus, Helianthus atrorubens, Helianthus debilis, Helianthus decapetalus*, and *Helianthus giganteus*; plants of the genus *Taraxacum*, such as *Taraxacum, Taraxacum venustum* H. Koidz, *Taraxacum hondoense* Nakai, *Taraxacum platycarpum* Dahlst, *Taraxacum japonicum, Taraxacum officinale* Weber, and *Taraxacum koksaghyz*; plants of the genus *Ficus*, such as *Ficus carica, Ficus elastica, Ficus pumila* L., *Ficus erecta* Thumb., *Ficus ampelas* Burm. f., *Ficus benguetensis* Merr., *Ficus irisana* Elm., *Ficus microcarpa* L.f., *Ficus septica* Burm. f., and *Ficus benghalensis*; plants of the genus *Parthenium*, such as *Parthenium argentatum, Parthenium hysterophorus*, and *Parthenium hysterophorus*; and *Lactuca serriola* and *Ficus benghalensis*. In particular, the isoprenoid-producing plant is preferably at least one selected from the group consisting of plants of the genera *Hevea, Sonchus, Taraxacum*, and *Parhenium*, and more preferably at least one selected from the group consisting of *Hevea brasiliensis, Sonchus oleraceus, Parthenium argentatum*, and *Taraxacum koksaghyz*.

Examples of expression vectors that can be used include vectors that are capable of autonomous replication in the host cells or of being incorporated into a chromosome thereof and contain a promoter at a position that permits transcription of the recombinant DNA.

In the case where plant cells are used as host cells, a pBI vector, a pUC vector, a Ti plasmid or tobacco mosaic virus vector, for example, may be used as an expression vector.

Any promoter that functions in plant cells can be used. Examples include cauliflower mosaic virus (CaMV) 35S promoter, rice actin-1 promoter, nopaline synthase gene promoter, tobacco mosaic virus 35S promoter, and rice actin gene promoter.

Preferred are expression vectors with promoters that are specifically expressed in tissues in which isoprenoid compounds are biosynthesized, such as laticifers. If the promoters are specifically expressed in tissues in which polyisoprenoids are biosynthesized, retardation of plant growth and other adverse effects can be prevented.

The recombinant vector can be introduced by any method that allows the DNA to be introduced into plant cells. Examples include methods using *Agrobacterium* (JP S59-140885 A, JP S60-70080 A, WO94/00977), electroporation (JP S60-251887 A), and methods using a particle gun (gene gun) (JP 2606856 B, JP 2517813 B).

Transformants (transgenic plant cells) into which has been introduced a gene encoding a bHLH transcription factor can be prepared by these methods or the like.

The third aspect of the present invention provides an isoprenoid-producing plant into which has been introduced a gene encoding a bHLH transcription factor. The isoprenoid-producing plant is not particularly limited, as long as it is an isoprenoid-producing plant containing the transgenic plant cells. It is intended to include, for example, in addition to transgenic plant cells prepared by the above-described methods, all of their progeny or clones and even progeny plants obtained by passaging these cells. Once transgenic plant cells into which the DNA or vector has been introduced in the genome are obtained, progeny or clones can be obtained from the transgenic plant cells by sexual or asexual reproduction, tissue culture, cell culture, cell fusion, or the like. Further, the transgenic plant cells, or their progeny or clones may be used to obtain reproductive materials (e.g. seeds, fruits, cuttings, stem tubers, root tubers, shoots, adventitious buds, adventitious embryos, calluses, protoplasts), which can then be used to produce the isoprenoid-producing plant on a large scale.

Techniques to regenerate plants from transgenic plant cells are already known; for example, Doi et al. disclose techniques for eucalyptus (JP 2000-316403 A), Fujimura et al. disclose techniques for rice (Fujimura et al., (1995), Plant Tissue Culture Lett., vol. 2: p 74-), Shillito et al. disclose techniques for corn (Shillito et al., (1989), Bio/Technology, vol. 7: p 581-), Visser et al. disclose techniques for potato (Visser et al., (1989), Theor. Appl. Genet., vol. 78: p 589-), and Akama et al. disclose techniques for *Arabidopsis thaliana* (Akama et al., (1992), Plant Cell Rep., vol. 12: p 7-). Those skilled in the art can regenerate plants from transgenic plant cells according to these documents.

Whether a target transcription factor gene is expressed in a regenerated plant may be determined by well-known methods. For example, western blot analysis may be used to assess the expression of a target transcription factor.

Seeds can be obtained from the transgenic plant, for example, as follows: the transgenic plant is rooted in an appropriate medium and then transplanted to water-containing soil in a pot, and grown under proper cultivation conditions so as to finally produce seeds, which are then collected. Further, plants can be grown from seeds, for example, as follows: seeds obtained from the transgenic plant as described above are sown in water-containing soil, and grown under proper cultivation conditions into plants.

According to the third aspect of the present invention, the isoprenoid-producing plant into which has been introduced a gene encoding a bHLH transcription factor can be used in the production of polyisoprenoids to increase polyisoprenoid production. Specifically, polyisoprenoids can be produced by culturing transgenic plant cells prepared as described above, calluses obtained from such transgenic plant cells, cells redifferentiated from such calluses, or the like in an appropriate medium, or by growing transgenic plants regenerated from the transgenic plant cells, plants grown from seeds collected from such transgenic plants, or the like under proper cultivation conditions. In the isoprenoid-producing plant of the third aspect of the present invention, the rate-limiting step of IPP biosynthesis in the MVA pathway is enhanced by the bHLH transcription factor introduced therein, and therefore the polyisoprenoid biosynthesis pathway is suitably enhanced. Thus, it is possible to suitably increase polyisoprenoid production.

The term "polyisoprenoid" as used herein is a generic term used to refer to polymers having isoprene ($C_5H_8$) units. Examples of polyisoprenoids include polymers such as monoterpenes ($C_{10}$), sesquiterpenes ($C_{15}$), diterpenes ($C_{20}$), sesterterpenes ($C_{25}$), triterpenes ($C_{30}$), tetraterpenes ($C_{40}$), and natural rubber.

As described above, in the third aspect of the present invention, which enables to regulate (enhance) the expression of hydroxymethylglutaryl-CoA reductase by a bHLH transcription factor, the rate-limiting step of IPP biosynthesis in the MVA pathway is enhanced, whereby the polyisoprenoid biosynthesis pathway is suitably enhanced. Thus, it is possible to suitably increase polyisoprenoid production in the transformant.

Moreover, in the isoprenoid-producing plant of the third aspect of the present invention into which has been introduced a gene encoding a bHLH transcription factor, the rate-limiting step of IPP biosynthesis in the MVA pathway is enhanced by the bHLH transcription factor introduced therein, and therefore the polyisoprenoid biosynthesis pathway is suitably enhanced. Accordingly, the use of the isoprenoid-producing plant in the production of polyisoprenoids suitably increases polyisoprenoid production.

Thus, the method of the third aspect of the present invention, the isoprenoid-producing plant of the third aspect of the present invention, and the method for producing a polyisoprenoid of the third aspect of the present invention, all of which are capable of increasing polyisoprenoid production, can be effective for natural rubber source depletion that is of concern.

EXAMPLES

The present invention will be specifically described by reference to examples. The examples are not to be construed as limiting the present invention.
(First Aspect of the Present Invention)
(Preparation of Promoter Sequence)

DNA fragments containing the gene encoding HMG-CoA reductase, IPP isomerase, cis-prenyltransferase, or small rubber particle protein from leaves of *Hevea brasiliensis* (the base sequences of the genes encoding cis-prenyltransferase, HMG-CoA reductase, IPP isomerase, and SRPP are set forth in the sequence listing as SEQ ID NOs:7, 9, 11, and 13, respectively) and its promoter were cloned in the following manner. First, genomic DNA was extracted from leaves of *Hevea brasiliensis*. The extraction was carried out using a commercial genomic DNA extraction kit. The genes with their promoter regions were amplified by TAIL-PCR using random primers shown as Primers 1 to 6 and primers corresponding to the genes.

```
                                       (SEQ ID NO: 15)
Primer 1: 5'-ntcgastwtsgwgtt-3'

(SEQ ID NO: 16)
Primer 2: 5'-ngtcgtswganawgaa-3'

(SEQ ID NO: 17)
Primer 3: 5'-wgtgnagwancanag-3'

(SEQ ID NO: 18)
Primer 4: 5'-sttntastnctntgc-3'

(SEQ ID NO: 19)
Primer 5: 5'-sstggstanatwatwct-3'

(SEQ ID NO: 20)
Primer 6: 5'-agwgnagwancanaga-3'
```

The base sequences of the DNA fragments obtained using the primers were analyzed to obtain the promoter sequences of HMG-CoA reductase, IPP isomerase, cis-prenyltransferase, and small rubber particle protein. The base sequences of the promoter sequences of HMG-CoA reductase, IPP isomerase, cis-prenyltransferase, and small rubber particle protein are shown as SEQ ID NOs:21 to 24, respectively.

The promoter sequences were analyzed using a plant promoter database (a database of plant cis-acting regulatory DNA elements (PLACE)) (www.dna.affrc.go.jp/PLACE/)

The analysis revealed that the sequences contain a lot of Dof transcription factor binding sites, and all the promoter sequences of the four genes analyzed are similarly rich in the DOFCOREZM (AAAG) motif to which Dof transcription factors bind. The number of DOFCOREZM motifs is the highest for HMG-CoA reductase, IPP isomerase, and SRPP, and the third highest for cis-prenyltransferase, among the transcription factor binding motifs found in each case.
(Amplification of Promoter Region)

As the promoter regions of the genes, the following regions were amplified by PCR.
HMG-CoA reductase promoter: −1 to −1500 bp, −1 to −1000 bp, and −1 to −500 bp
IPP isomerase promoter: −1 to −1000 bp, and −1 to −500 bp
Cis-prenyltransferase promoter: −1 to −500 bp
Small rubber particle protein promoter: −1 to −1000 bp, and −1 to −500 bp The PCR products were each cloned into pMD20T (Takara Bio, Inc.) to construct pMD20T-hmgpro (−1500), pMD20T-hmgpro (−1000), pMD20T-hmgpro (−500), pMD20T-ipppro (−1000), pMD20T-ipppro (−500), pMD20T-cptpro (−500), pMD20T-srpppro (−1000), and pMD20T-srpppro (−500). The inserted PCR products were sequenced to confirm that no mutation was introduced.
(Construction of Reporter Sequence-Containing Vector)

The plasmids constructed in (Amplification of promoter region) were restricted with SpeI and any of HindIII, KpnI and BamHI, and the promoter sequence fragments were individually incorporated at a site of pYES3/CT/LacZ from which the T7 promoter region had been removed, that is, immediately upstream of the lacZ reporter gene to construct pYES3-hmgprolacZ (−1500), pYES3-hmgprolacZ (−1000), pYES3-hmgpro (−500), pYES3-ippprolacZ (−1000), pYES3-ippprolacZ (−500), pYES3-cptprolacZ (−500), pYES3-srppprolacZ (−1000), and pYES3-srppprolacZ (−500). Ligation high ver. 2 (TOYOBO) was used for ligation.
(Construction of Vector for Gene Introduction into Yeast Chromosome)

The sequence from the SpeI site to the CYC1 transcription termination signal of each of the plasmids constructed in (Construction of reporter sequence-containing vector) was amplified by PCR, and the resulting fragments were restricted with SalI, SmaI, XbaI or SphI, thereby providing DNA fragments with the promoter sequences each linked to the lacZ gene. In order to allow the obtained DNA fragments to be inserted into a yeast chromosome, the DNA fragments were individually incorporated into pAUR101 DNA (Takara Bio, Inc.) treated with the same restriction enzymes to construct pAUR101-hmgprolacZ (−1500), pAUR101-hmgprolacZ (−1000), pAUR101-hmgpro (−500), pAUR101-ippprolacZ (−1000), pAUR101-ippprolacZ (−500), pAUR101-cptprolacZ (−500), pAUR101-srppprolacZ (−1000), and pAUR101-srppprolacZ (−500). Ligation high ver.2 was used for ligation as above.
(Acquisition of Transcription Factor Gene)

Next, PCR was performed using an *Arabidopsis thaliana* cDNA library as a template. The PCR produced the following three PCR fragments: At5g60850 (Dof5.4) (SEQ ID NO:1), At2g28810 (Dof2.2) (SEQ ID NO:3), and At5g60200 (Dof5.3) (SEQ ID NO:5). The obtained PCR products were each cloned into pMD20T to construct pMD20T-Dof5.4, pMD20T-Dof2.2, and pMD20T-Dof5.3. The inserted PCR products were sequenced to confirm that no mutation was introduced.

(Construction of Transcription Factor Expression Vector)

The plasmids constructed in (Acquisition of transcription factor gene) were restricted with SpeI, BamHI, or EcoRV, and the transcription factor genes were individually incorporated downstream of the TEF1 promoter region of p427TEF (COSMO BIO Co., Ltd.) to construct pTEF-Dof5.4, pTEF-Dof2.2, and pTEF-Dof5.3. Ligation high ver.2 was used for ligation.

(Transformation of Yeast)

The plasmids constructed in (Construction of vector for gene introduction into yeast chromosome) and (Construction of transcription factor expression vector) were introduced into yeast cells (BY4741 strain) by electroporation. Screening for transgenic yeast cells was carried out by culturing the yeast cells on a medium containing the antifungal antibiotics Aureobasidin A (Takara Bio, Inc.) and G418 (Wako Pure Chemical Industries, Ltd.).

(Demonstration of Effect of Transcription Factor)

The transgenic yeast cells were cultured on a medium containing X-gal to assess the expression of lacZ due to transcription factor activity. Specifically, when the lacZ reporter gene, which is linked to the promoter sequence, is expressed, X-gal in the medium is then decomposed to develop a blue color. Based on this mechanism, if the medium turned blue, it was determined that lacZ was expressed due to transcription factor activity. This test was repeated 10 times. Table 1 shows how many times lacZ was expressed due to transcription factor activity.

TABLE 1

| Promoter sequence | Transcription factor | | | Control (No transcription factor) |
| --- | --- | --- | --- | --- |
| | At5g60850 (Dof5.4) | At2g28810 (Dof2.2) | At5g60200 (Dof5.3) | |
| hmg(−1500) | 6 | 4 | 3 | 1 |
| hmg(−1000) | 4 | 3 | 1 | 1 |
| hmg(−500) | 3 | 1 | 1 | 0 |
| ipp(−1000) | 6 | 3 | 4 | 0 |
| ipp(−500) | 4 | 2 | 3 | 0 |
| cpt(−500) | 3 | 2 | 1 | 0 |
| srpp(−1000) | 8 | 5 | 4 | 2 |
| srpp(−500) | 5 | 3 | 2 | 1 |

Number of yeast cells that exhibited reporter gene activity (N = 10)

Table 1 shows that the use of At5g60850 (Dof5.4) (SEQ ID NOs: 1 and 2), At2g28810 (Dof2.2) (SEQ ID NOs: 3 and 4), or At5g60200 (Dof5.3) (SEQ ID NOs: 5 and 6), particularly At5g60850 (Dof5.4), enhanced the reporter gene activity. Moreover, At5g60850 (Dof5.4), At2g28810 (Dof2.2), and At5g60200 (Dof5.3) have proved to function as transcription factors for HMG-CoA reductase, IPP isomerase, cis-prenyltransferase, and small rubber particle protein because the longer the sequence of the promoter region was, the more often the reporter gene activity was expressed, or, in other words, the higher number of At5g60850 (Dof5.4)-, At2g28810 (Dof2.2)-, or At5g60200 (Dof5.3)-binding sites the promoter sequence contained, the more often the reporter gene activity was expressed. These results demonstrated that the introduction of At5g60850 (Dof5.4), At2g28810 (Dof2.2), or At5g60200 (Dof5.3), particularly At5g60850 (Dof5.4), into an isoprenoid-producing plant enhances the overall polyisoprenoid biosynthesis pathway and thus increases polyisoprenoid production.

(Second Aspect of the Present Invention)
(Preparation of Promoter Sequence)

A DNA fragment containing the gene encoding HMG-CoA reductase from leaves of *Hevea brasiliensis* (the base sequence of the gene is set forth in the sequence listing as SEQ ID NO:31) and its promoter was cloned in the following manner. First, genomic DNA was extracted from leaves of *Hevea brasiliensis*. The extraction was carried out using a commercial genomic DNA extraction kit. The gene encoding HMG-CoA reductase with its promoter region was amplified by TAIL-PCR using random primers shown as Primers 1 to 6 and primers corresponding to the gene encoding HMG-CoA reductase.

```
                                     (SEQ ID NO: 33)
    Primer 1: 5'-ntcgastwtsgwgtt-3'

(SEQ ID NO: 34)
    Primer 2: 5'-ngtcgtswganawgaa-3'

(SEQ ID NO: 35)
    Primer 3: 5'-wgtgnagwancanag-3'

(SEQ ID NO: 36)
    Primer 4: 5'-sttntastnctntgc-3'

(SEQ ID NO: 37)
    Primer 5: 5'-sstggstanatwatwct-3'

(SEQ ID NO: 38)
    Primer 6: 5'-agwgnagwancanaga-3'
```

The base sequences of the DNA fragments obtained using the primers were analyzed to obtain the promoter sequence of HMG-CoA reductase. The base sequence of the promoter sequence of HMG-CoA reductase is shown as SEQ ID NO:39.

The promoter sequence was analyzed using a plant promoter database (a database of plant cis-acting regulatory DNA elements (PLACE)) (www.dna.affrc.go.jp/PLACE/).

The analysis revealed that the sequence contains a lot of Myb transcription factor binding (recognition) sites (WAACCA, CCWACC, CANNTG).

(Amplification of Promoter Region)

As the promoter region of the gene, the following regions were amplified by PCR.

HMG-CoA reductase promoter: −1 to −1500 bp, −1 to −1000 bp, and −1 to −500 bp

The PCR products were each cloned into pMD20T (Takara Bio, Inc.) to construct pMD20T-hmgpro (−1500), pMD20T-hmgpro (−1000), and pMD20T-hmgpro (−500). The inserted PCR products were sequenced to confirm that no mutation was introduced.

(Construction of Reporter Sequence-Containing Vector)

The plasmids constructed in (Amplification of promoter region) were restricted with SpeI and any of HindIII, KpnI and BamHI, and the promoter sequence fragments were individually incorporated at a site of pYES3/CT/LacZ from which the T7 promoter region had been removed, that is, immediately upstream of the lacZ reporter gene to construct pYES3-hmgprolacZ (−1500), pYES3-hmgprolacZ (−1000), and pYES3-hmgpro (−500). Ligation high ver. 2 (TOYOBO) was used for ligation.

(Construction of Vector for Gene Introduction into Yeast Chromosome)

The sequence from the SpeI site to the CYC1 transcription termination signal of each of the plasmids constructed in (Construction of reporter sequence-containing vector) was amplified by PCR, and the resulting fragments were restricted with SalI, SmaI, XbaI or SphI, thereby providing DNA fragments with the promoter sequences each linked to the lacZ gene. In order to allow the obtained DNA fragments to be inserted into a yeast chromosome, the DNA fragments were individually incorporated into pAUR101 DNA (Takara Bio, Inc.) treated with the same restriction enzymes to construct pAUR101-hmgprolacZ (−1500), pAUR101-hmg-prolacZ (−1000), and pAUR101-hmgpro (−500). Ligation high ver.2 was used for ligation as above.

(Acquisition of Transcription Factor Gene)

Next, PCR was performed using an *Arabidopsis thaliana* cDNA library as a template. The PCR produced the following three PCR fragments: At4g09460 (Myb6) (SEQ ID NO: 25), At1g22640 (Myb3) (SEQ ID NO: 27), and At1g18330 (EPR1) (SEQ ID NO: 29). The obtained PCR products were each cloned into pMD20T to construct pMD20T-Myb6, pMD20T-Myb3, and pMD20T-EPR1. The inserted PCR products were sequenced to confirm that no mutation was introduced.

(Construction of Transcription Factor Expression Vector)

The plasmids constructed in (Acquisition of transcription factor gene) were restricted with SpeI, BamHI, or EcoRV, and the transcription factor genes were individually incorporated downstream of the TEF1 promoter region of p427TEF (COSMO BIO Co., Ltd.) to construct pTEF-Myb6, pTEF-Myb3, and pTEF-EPR1. Ligation high ver.2 was used for ligation.

(Transformation of Yeast)

The plasmids constructed in (Construction of vector for gene introduction into yeast chromosome) and (Construction of transcription factor expression vector) were introduced into yeast cells (BY4741 strain) by electroporation. Screening for transgenic yeast cells was carried out by culturing the yeast cells on a medium containing the antifungal antibiotics Aureobasidin A (Takara Bio, Inc.) and G418 (Wako Pure Chemical Industries, Ltd.).

(Demonstration of Effect of Transcription Factor)

The transgenic yeast cells were cultured on a medium containing X-gal to assess the expression of lacZ due to transcription factor activity. Specifically, when the lacZ reporter gene, which is linked to the promoter sequence, is expressed, X-gal in the medium is then decomposed to develop a blue color. Based on this mechanism, if the medium turned blue, it was determined that lacZ was expressed due to transcription factor activity. This test was repeated 10 times. Table 2 shows how many times lacZ was expressed due to transcription factor activity.

TABLE 2

| Promoter sequence | Transcription factor | | | |
|---|---|---|---|---|
| | At4g09460 (Myb6) | At1g22640 (Myb3) | At1g18330 (EPR1) | Control (No transcription factor) |
| hmg(−1500) | 6 | 4 | 3 | 1 |
| hmg(−1000) | 4 | 2 | 1 | 1 |
| hmg(−500) | 3 | 2 | 1 | 0 |

Number of yeast cells that exhibited reporter gene activity (N = 10)

Table 2 shows that the use of At4g09460 (Myb6) (SEQ ID NOs: 25 and 26), At1g22640 (Myb3) (SEQ ID NOs: 27 and 28), or At1g18330 (EPR1) (SEQ ID NOs: 29 and 30), particularly At4g09460 (Myb6), enhanced the reporter gene activity. Moreover, At4g09460 (Myb6), At1g22640 (Myb3), and At1g18330 (EPR1) have proved to function as transcription factors for HMG-CoA reductase because the longer the sequence of the promoter region was, the more often the reporter gene activity was expressed, or, in other words, the higher number of At4g09460 (Myb6)-, At1g22640 (Myb3)-, or At1g18330 (EPR1)-binding sites the promoter sequence contained, the more often the reporter gene activity was expressed. These results demonstrated that the introduction of At4g09460 (Myb6), At1g22640 (Myb3), or At1g18330 (EPR1), particularly At4g09460 (Myb6), into an isoprenoid-producing plant enhances the rate-limiting step of IPP biosynthesis in the MVA pathway, and thereby suitably enhances the polyisoprenoid biosynthesis pathway, and thus it is possible to suitably increase polyisoprenoid production.

(Third Aspect of the Present Invention)

(Preparation of Promoter Sequence)

A DNA fragment containing the gene encoding HMG-CoA reductase from leaves of *Hevea brasiliensis* (the base sequence of the gene is set forth in the sequence listing as SEQ ID NO: 46) and its promoter was cloned in the following manner. First, genomic DNA was extracted from leaves of *Hevea brasiliensis*. The extraction was carried out using a commercial genomic DNA extraction kit. The gene encoding HMG-CoA reductase with its promoter region was amplified by TAIL-PCR using random primers shown as Primers 1 to 6 and primers corresponding to the gene encoding HMG-CoA reductase.

```
                                    (SEQ ID NO: 48)
Primer 1: 5'-ntcgastwtsgwgtt-3'

(SEQ ID NO: 49)
Primer 2: 5'-ngtcgtswganawgaa-3'

(SEQ ID NO: 50)
Primer 3: 5'-wgtgnagwancanag-3'

(SEQ ID NO: 51)
Primer 4: 5'-sttntastnctntgc-3'

(SEQ ID NO: 52)
Primer 5: 5'-sstggstanatwatwct-3'

(SEQ ID NO: 53)
Primer 6: 5'-agwgnagwancanaga-3'
```

The base sequences of the DNA fragments obtained using the primers were analyzed to obtain the promoter sequence of HMG-CoA reductase. The base sequence of the promoter sequence of HMG-CoA reductase is shown as SEQ ID NO:54.

The promoter sequence was analyzed using a plant promoter database (a database of plant cis-acting regulatory DNA elements (PLACE)) (www.dna.affr.go.jp/PLACE/).

The analysis revealed that the sequence contains a lot of bHLH transcription factor binding (recognition) sites (CANNTG).

(Amplification of Promoter Region)

As the promoter region of the gene, the following regions were amplified by PCR.

HMG-CoA reductase promoter: −1 to −1500 bp, −1 to −1000 bp, and −1 to −500 bp

The PCR products were each cloned into pMD20T (Takara Bio, Inc.) to construct pMD20T-hmgpro (−1500), pMD20T-hmgpro (−1000), and pMD20T-hmgpro (−500). The inserted PCR products were sequenced to confirm that no mutation was introduced.

(Construction of Reporter Sequence-Containing Vector)

The plasmids constructed in (Amplification of promoter region) were restricted with SpeI and any of HindIII, KpnI and BamHI, and the promoter sequence fragments were individually incorporated at a site of pYES3/CT/LacZ from which the T7 promoter region had been removed, that is, immediately upstream of the lacZ reporter gene to construct pYES3-hmgprolacZ (−1500), pYES3-hmgprolacZ (−1000), and pYES3-hmgpro (−500). Ligation high ver. 2 (TOYOBO) was used for ligation.

(Construction of Vector for Gene Introduction into Yeast Chromosome)

The sequence from the SpeI site to the CYC1 transcription termination signal of each of the plasmids constructed in (Construction of reporter sequence-containing vector) was amplified by PCR, and the resulting fragments were restricted with SalI, SmaI, XbaI or SphI, thereby providing DNA fragments with the promoter sequences each linked to the lacZ gene. In order to allow the obtained DNA fragments to be inserted into a yeast chromosome, the DNA fragments were individually incorporated into pAUR101 DNA (Takara Bio, Inc.) treated with the same restriction enzymes to construct pAUR101-hmgprolacZ (−1500), pAUR101-hmgprolacZ (−1000), and pAUR101-hmgpro (−500). Ligation high ver.2 was used for ligation as above.

(Acquisition of Transcription Factor Gene)

Next, PCR was performed using an *Arabidopsis thaliana* cDNA library as a template. The PCR produced the following three PCR fragments: At1g63650 (Myc2) (SEQ ID NO: 40), At5g54680 (ILR3) (SEQ ID NO: 42), and At1g02340 (HFR1) (SEQ ID NO: 44). The obtained PCR products were each cloned into pMD20T to construct pMD20T-Myc2, pMD20T-ILR3, and pMD20T-HFR1. The inserted PCR products were sequenced to confirm that no mutation was introduced.

(Construction of Transcription Factor Expression Vector)

The plasmids constructed in (Acquisition of transcription factor gene) were restricted with SpeI, BamHI, or EcoRV, and the transcription factor genes were individually incorporated downstream of the TEF1 promoter region of p427TEF (COSMO BIO Co., Ltd.) to construct pTEF-Myc2, pTEF-ILR3, and pTEF-HRR1. Ligation high ver.2 was used for ligation.

(Transformation of Yeast)

The plasmids constructed in (Construction of vector for gene introduction into yeast chromosome) and (Construction of transcription factor expression vector) were introduced into yeast cells (BY4741 strain) by electroporation. Screening for transgenic yeast cells was carried out by culturing the yeast cells on a medium containing the antifungal antibiotics Aureobasidin A (Takara Bio, Inc.) and G418 (Wako Pure Chemical Industries, Ltd.).

(Demonstration of Effect of Transcription Factor)

The transgenic yeast cells were cultured on a medium containing X-gal to assess the expression of lacZ due to transcription factor activity. Specifically, when the lacZ reporter gene, which is linked to the promoter sequence, is expressed, X-gal in the medium is then decomposed to develop a blue color. Based on this mechanism, if the medium turned blue, it was determined that lacZ was expressed due to transcription factor activity. This test was repeated 10 times. Table 3 shows how many times lacZ was expressed due to transcription factor activity.

TABLE 3

| Promoter sequence | Transcription factor | | | Control (No transcription factor) |
|---|---|---|---|---|
| | At1g63650 (Myc2) | At5g54680 (ILR3) | At1g02340 (HFR1) | |
| hmg(−1500) | 5 | 4 | 2 | 1 |
| hmg(−1000) | 2 | 2 | 1 | 1 |
| hmg(−500) | 2 | 1 | 0 | 0 |

Number of yeast cells that exhibited reporter gene activity (N = 10)

Table 3 shows that the use of At1g63650 (Myc2) (SEQ ID NOs: 40 and 41), At5g54680 (ILR3) (SEQ ID NOs: 42 and 43), or At1g02340 (HFR1) (SEQ ID NOs: 44 and 45), particularly At1g63650 (Myc2), enhanced the reporter gene activity. Moreover, At1g63650 (Myc2), At5g54680 (ILR3), and At1g02340 (HFR1) have proved to function as transcription factors for HMG-CoA reductase because the longer the sequence of the promoter region was, the more often the reporter gene activity was expressed, or, in other words, the higher number of At1g63650 (Myc2)-, At5g54680 (ILR3)-, or At1g02340 (HFR1)-binding sites the promoter sequence contained, the more often the reporter gene activity was expressed. These results demonstrated that the introduction of At1g63650 (Myc2), At5g54680 (ILR3), or At1g02340 (HFR1), particularly At1g63650 (Myc2), into an isoprenoid-producing plant enhances the rate-limiting step of IPP biosynthesis in the MVA pathway, and thereby suitably enhances the polyisoprenoid biosynthesis pathway, and thus it is possible to suitably increase polyisoprenoid production.

(Sequence Listing Free Text)

SEQ ID NO:1: base sequence of Dof5.4-encoding gene from *Arabidopsis thaliana*

SEQ ID NO:2: amino acid sequence of Dof5.4 from *Arabidopsis thaliana*

SEQ ID NO:3: base sequence of Dof2.2-encoding gene from *Arabidopsis thaliana*

SEQ ID NO:4: amino acid sequence of Dof2.2 from *Arabidopsis thaliana*

SEQ ID NO:5: base sequence of Dof5.3-encoding gene from *Arabidopsis thaliana*

SEQ ID NO:6: amino acid sequence of Dof.5.3 from *Arabidopsis thaliana*

SEQ ID NO:7: base sequence of cis-prenyltransferase-encoding gene from *Hevea brasiliensis*

SEQ ID NO:8: amino acid sequence of cis-prenyltransferase from *Hevea brasiliensis*

SEQ ID NO:9: base sequence of HMG-CoA reductase-encoding gene from *Hevea brasiliensis*

SEQ ID NO:10: amino acid sequence of HMG-CoA reductase from *Hevea brasiliensis*

SEQ ID NO:11: base sequence of IPP isomerase-encoding gene from *Hevea brasiliensis*

SEQ ID NO:12: amino acid sequence of IPP isomerase from *Hevea brasiliensis*

SEQ ID NO:13: base sequence of SRPP-encoding gene from *Hevea brasiliensis*

SEQ ID NO:14: amino acid sequence of SRPP from *Hevea brasiliensis*

SEQ ID NO:15: Primer 1
SEQ ID NO:16: Primer 2
SEQ ID NO:17: Primer 3
SEQ ID NO:18: Primer 4
SEQ ID NO:19: Primer 5
SEQ ID NO:20: Primer 6

SEQ ID NO:21: base sequence of promoter sequence of HMG-CoA reductase from *Hevea brasiliensis*
SEQ ID NO:22: base sequence of promoter sequence of IPP isomerase from *Hevea brasiliensis*
SEQ ID NO:23: base sequence of promoter sequence of cis-prenyltransferase from *Hevea brasiliensis*
SEQ ID NO:24: base sequence of promoter sequence of SRPP from *Hevea brasiliensis*
SEQ ID NO:25: base sequence of Myb6-encoding gene from *Arabidopsis thaliana*
SEQ ID NO:26: amino acid sequence of Myb6 from *Arabidopsis thaliana*
SEQ ID NO:27: base sequence of Myb3-encoding gene from *Arabidopsis thaliana*
SEQ ID NO:28: amino acid sequence of Myb3 from *Arabidopsis thaliana*
SEQ ID NO:29: base sequence of EPR1-encoding gene from *Arabidopsis thaliana*
SEQ ID NO:30: amino acid sequence of EPR1 from *Arabidopsis thaliana*
SEQ ID NO:31: base sequence of HMG-CoA reductase-encoding gene from *Hevea brasiliensis*
SEQ ID NO:32: amino acid sequence of HMG-CoA reductase from *Hevea brasiliensis*
SEQ ID NO:33: Primer 1
SEQ ID NO:34: Primer 2
SEQ ID NO:35: Primer 3
SEQ ID NO:36: Primer 4
SEQ ID NO:37: Primer 5
SEQ ID NO:38: Primer 6
SEQ ID NO:39: base sequence of promoter sequence of HMG-CoA reductase from *Hevea brasiliensis*
SEQ ID NO:40: base sequence of Myc2-encoding gene from *Arabidopsis thaliana*
SEQ ID NO:41: amino acid sequence of Myc2 from *Arabidopsis thaliana*
SEQ ID NO:42: base sequence of ILR3-encoding gene from *Arabidopsis thaliana*
SEQ ID NO:43: amino acid sequence of ILR3 from *Arabidopsis thaliana*
SEQ ID NO:44: base sequence of HFR1-encoding gene from *Arabidopsis thaliana*
SEQ ID NO:45: amino acid sequence of HFR1 from *Arabidopsis thaliana*
SEQ ID NO:46: base sequence of HMG-CoA reductase-encoding gene from *Hevea brasiliensis*
SEQ ID NO:47: amino acid sequence of HMG-CoA reductase from *Hevea brasiliensis*
SEQ ID NO:48: Primer 1
SEQ ID NO:49: Primer 2
SEQ ID NO:50: Primer 3
SEQ ID NO:51: Primer 4
SEQ ID NO:52: Primer 5
SEQ ID NO:53: Primer 6
SEQ ID NO:54: base sequence of promoter sequence of HMG-CoA reductase from *Hevea brasiliensis*

The invention claimed is:

1. An isoprenoid-producing plant, into which has been introduced a heterologous gene encoding a Dof transcription factor,
wherein the gene is either of the following DNAs:
[1] a DNA comprising the sequence SEQ ID NO:1; and
[2] a DNA sequence having at least 90% sequence identity to the sequence of SEQ ID NO:1, and encoding a protein with transcription factor activity,
wherein the isoprenoid-producing plant is one selected from the genera *Hevea* or *Taraxacum*.

2. A method for producing a polyisoprenoid using the isoprenoid-producing plant according to claim 1.

* * * * *

SEQUENCE LISTING

```
<160> NUMBER OF SEQ ID NOS: 54

<210> SEQ ID NO 1
<211> LENGTH: 1425
<212> TYPE: DNA
<213> ORGANISM: Arabidopsis thaliana

<400> SEQUENCE: 1
gaacaagtct ttcccatgct caccacttca cctctctctc tctttcttct ccactgtaac     60
ctcccaattc aaaaacaatt ataaaccaaa cttgattaat atatatttct ttatcatcat    120
ctcttcgaaa tgcaagatat tcatgatttc tccatgaacg gagttggtgg tgggggagga    180
ggaggaggga ggtttttcgg tggaggaatc ggcggcggag gaggtggtga tcgaaggatg    240
agagctcatc agaacaatat acttaaccat catcaatctc tcaagtgtcc tcgttgtaat    300
tctcttaaca caaagttctg ttactacaac aattacaatc tttctcagcc tcgtcacttt    360
tgcaagaact gtcgtcgtta ctggactaaa ggtggtgttc tccgtaacgt tcccgtcgga    420
ggtggttgcc ggaaagctaa acgttcgaaa acaaaacagg ttccgtcgtc gtcatcagcc    480
gacaaaccaa cgacgacgca agatgatcat cacgtggagg agaaatcgag tacaggatct    540
cactctagca gcgagagctc ttctctcacc gcttctaact ctaccaccgt cgccgccgtc    600
tccgtcaccg cggcggcgga agttgcttcg tcggttattc caggttttga tatgcctaat    660
atgaaaattt acggtaacgg gatcgagtgg tcgacgttac ttggacaagg ctcatcggcc    720
ggtggtgttt tctcggagat cggtggtttt ccggcggttt cagctattga aactacaccg    780
tttggattcg ggggtaaatt cgtaaatcaa gatgatcatc tgaagttaga aggtgaaact    840
gtacagcagc aacagtttgg agatcgaacg gctcaggttg agtttcaagg aagatcttcg    900
gatccgaata tgggatttga accgttggat tggggaagtg gcggtggaga tcaaacactg    960
tttgatttaa ccagtaccgt tgatcatgca tactggagtc aaagtcaatg gacgtcgtct   1020
```

```
gaccaagatc agagtggtct ctaccttcct tgattctgat catagcttct tcttcttaac   1080
ccaaaaatat atattttata cacataaggt aaagttcgat gaagtggttt ttttaatttt   1140
tatttgatgg gtttaaaacg ggatttatta tataattata tgactgcttg taaattttt    1200 tcccaaatat caaatttacc tctcttttt tttagttttt ggaatatccc aagagtgcaa    1260
atttatgtgg catggtttta gtttggcttc ggttcagttt tggaactggc cgttttactt   1320
atcgttgtat catatttgat aagattttaa ttttctggga tttttttttg gttttcattg   1380
atgtatctaa taaatttata tatatattga ttgggcatac aaaaa                    1425

<210> SEQ ID NO 2
<211> LENGTH: 307
<212> TYPE: PRT
<213> ORGANISM: Arabidopsis thaliana

<400> SEQUENCE: 2

Met Gln Asp Ile His Asp Phe Ser Met Asn Gly Val Gly Gly Gly Gly
 1               5                  10                  15

Gly Gly Gly Gly Arg Phe Gly Gly Gly Ile Gly Gly Gly Gly
                20                  25                  30

Gly Asp Arg Arg Met Arg Ala His Gln Asn Asn Ile Leu Asn His His
            35                  40                  45

Gln Ser Leu Lys Cys Pro Arg Cys Asn Ser Leu Asn Thr Lys Phe Cys
        50                  55                  60

Tyr Tyr Asn Asn Tyr Asn Leu Ser Gln Pro Arg His Phe Cys Lys Asn
 65                  70                  75                  80

Cys Arg Arg Tyr Trp Thr Lys Gly Gly Val Leu Arg Asn Val Pro Val
                 85                  90                  95

Gly Gly Gly Cys Arg Lys Ala Lys Arg Ser Lys Thr Lys Gln Val Pro
            100                 105                 110

Ser Ser Ser Ser Ala Asp Lys Pro Thr Thr Thr Gln Asp Asp His His
        115                 120                 125

Val Glu Glu Lys Ser Ser Thr Gly Ser His Ser Ser Ser Glu Ser Ser
130                 135                 140

Ser Leu Thr Ala Ser Asn Ser Thr Thr Val Ala Ala Val Ser Val Thr
145                 150                 155                 160

Ala Ala Ala Glu Val Ala Ser Ser Val Ile Pro Gly Phe Asp Met Pro
                165                 170                 175

Asn Met Lys Ile Tyr Gly Asn Gly Ile Glu Trp Ser Thr Leu Leu Gly
            180                 185                 190

Gln Gly Ser Ser Ala Gly Gly Val Phe Ser Glu Ile Gly Gly Phe Pro
        195                 200                 205

Ala Val Ser Ala Ile Glu Thr Thr Pro Phe Gly Phe Gly Gly Lys Phe
    210                 215                 220

Val Asn Gln Asp Asp His Leu Lys Leu Glu Gly Glu Thr Val Gln Gln
225                 230                 235                 240

Gln Gln Phe Gly Asp Arg Thr Ala Gln Val Glu Phe Gln Gly Arg Ser
                245                 250                 255

Ser Asp Pro Asn Met Gly Phe Glu Pro Leu Asp Trp Gly Ser Gly Gly
            260                 265                 270

Gly Asp Gln Thr Leu Phe Asp Leu Thr Ser Thr Val Asp His Ala Tyr
        275                 280                 285

Trp Ser Gln Ser Gln Trp Thr Ser Ser Asp Gln Asp Gln Ser Gly Leu
    290                 295                 300
```

Tyr Leu Pro
305

<210> SEQ ID NO 3
<211> LENGTH: 1371
<212> TYPE: DNA
<213> ORGANISM: Arabidopsis thaliana

<400> SEQUENCE: 3

| | | | | |
|---|---|---|---|---|
| tcaaacttta | ttaaagaaag | aagaacaaag | agataaaagg | gaagaagaac aatggttttc | 60 |
| tcatccgtct | caagcttttt | agatccacca | attaattggc | cacagtctgc gaatccaaat | 120 |
| aaccatcctc | atcatcatca | gctacaagaa | aatggaagtt | tagttagtgg ccaccaccaa | 180 |
| gtactctctc | accacttccc | acaaaaccct | aaccctaacc | accaccatgt tgagacagca | 240 |
| gccgccacca | ccgttgatcc | gagcagtctc | aatggccagg | cggctgagag agcgaggcta | 300 |
| gctaagaact | ctcagccgcc | agagggagcc | ctaaagtgtc | ctcgatgtga ctcagccaat | 360 |
| accaagttct | gttacttcaa | caactacaac | ctcacgcagc | cacgccactt ctgcaaagct | 420 |
| tgccgtcgct | actggacacg | tggcggtgcc | ttgaggaacg | tacctgtcgg tggtggctgc | 480 |
| cggaggaata | agaagggtaa | atccggaaat | tcaaagtctt | cctcttcctc tcagaacaag | 540 |
| cagtcaacgt | ctatggtcaa | cgctacaagc | cctactaata | ctagtaatgt ccagctccaa | 600 |
| acaaatagcc | aattcccatt | tttgcccact | ctacaaaacc | tcactcaact tggtggtatt | 660 |
| ggtttaaact | agccgccat | taatggaaat | aatggtggaa | atggtaacac tagctcaagt | 720 |
| ttcttgaatg | acttagggtt | ttttcatggt | ggtaacactt | caggtccggt catgggtaac | 780 |
| aacaacgaga | ataacctaat | gacttctctt | ggatcatcca | gccactttgc tttgttcgat | 840 |
| cgaaccatgg | gattatataa | tttccctaac | gaggtaaata | tgggattatc ttctattggt | 900 |
| gctactaggg | tttctcaaac | tgctcaggtg | aaaatggagg | acaaccattt gggtaatata | 960 |
| agccgcccgg | tttcggggtt | gacatctcca | gggaatcaat | ccaatcaata ttggaccggt | 1020 |
| caaggtctcc | ccggttcttc | atctaacgat | catcatcacc | agcatcttat gtgattgtgt | 1080 |
| ttcttagccg | tcggattatt | catggacctt | gttaaagatc | caatgcatat ggagaaacta | 1140 |
| aaaggtatat | tagaatcggt | ttgttatagt | caatgggtgc | atatagaatc aggtgtgaca | 1200 |
| aagaattatt | cgtattgtgt | gattatgaac | ttgttagatg | tatgagagtg tacttgtcga | 1260 |
| gtttgtgttt | gttcaattcg | tattattcac | tcaaattttc | ataaaataat actaacttat | 1320 |
| ctgtatgtca | tattttttatt | ttggtttcta | agtcttgagt | acgtgagaac c | 1371 |

<210> SEQ ID NO 4
<211> LENGTH: 340
<212> TYPE: PRT
<213> ORGANISM: Arabidopsis thaliana

<400> SEQUENCE: 4

Met Val Phe Ser Ser Val Ser Ser Phe Leu Asp Pro Pro Ile Asn Trp
1               5                   10                  15

Pro Gln Ser Ala Asn Pro Asn Asn His Pro His His Gln Leu Gln
            20                  25                  30

Glu Asn Gly Ser Leu Val Ser Gly His His Gln Val Leu Ser His His
        35                  40                  45

Phe Pro Gln Asn Pro Asn Pro Asn His His Val Glu Thr Ala Ala
    50                  55                  60

Ala Thr Thr Val Asp Pro Ser Ser Leu Asn Gly Gln Ala Ala Glu Arg

```
                     65                  70                  75                  80
Ala Arg Leu Ala Lys Asn Ser Gln Pro Pro Glu Gly Ala Leu Lys Cys
                     85                  90                  95

Pro Arg Cys Asp Ser Ala Asn Thr Lys Phe Cys Tyr Phe Asn Asn Tyr
                    100                 105                 110

Asn Leu Thr Gln Pro Arg His Phe Cys Lys Ala Cys Arg Arg Tyr Trp
                    115                 120                 125

Thr Arg Gly Gly Ala Leu Arg Asn Val Pro Val Gly Gly Gly Cys Arg
            130                 135                 140

Arg Asn Lys Lys Gly Lys Ser Gly Asn Ser Lys Ser Ser Ser Ser Ser
145                 150                 155                 160

Gln Asn Lys Gln Ser Thr Ser Met Val Asn Ala Thr Ser Pro Thr Asn
                    165                 170                 175

Thr Ser Asn Val Gln Leu Gln Thr Asn Ser Gln Phe Pro Phe Leu Pro
                    180                 185                 190

Thr Leu Gln Asn Leu Thr Gln Leu Gly Gly Ile Gly Leu Asn Leu Ala
                    195                 200                 205

Ala Ile Asn Gly Asn Asn Gly Gly Asn Gly Asn Thr Ser Ser Ser Phe
            210                 215                 220

Leu Asn Asp Leu Gly Phe Phe His Gly Gly Asn Thr Ser Gly Pro Val
225                 230                 235                 240

Met Gly Asn Asn Asn Glu Asn Asn Leu Met Thr Ser Leu Gly Ser Ser
                    245                 250                 255

Ser His Phe Ala Leu Phe Asp Arg Thr Met Gly Leu Tyr Asn Phe Pro
                    260                 265                 270

Asn Glu Val Asn Met Gly Leu Ser Ser Ile Gly Ala Thr Arg Val Ser
                    275                 280                 285

Gln Thr Ala Gln Val Lys Met Glu Asp Asn His Leu Gly Asn Ile Ser
            290                 295                 300

Arg Pro Val Ser Gly Leu Thr Ser Pro Gly Asn Gln Ser Asn Gln Tyr
305                 310                 315                 320

Trp Thr Gly Gln Gly Leu Pro Gly Ser Ser Ser Asn Asp His His His
                    325                 330                 335

Gln His Leu Met
            340

<210> SEQ ID NO 5
<211> LENGTH: 1449
<212> TYPE: DNA
<213> ORGANISM: Arabidopsis thaliana

<400> SEQUENCE: 5
acttttaatt tctactcata tccatcattc tctctgatct caagaaataa tctcaaatct      60
cttacactca tagtcttcaa gcaacttctc agattcagct cttatggatc atttgttaca     120
acaccaggat gttttgggaa attataacaa agcaagagaa gcaatgggac tatcatattc     180
atcaaaccca acaccgttag ataacgacca gaagaaacct tctcctgcaa cggctgtgac     240
aaggccacag cctccggagc tagctctcag gtgtccacgt tgcgactcaa caaacacaaa     300
gttttgttac tacaacaact acagtctcac tcagcctcgc tacttctgca aatcatgccg     360
gagatattgg actaaggtg gaactctaag gaacatcccc gtgggtggag gctgccggaa     420
aaacaaacga tccacatctt cggctgcaag aagcctcaga accactccag aaccggcgtc     480
ccacgacggg aaagtcttct cggcggcagg ttttaatggg tatagtaaca atgaacatat     540
```

```
tgatctgagc ttagcctttg ccttgctgaa caaacaacat ccggggagtt cttcacagct      600
agggtttcat tcagaactcg gtagctctca tcagtctgac atggaaggta tgtttgggac      660
aagccaacaa aaagagaacg ctacttatgc gtttggtaac gggagcagcg gtttgggtga      720
tccaagcaga gtcttatggg gatttccatg gcagatgaat ggagagagct ttggaatgat      780
gaacatagga ggaggtggtg gtcatgtaga tcagattgat tcagggagag agatgtggac      840
caatatgaac tacattaatt ctggtgcttt aatgtagttc aaaattaaaa ccccaatatt      900
atttgggttt tgatttaggg tttgaatttc atgttttta atgggagtag aaaagggtgg       960
tagctatttt atgaaatggt taaggaagta tagatatatt agggcttctt caaagagttt     1020
caaacttgca aaatggggtt ggggtagttc ttgttttcga tttctgatct aaattgttga     1080
gtttctttat ttgtatgttc actatgttta aatgaaacat ttcctttgtt gttctaattt     1140
cttaattcat tttttctaaa ttaagtttta cgaaattcaa atggcttctg gaatgaacaa     1200
aaaatgaaaa ttttatcaat gaagaatag tttaccatag tatggaatgt gtggaataat       1260
ttaccataat ggaattgtgt gttcaaaccc taatctctcc cattgaaacc taatcattat     1320
ttctcctata aaatctgac atatagaggc ttcttaatgg ctcggttaat aaggttgatg      1380
tttctactta attgatttag tgacgtaaag gatcaatctt ggtaatggta tataatgtca     1440
aataagtat                                                             1449

<210> SEQ ID NO 6
<211> LENGTH: 257
<212> TYPE: PRT
<213> ORGANISM: Arabidopsis thaliana

<400> SEQUENCE: 6

Met Asp His Leu Leu Gln His Gln Asp Val Phe Gly Asn Tyr Asn Lys
1               5                   10                  15

Ala Arg Glu Ala Met Gly Leu Ser Tyr Ser Ser Asn Pro Thr Pro Leu
            20                  25                  30

Asp Asn Asp Gln Lys Lys Pro Ser Pro Ala Thr Ala Val Thr Arg Pro
        35                  40                  45

Gln Pro Pro Glu Leu Ala Leu Arg Cys Pro Arg Cys Asp Ser Thr Asn
    50                  55                  60

Thr Lys Phe Cys Tyr Tyr Asn Asn Tyr Ser Leu Thr Gln Pro Arg Tyr
65                  70                  75                  80

Phe Cys Lys Ser Cys Arg Arg Tyr Trp Thr Lys Gly Gly Thr Leu Arg
                85                  90                  95

Asn Ile Pro Val Gly Gly Gly Cys Arg Lys Asn Lys Arg Ser Thr Ser
            100                 105                 110

Ser Ala Ala Arg Ser Leu Arg Thr Thr Pro Glu Pro Ala Ser His Asp
        115                 120                 125

Gly Lys Val Phe Ser Ala Ala Gly Phe Asn Gly Tyr Ser Asn Asn Glu
    130                 135                 140

His Ile Asp Leu Ser Leu Ala Phe Ala Leu Leu Asn Lys Gln His Pro
145                 150                 155                 160

Gly Ser Ser Ser Gln Leu Gly Phe His Ser Glu Leu Gly Ser Ser His
                165                 170                 175

Gln Ser Asp Met Glu Gly Met Phe Gly Thr Ser Gln Gln Lys Glu Asn
            180                 185                 190

Ala Thr Tyr Ala Phe Gly Asn Gly Ser Ser Gly Leu Gly Asp Pro Ser
        195                 200                 205
```

```
Arg Val Leu Trp Gly Phe Pro Trp Gln Met Asn Gly Glu Ser Phe Gly
    210             215                 220
Met Met Asn Ile Gly Gly Gly Gly His Val Asp Gln Ile Asp Ser
225             230                 235                 240
Gly Arg Glu Met Trp Thr Asn Met Asn Tyr Ile Asn Ser Gly Ala Leu
                245                 250                 255
Met
```

<210> SEQ ID NO 7
<211> LENGTH: 873
<212> TYPE: DNA
<213> ORGANISM: Hevea brasiliensis

<400> SEQUENCE: 7

```
atgaaattat acaccggtga gaggccaagt gtgttcagac ttttagggaa gtatatgaga      60
aaagggttat atggcatcct aacccagggt cccatcccta ctcatcttgc cttcatattg    120
gatggaaaca ggaggtttgc taagaagcat aaactgccag aaggaggtgg tcataaggct    180
ggatttttag ctcttctgaa cgtgctaact tattgctatg agttaggagt gaaatatgcg    240
actatctatg cctttagcat cgataatttt cgaaggaaac ctcatgaggt tcagtacgta    300
atgaatctaa tgctggagaa gattgaaggg atgatcatgg aagaaagtat catcaatgca    360
tatgatattt gcgtacgttt tgtgggtaac ctgaagcttt taagtgagcc agtcaagacc    420
gcagcagata agattatgag ggctactgcc aacaattcca aatgtgtgct tctccttgct    480
gtatgctata cttcaactga tgagatcgtg catgctgttg aagaatcctc tgaattgaac    540
tccaatgaag tttgtaacaa tcaagaattg gaggaggcaa atgcaactgg aagcggtact    600
gtgattcaaa ctgagaacat ggagtcgtat tctggaataa aacttgtaga ccttgagaaa    660
aacacctaca taaatcctta tcctgatgtt ctgattcgaa cttctgggga gacccgtctg    720
agcaactact tactttggca gactactaat tgcatactgt attctcctta tgcactgtgg    780
ccagagattg gtcttcgaca cgtggtgtgg tcagtaatta acttccaacg tcattattct    840
tacttggaga acataagga atacttaaaa taa                                   873
```

<210> SEQ ID NO 8
<211> LENGTH: 290
<212> TYPE: PRT
<213> ORGANISM: Hevea brasiliensis

<400> SEQUENCE: 8

```
Met Lys Leu Tyr Thr Gly Glu Arg Pro Ser Val Phe Arg Leu Leu Gly
1               5                   10                  15
Lys Tyr Met Arg Lys Gly Leu Tyr Gly Ile Leu Thr Gln Gly Pro Ile
                20                  25                  30
Pro Thr His Leu Ala Phe Ile Leu Asp Gly Asn Arg Arg Phe Ala Lys
            35                  40                  45
Lys His Lys Leu Pro Glu Gly Gly Gly His Lys Ala Gly Phe Leu Ala
        50                  55                  60
Leu Leu Asn Val Leu Thr Tyr Cys Tyr Glu Leu Gly Val Lys Tyr Ala
65                  70                  75                  80
Thr Ile Tyr Ala Phe Ser Ile Asp Asn Phe Arg Arg Lys Pro His Glu
                85                  90                  95
Val Gln Tyr Val Met Asn Leu Met Leu Glu Lys Ile Glu Gly Met Ile
            100                 105                 110
Met Glu Glu Ser Ile Ile Asn Ala Tyr Asp Ile Cys Val Arg Phe Val
```

```
            115                 120                 125
Gly Asn Leu Lys Leu Leu Ser Glu Pro Val Lys Thr Ala Ala Asp Lys
    130                 135                 140

Ile Met Arg Ala Thr Ala Asn Asn Ser Lys Cys Val Leu Leu Leu Ala
145                 150                 155                 160

Val Cys Tyr Thr Ser Thr Asp Glu Ile Val His Ala Val Glu Glu Ser
                165                 170                 175

Ser Glu Leu Asn Ser Asn Glu Val Cys Asn Asn Gln Glu Leu Glu Glu
            180                 185                 190

Ala Asn Ala Thr Gly Ser Gly Thr Val Ile Gln Thr Glu Asn Met Glu
        195                 200                 205

Ser Tyr Ser Gly Ile Lys Leu Val Asp Leu Glu Lys Asn Thr Tyr Ile
    210                 215                 220

Asn Pro Tyr Pro Asp Val Leu Ile Arg Thr Ser Gly Glu Thr Arg Leu
225                 230                 235                 240

Ser Asn Tyr Leu Leu Trp Gln Thr Thr Asn Cys Ile Leu Tyr Ser Pro
                245                 250                 255

Tyr Ala Leu Trp Pro Glu Ile Gly Leu Arg His Val Val Trp Ser Val
            260                 265                 270

Ile Asn Phe Gln Arg His Tyr Ser Tyr Leu Glu Lys His Lys Glu Tyr
        275                 280                 285

Leu Lys
    290

<210> SEQ ID NO 9
<211> LENGTH: 1728
<212> TYPE: DNA
<213> ORGANISM: Hevea brasiliensis

<400> SEQUENCE: 9
atggacacca ccggccggct ccaccaccga aagcatgcta cacccgttga ggaccgttct      60
ccgaccactc cgaaagcgtc ggacgcgctt ccgcttcccc tctacctgac caacgcggtt     120
ttcttcacgc tgttcttctc ggtggcgtat tacctcctcc accggtggcg cgacaagatc     180
cgcaactcca ctcccttca tatcgttact ctctctgaaa ttgttgctat tgtctccctc     240
attgcctctt tcatttacct cctaggattc ttcggtatcg attttgtgca gtcattcatt     300
gcacgcgcct cccatgacgt gtgggacctc gaagatacgg atcccaacta cctcatcgat     360
gaagatcacc gtctcgttac ttgccctccc gctaatatat ctactaagac taccattatt     420
gccgcaccta ccaaattgcc tacctcggaa cccttaattg cacccttagt ctcggaggaa     480
gacgaaatga tcgtcaactc cgtcgtggat gggaagatac cctcctattc tctggagtcg     540
aagctcgggg actgcaaacg agcggctgcg attcgacgcg aggctttgca gaggatgaca     600
aggaggtcgc tggaaggctt gccagtagaa gggttcgatt acgagtcgat tttaggacaa     660
tgctgtgaaa tgccagtggg atacgtgcag attccggtgg ggattgcggg gccgttgttg     720
ctgaacgggc gggagtactc tgttccaatg gcgaccacgg agggttgttt ggtggcgagc     780
actaatagag ggtgtaaggc gatttacttg tcaggtgggg ccaccagcgt cttgttgaag     840
gatggcatga caagagcgcc tgttgtaaga ttcgcgtcgg cgactagagc gcggagttg      900 aagttcttct tggaggatcc tgacaatttt gataccttgg ccgtagtttt aacaagtcc      960 agtagatttg cgaggctcca aggcattaaa tgctcaattg ctggtaagaa tctttatata    1020
agattcagct gcagcactgg cgatgcaatg gggatgaaca tggtttctaa aggggttcaa    1080
```

-continued

```
aacgttcttg aatttcttca aagtgatttt tctgatatgg atgtcattgg aatctcagga    1140 aattttttgtt cggataagaa gcctgctgct gtaaattgga ttgaaggacg tggcaaatca    1200
gttgtttgtg aggcaattat caaggaagag gtggtgaaga aggtgttgaa aaccaatgtg    1260
gcctccctag tggagcttaa catgctcaag aatcttgctg ttctgctgt tgctggtgct    1320 ttgggtggat ttaatgccca tgcaggcaac atcgtatctg caatctttat tgccactggc    1380
caggatccag cacagaatgt tgagagttct cattgcatta ccatgatgga agctgtcaat    1440
gatggaaagg atctccatat ctctgtgacc atgccctcca ttgaggtggg tacagtcgga    1500
ggtggaactc aacttgcatc tcagtctgct tgtctcaatt tgcttggggt gaagggtgca    1560
aacaaagagt cgccaggatc aaactcaagg ctccttgctg ccatcgtagc tggttcagtt    1620
ttggctggtg agctctcctt gatgtctgcc attgcagctg gcagcttgt caagagtcac    1680 atgaagtaca cagctccag caaagatatg tctaaagctg catcttag             1728
```

<210> SEQ ID NO 10
<211> LENGTH: 575
<212> TYPE: PRT
<213> ORGANISM: Hevea brasiliensis

<400> SEQUENCE: 10

```
Met Asp Thr Thr Gly Arg Leu His His Arg Lys His Ala Thr Pro Val
1               5                   10                  15

Glu Asp Arg Ser Pro Thr Thr Pro Lys Ala Ser Asp Ala Leu Pro Leu
            20                  25                  30

Pro Leu Tyr Leu Thr Asn Ala Val Phe Phe Thr Leu Phe Phe Ser Val
        35                  40                  45

Ala Tyr Tyr Leu Leu His Arg Trp Arg Asp Lys Ile Arg Asn Ser Thr
    50                  55                  60

Pro Leu His Ile Val Thr Leu Ser Glu Ile Val Ala Ile Val Ser Leu
65                  70                  75                  80

Ile Ala Ser Phe Ile Tyr Leu Leu Gly Phe Phe Gly Ile Asp Phe Val
                85                  90                  95

Gln Ser Phe Ile Ala Arg Ala Ser His Asp Val Trp Asp Leu Glu Asp
            100                 105                 110

Thr Asp Pro Asn Tyr Leu Ile Asp Glu Asp His Arg Leu Val Thr Cys
        115                 120                 125

Pro Pro Ala Asn Ile Ser Thr Lys Thr Thr Ile Ile Ala Ala Pro Thr
    130                 135                 140

Lys Leu Pro Thr Ser Glu Pro Leu Ile Ala Pro Leu Val Ser Glu Glu
145                 150                 155                 160

Asp Glu Met Ile Val Asn Ser Val Val Asp Gly Lys Ile Pro Ser Tyr
                165                 170                 175

Ser Leu Glu Ser Lys Leu Gly Asp Cys Lys Arg Ala Ala Ile Arg
            180                 185                 190

Arg Glu Ala Leu Gln Arg Met Thr Arg Arg Ser Leu Glu Gly Leu Pro
        195                 200                 205

Val Glu Gly Phe Asp Tyr Glu Ser Ile Leu Gly Gln Cys Cys Glu Met
    210                 215                 220

Pro Val Gly Tyr Val Gln Ile Pro Val Gly Ile Ala Gly Pro Leu Leu
225                 230                 235                 240

Leu Asn Gly Arg Glu Tyr Ser Val Pro Met Ala Thr Thr Glu Gly Cys
                245                 250                 255

Leu Val Ala Ser Thr Asn Arg Gly Cys Lys Ala Ile Tyr Leu Ser Gly
```

Gly Ala Thr Ser Val Leu Leu Lys Asp Gly Met Thr Arg Ala Pro Val
          260                 265                 270
              275                 280                 285

Val Arg Phe Ala Ser Ala Thr Arg Ala Ala Glu Leu Lys Phe Phe Leu
              290                 295                 300

Glu Asp Pro Asp Asn Phe Asp Thr Leu Ala Val Val Phe Asn Lys Ser
305                 310                 315                 320

Ser Arg Phe Ala Arg Leu Gln Gly Ile Lys Cys Ser Ile Ala Gly Lys
              325                 330                 335

Asn Leu Tyr Ile Arg Phe Ser Tyr Ser Thr Gly Asp Ala Met Gly Met
              340                 345                 350

Asn Met Val Ser Lys Gly Val Gln Asn Val Leu Glu Phe Leu Gln Ser
              355                 360                 365

Asp Phe Ser Asp Met Asp Val Ile Gly Ile Ser Gly Asn Phe Cys Ser
              370                 375                 380

Asp Lys Lys Pro Ala Ala Val Asn Trp Ile Glu Gly Arg Gly Lys Ser
385                 390                 395                 400

Val Val Cys Glu Ala Ile Ile Lys Glu Val Val Lys Lys Val Leu
              405                 410                 415

Lys Thr Asn Val Ala Ser Leu Val Glu Leu Asn Met Leu Lys Asn Leu
              420                 425                 430

Ala Gly Ser Ala Val Ala Gly Ala Leu Gly Gly Phe Asn Ala His Ala
              435                 440                 445

Gly Asn Ile Val Ser Ala Ile Phe Ile Ala Thr Gly Gln Asp Pro Ala
              450                 455                 460

Gln Asn Val Glu Ser Ser His Cys Ile Thr Met Met Glu Ala Val Asn
465                 470                 475                 480

Asp Gly Lys Asp Leu His Ile Ser Val Thr Met Pro Ser Ile Glu Val
              485                 490                 495

Gly Thr Val Gly Gly Gly Thr Gln Leu Ala Ser Gln Ser Ala Cys Leu
              500                 505                 510

Asn Leu Leu Gly Val Lys Gly Ala Asn Lys Glu Ser Pro Gly Ser Asn
              515                 520                 525

Ser Arg Leu Leu Ala Ala Ile Val Ala Gly Ser Val Leu Ala Gly Glu
              530                 535                 540

Leu Ser Leu Met Ser Ala Ile Ala Ala Gly Gln Leu Val Lys Ser His
545                 550                 555                 560

Met Lys Tyr Asn Arg Ser Ser Lys Asp Met Ser Lys Ala Ala Ser
              565                 570                 575

<210> SEQ ID NO 11
<211> LENGTH: 705
<212> TYPE: DNA
<213> ORGANISM: Hevea brasiliensis

<400> SEQUENCE: 11
atgggtgagg ctccagatgt cggcatggat gctgtccaga aacgcctcat gttcgacgat      60
gaatgcattt tagtagatga gaacgatggt gttgttggtc atgcttccaa atataattgt     120
catttgtggg aaaatatttt gaaggggaac gcattacata gagcttttag cgtatttctc     180
ttcaactcaa aatatgagct actccttcag caacgctctg ggacaaaggt gacattcccg     240
cttgtatgga caaacacttg ctgtagtcat cctctgtacc gtgaatctga gcttattgat     300
gaggatgctc ttggtgtgag aaatgctgca caaaggaagc ttttcgatga gcttggtatc     360

```
cctgctgaag atgttccagt tgatcagttt actccactag gacgtatact atataaggcg      420
tcctccgatg gaaagtgggg agagcatgaa cttgattatc tgctctttat agtccgtgat      480
gttaatgtaa atccaaaccc tgatgaggta gctgatgtaa agtatgttaa ccgggatcag      540
ttgaaggagc tcttgaggaa ggcggattct ggcgaggaag gtataaattt gtcaccttgg      600
tttagactag ttgtggacaa cttcttgttg aaatggtggg aaaatgtcga aatgggaca      660 ctcaaggaag cagttgacat gaaaacgatt cacaagttga gttga                     705
```

<210> SEQ ID NO 12
<211> LENGTH: 234
<212> TYPE: PRT
<213> ORGANISM: Hevea brasiliensis

<400> SEQUENCE: 12

```
Met Gly Glu Ala Pro Asp Val Gly Met Asp Ala Val Gln Lys Arg Leu
1               5                   10                  15

Met Phe Asp Asp Glu Cys Ile Leu Val Asp Glu Asn Asp Gly Val Val
            20                  25                  30

Gly His Ala Ser Lys Tyr Asn Cys His Leu Trp Glu Asn Ile Leu Lys
        35                  40                  45

Gly Asn Ala Leu His Arg Ala Phe Ser Val Phe Leu Phe Asn Ser Lys
    50                  55                  60

Tyr Glu Leu Leu Leu Gln Gln Arg Ser Gly Thr Lys Val Thr Phe Pro
65                  70                  75                  80

Leu Val Trp Thr Asn Thr Cys Cys Ser His Pro Leu Tyr Arg Glu Ser
                85                  90                  95

Glu Leu Ile Asp Glu Asp Ala Leu Gly Val Arg Asn Ala Ala Gln Arg
            100                 105                 110

Lys Leu Phe Asp Glu Leu Gly Ile Pro Ala Glu Asp Val Pro Val Asp
        115                 120                 125

Gln Phe Thr Pro Leu Gly Arg Ile Leu Tyr Lys Ala Ser Ser Asp Gly
    130                 135                 140

Lys Trp Gly Glu His Glu Leu Asp Tyr Leu Leu Phe Ile Val Arg Asp
145                 150                 155                 160

Val Asn Val Asn Pro Asn Pro Asp Glu Val Ala Asp Val Lys Tyr Val
                165                 170                 175

Asn Arg Asp Gln Leu Lys Glu Leu Leu Arg Lys Ala Ser Gly Glu
            180                 185                 190

Glu Gly Ile Asn Leu Ser Pro Trp Phe Arg Leu Val Val Asp Asn Phe
        195                 200                 205

Leu Leu Lys Trp Trp Glu Asn Val Glu Asn Gly Thr Leu Lys Glu Ala
    210                 215                 220

Val Asp Met Lys Thr Ile His Lys Leu Ser
225                 230
```

<210> SEQ ID NO 13
<211> LENGTH: 615
<212> TYPE: DNA
<213> ORGANISM: Hevea brasiliensis

<400> SEQUENCE: 13

```
atggctgaag aggtggagga agagaggcta aagtatttgg attttgtgcg agcggctgga      60
gtttatgctg tagattcttt ctcaactctc taccttttatg ccaaggacat atctggtcca     120
ttaaaacctg gtgtcgatac tattgagaat gtggtgaaga ccgtggttac tcctgtttat     180
```

-continued

| | |
|---|---|
| tatattcccc ttgaggctgt caagtttgta gacaaaacgg tggatgtatc ggtcactagc | 240 |
| ctagatggcg ttgttccccc agttatcaag caggtgtctg cccaaactta ctcggtagct | 300 |
| caagatgctc caagaattgt tcttgatgtg gcttcttcag ttttcaacac tggtgtgcag | 360 |
| gaaggcgcaa aagctctgta cgctaatctt gaaccaaaag ctgagcaata tgcggtcatt | 420 |
| acctggcgtg ccctcaataa gctgccacta gttcctcaag tggcaaatgt agttgtgcca | 480 |
| accgctgttt atttctctga aaagtacaac gatgttgttc gtggcactac tgagcaggga | 540 |
| tatagagtgt cctcttattt gcctttgttg cccactgaga aaattactaa ggtgtttgga | 600 |
| gatgaggcat cataa | 615 |

```
<210> SEQ ID NO 14
<211> LENGTH: 204
<212> TYPE: PRT
<213> ORGANISM: Hevea brasiliensis

<400> SEQUENCE: 14
```

Met Ala Glu Glu Val Glu Glu Arg Leu Lys Tyr Leu Asp Phe Val
1               5                   10                  15

Arg Ala Ala Gly Val Tyr Ala Val Asp Ser Phe Ser Thr Leu Tyr Leu
            20                  25                  30

Tyr Ala Lys Asp Ile Ser Gly Pro Leu Lys Pro Gly Val Asp Thr Ile
        35                  40                  45

Glu Asn Val Val Lys Thr Val Thr Pro Val Tyr Tyr Ile Pro Leu
    50                  55                  60

Glu Ala Val Lys Phe Val Asp Lys Thr Val Asp Val Ser Val Thr Ser
65                  70                  75                  80

Leu Asp Gly Val Val Pro Pro Val Ile Lys Gln Val Ser Ala Gln Thr
                85                  90                  95

Tyr Ser Val Ala Gln Asp Ala Pro Arg Ile Val Leu Asp Val Ala Ser
            100                 105                 110

Ser Val Phe Asn Thr Gly Val Gln Glu Gly Ala Lys Ala Leu Tyr Ala
        115                 120                 125

Asn Leu Glu Pro Lys Ala Glu Gln Tyr Ala Val Ile Thr Trp Arg Ala
    130                 135                 140

Leu Asn Lys Leu Pro Leu Val Pro Gln Val Ala Asn Val Val Val Pro
145                 150                 155                 160

Thr Ala Val Tyr Phe Ser Glu Lys Tyr Asn Asp Val Val Arg Gly Thr
                165                 170                 175

Thr Glu Gln Gly Tyr Arg Val Ser Ser Tyr Leu Pro Leu Leu Pro Thr
            180                 185                 190

Glu Lys Ile Thr Lys Val Phe Gly Asp Glu Ala Ser
        195                 200

```
<210> SEQ ID NO 15
<211> LENGTH: 15
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (1)..(1)
<223> OTHER INFORMATION: n is a, c, g, or t

<400> SEQUENCE: 15
```
ntcgastwts gwgtt                                                    15

```
<210> SEQ ID NO 16
<211> LENGTH: 16
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (11)..(11)
<223> OTHER INFORMATION: n is a, c, g, or t

<400> SEQUENCE: 16
ngtcgtswga nawgaa                                                    16

<210> SEQ ID NO 17
<211> LENGTH: 15
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (5)..(5)
<223> OTHER INFORMATION: n is a, c, g, or t
<220> FEATURE:
<221> NAME/KEY: misc_feature
<222> LOCATION: (10)..(10)
<223> OTHER INFORMATION: n is a, c, g, or t
<220> FEATURE:
<221> NAME/KEY: misc_feature
<222> LOCATION: (13)..(13)
<223> OTHER INFORMATION: n is a, c, g, or t

<400> SEQUENCE: 17
wgtgnagwan canag                                                     15

<210> SEQ ID NO 18
<211> LENGTH: 15
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t

<400> SEQUENCE: 18
sttntastnc tntgc                                                     15

<210> SEQ ID NO 19
<211> LENGTH: 17
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (9)..(9)
<223> OTHER INFORMATION: n is a, c, g, or t
```

<400> SEQUENCE: 19
sstggstana twatwct                                                17

<210> SEQ ID NO 20
<211> LENGTH: 16
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (5)..(5)
<223> OTHER INFORMATION: n is a, c, g, or t
<220> FEATURE:
<221> NAME/KEY: misc_feature
<222> LOCATION: (10)..(10)
<223> OTHER INFORMATION: n is a, c, g, or t
<220> FEATURE:
<221> NAME/KEY: misc_feature
<222> LOCATION: (13)..(13)
<223> OTHER INFORMATION: n is a, c, g, or t

<400> SEQUENCE: 20
agwgnagwan canaga                                                 16

<210> SEQ ID NO 21
<211> LENGTH: 1565
<212> TYPE: DNA
<213> ORGANISM: Hevea brasiliensis

<400> SEQUENCE: 21
ctctgcttcg cacgagtagc gttctaaatc taccaaggat gattacgaaa ggggaagcaa     60
tccttccagg aatcaaaaaa agggacatgc caatgaatgc tcgttttatt accctacaag    120
tacagtgcaa ggttgggtca gtgaatagag ttattggcac agccatgttt cctgtttcta    180
attcttggga ggttatacac aagtgaattt tgagttacag gctgagggat gaaaagaatg    240
gaattgttac actgtatttg gtagggagaa agtaagaga ggaaagaaaa tataaagaaa     300
aaataagttt atttttttatt gttttgttta aattgaataa aaaataaaga agcgtaaaaa    360
tattaaaagg aaaataaaaa tattttatct ttttttcttt tctctttaa aatagagaaa     420 aatgagagga aaatatttaa aagtataaat ataactctat atttaataat tttttttaaa    480
atttaaaaat aaaattataa ttttattatt cataaaataa ttttttctca aatatttttc    540
tctttcaatc cagataaaaa gaaaaaaaat aattttttatt ttcattcttt attttctctc    600
ttttaatttt ctttctccct gaaatattcc caaacacagt gttaatgttt ttgtaaaaag    660
gggcaagcag tagcagatca cgtgagaaag aatttgccta gtattgcc cgtgttcttc      720 ctcgtcatcg ttgttgcggc caacctaatt tatcatggag gagtagtgcc agggatttca    780
cgtttggcgt acttctggtg cttaattaat ttatttgggg ttttgtattt taaaattagg    840
taaaatttct ataattttac aaaaattaac ttatttatt aaaaattaaa agatttagac     900
taaatagcaa aatcacgcaa tgggtttagt gttttaatac gagattagac ataataataa    960
taacacctga tggtcctcta ttttcaatta tttgccaact aaaccacaat caaccatgtt   1020
caacacaatt ggaattctac tgatatatca ttacagctgc caaaacattt atttaggcca   1080
ttaatcaatt ttaattgaac atgctatttt tctatcatca attcagcttc ttttttttata  1140 ttaatttaat ttataattaa cactaatgac aaaattagat attaaattta tgagaatgaa   1200
acataaaatt aatatataaa aaatatatta gttttaaaaa taattttaaa tattaaactc   1260

| | |
|---|---|
| aaaatattat atatatatat atatatatat atatatgaaa ttaaaattttt aaattaaaaa | 1320 |
| aatgcagtaa aaaaaaaaaa aataataaag tagctattgg atccaagggt ggtttagaac | 1380 |
| gctactcgtg cgaagcaaga gtgaggaaaa tgccaaggac ccgtcacgca cgccacatgt | 1440 |
| gtggggagga ggctcccgtt ctcgcattct tataaaaatg tcccagatcc aaatctcctg | 1500 |
| aaactaagct catcattccc tcttcctcct ctcccttttct ctctcctgcg ccggcatatt | 1560 |
| tttac | 1565 |

<210> SEQ ID NO 22
<211> LENGTH: 1352
<212> TYPE: DNA
<213> ORGANISM: Hevea brasiliensis

<400> SEQUENCE: 22

| | |
|---|---|
| gcagccggtt tggtctgaaa ttgcagatcc gagcgatgat cgaattttca cgaaataaaa | 60 |
| tgaaagtaca tacgcgaagt ccacaataac agggttagaa taatatatat atatatatat | 120 |
| atatatatta ttttttaaata attattatat atatataata ataattattt aaaaattaag | 180 |
| aatgttacac aagtgatgat atattgaaat tttataataa attaaataat cacatgtaaa | 240 |
| attaataaca tgtataaatt gagatattac ttttattcat gctatattta tttttttactt | 300 |
| taaaaattct ttttttttaa tataaaatta ttaaaatata aattcttaat tttctactta | 360 |
| taaaacatat actaatattg gaaactatta caatgtcatc tcattttat tattattatt | 420 |
| tttttttata gttcatcttc caattaaaaa gggtaattta caaaatcaca atgaaagaaa | 480 |
| tgatgatcat gactatataa taaattaatg atatttaagg taataaaaaa aaaacatgaa | 540 |
| agtaacataa caaaaagatt ataaaagagt cttgatgcac ataaggtaac atttccttcc | 600 |
| tcacaaaaat tttttttttt taatataaaa aataattttt ttataaatat aggtgaatca | 660 |
| gatgcacata atctctttaa catatatata tatatatata tctaagaaaa aagaaatcaa | 720 |
| gaatttatct tttatttccc cattgctaga aaatcagtgc agttactggc tcaacccatt | 780 |
| atactgtcag ggtttgcaat tgtggacttt ttatcatcaa tttaggcttt taatcaaccg | 840 |
| gataatctgg ttcattttttc cttatttttta agatacataa atgggagagt tactataaaa | 900 |
| ttcgattaga tttcaaatta aaataaaata ttttcttatt aaaaaagatt taaatttaaa | 960 |
| tttggttaga atcaaattga accaaagcag ataaatcaaa atagaatcaa agaattctat | 1020 |
| ggtctggtat caaaaaccgg ctcagaccaa accggctgcc agcctacttc cacaaccccca | 1080 |
| tatatcatag atgtcccttt acataaacgc aaaacaagaa cataaaaatg tctctcacca | 1140 |
| ctcgccttct aaatgcccac gtgggtagcg ccaccaccag actctcgtcc tcgcttccct | 1200 |
| cctctgcttc tcctcgttat tctcactttc tctctaccca atttgcctct ccttctctca | 1260 |
| ttcaattccc tctaactctt aaaccttcgt ctacctcttc gttatctagg gtattttcgt | 1320 |
| cttctccatc tgcaatcacc gctacttcca cc | 1352 |

<210> SEQ ID NO 23
<211> LENGTH: 533
<212> TYPE: DNA
<213> ORGANISM: Hevea brasiliensis

<400> SEQUENCE: 23

| | |
|---|---|
| cgtggctaga ttattctagg atttgggtat cgcataattt ttagttacta gtgtttagag | 60 |
| ttgcttatat ccaataactt cttaataaca attttaaata aaaaatattc ttgtgcgtat | 120 |
| caaaaaaatt taaaataaaa ccatgacata ttcaatttcc ttaactaggt taaaaatttt | 180 |

| | |
|---|---|
| tcatgcatta gcatatactt aatttgttga taaatagacc tttgatcaac tctcaacatg | 240 |
| accaaagtcc ctccttttt tagtataatt ggtttcaatt gaaagtcgaa ctctagactt | 300 |
| tatagtttat gaaatgattt caatactact gggttaatgc tcattggtca aagtactcac | 360 |
| agcagtatca agtagtcttt taaggttaaa aaaacttata tatatattaa cgaaagatgc | 420 |
| cacttgattt agtgtcacct ccgaaataat caacttaatt tagttattgg atctgagatt | 480 |
| ttatttttat atttttttc tgatgagcag gttaagtcag tggtttaagt aaa | 533 |

<210> SEQ ID NO 24
<211> LENGTH: 919
<212> TYPE: DNA
<213> ORGANISM: Hevea brasiliensis

<400> SEQUENCE: 24

| | |
|---|---|
| aaccgtccac caatctttga gttccagtga gtcatctact ggttgcttga cagatccatc | 60 |
| aataaaacca tatttctttt tggcccgtaa tgcagtcagc atagctcgcg cccattcttc | 120 |
| gtaattctcg cccttcaact gaacttgggt aatcaagtta tctgggttgt cattcgaatt | 180 |
| cagtgtttaa gaactaaaag ttttcttccc tgatccagaa ctctcatttt tcttttcatc | 240 |
| aaccatggct ctgataccat gtaaaaaaac taagaaattt tggaataaga attcttatct | 300 |
| ttattgcccc agaaataaaa tatatatata aaaaaattac agctaacaaa taggtcccta | 360 |
| atcaagctaa actaccaaaa ttgtatcaaa gtcatacaac aaaaggtaaa aacagatatg | 420 |
| cacacaaaaa ttcctaaaca aatgccctaa ataaatacaa aataagtgac agctaacagc | 480 |
| tgcatttcca ataattaatt taactaataa aatttataat cttaaaaata atttttaatat | 540 |
| tattgaatta aaatttataa ataaaattaa cactgttaaa attaaaagaa aattattaag | 600 |
| atttgaattt ttaagcggtt atttaatttt gaaaaacaag gctaacttt tttttatat | 660 |
| aatttactaa aaaattcatg aatgaaaaaa aaaaatccat aagtaaactt accccatacg | 720 |
| ggttatgcac gctaaaccaa taaaacagaa acacgtttat acactcgttt tcatttccat | 780 |
| ctataaatag agagatttgt ttttagtttt aaaccataat cagttgatag cttccacagt | 840 |
| gttttccgaa aggcaaatct tttttcaaac ttcagcgact gcgttttgaa tttgtgattt | 900 |
| ttaaaggaaa ttttcaatt | 919 |

<210> SEQ ID NO 25
<211> LENGTH: 984
<212> TYPE: DNA
<213> ORGANISM: Arabidopsis thaliana

<400> SEQUENCE: 25

| | |
|---|---|
| aacccacaaa ttgatctctt ctctcttctc ttacaccatc ttcttcattc accatgggaa | 60 |
| gatctccttg ttgtgaaaaa gctcacacaa acaaaggagc ttggactaaa gaagaagatc | 120 |
| aacgtctcgt agattatatc cgtaatcacg gtgaaggttg ttggcgttct cttcctaaat | 180 |
| ccgctggatt gttgcgttgt ggtaaaagtt gtagattgag atggattaat taccttcgtc | 240 |
| ctgatcttaa acgtggtaat tttactgatg atgaagatca aatcatcatc aaactccata | 300 |
| gcttactcgg taacaaatgg tcattgatag ctggaagatt accaggaaga acagataacg | 360 |
| aaataaagaa ttattggaac actcatatta agaggaagct tcttagtcac ggtattgatc | 420 |
| cacaaactca tcgtcagatt aacgaatcca aacggtgtc gtctcaagtt gttgttccta | 480 |
| ttcaaaacga tgccgttgag tattcttttt ccaatttagc cgttaaaccg aagacggaaa | 540 |

```
attcctccga taacggagct tcgactagcg gcacgacgac ggacgaggat ctccggcaga    600
atggggagtg ttattatagt gataattcag gacatataaa gctgaatttg gatttaactc    660
ttgggtttgg atcctggtcg ggtcggatag tcggagtcgg gtcatcggct gattctaaac    720
cgtggtgcga cccggtgatg gaggcgcgtt tgtcactgtt gtaataattt gtcaaaaaaa    780
tcccaaaaaa tgggttttgt tacttcattt ttttttttgc ttgagtcctt ttggataaat    840
atagaaattc tttacttcag tttctttggt atttttgttt tagttttttgt tcatattacc    900 ttttgaagaa aagaaaaaa aacgatacat ggtttccaaa taattttat ggaaatatat    960 aagaatatta caccattgtc tagg                                            984
```

<210> SEQ ID NO 26
<211> LENGTH: 236
<212> TYPE: PRT
<213> ORGANISM: Arabidopsis thaliana

<400> SEQUENCE: 26

```
Met Gly Arg Ser Pro Cys Cys Glu Lys Ala His Thr Asn Lys Gly Ala
1               5                   10                  15

Trp Thr Lys Glu Glu Asp Gln Arg Leu Val Asp Tyr Ile Arg Asn His
            20                  25                  30

Gly Glu Gly Cys Trp Arg Ser Leu Pro Lys Ser Ala Gly Leu Leu Arg
        35                  40                  45

Cys Gly Lys Ser Cys Arg Leu Arg Trp Ile Asn Tyr Leu Arg Pro Asp
    50                  55                  60

Leu Lys Arg Gly Asn Phe Thr Asp Asp Glu Asp Gln Ile Ile Ile Lys
65                  70                  75                  80

Leu His Ser Leu Leu Gly Asn Lys Trp Ser Leu Ile Ala Gly Arg Leu
                85                  90                  95

Pro Gly Arg Thr Asp Asn Glu Ile Lys Asn Tyr Trp Asn Thr His Ile
            100                 105                 110

Lys Arg Lys Leu Leu Ser His Gly Ile Asp Pro Gln Thr His Arg Gln
        115                 120                 125

Ile Asn Glu Ser Lys Thr Val Ser Ser Gln Val Val Pro Ile Gln
    130                 135                 140

Asn Asp Ala Val Glu Tyr Ser Phe Ser Asn Leu Ala Val Lys Pro Lys
145                 150                 155                 160

Thr Glu Asn Ser Ser Asp Asn Gly Ala Ser Thr Ser Gly Thr Thr Thr
                165                 170                 175

Asp Glu Asp Leu Arg Gln Asn Gly Glu Cys Tyr Tyr Ser Asp Asn Ser
            180                 185                 190

Gly His Ile Lys Leu Asn Leu Asp Leu Thr Leu Gly Phe Gly Ser Trp
        195                 200                 205

Ser Gly Arg Ile Val Gly Val Gly Ser Ser Ala Asp Ser Lys Pro Trp
    210                 215                 220

Cys Asp Pro Val Met Glu Ala Arg Leu Ser Leu Leu
225                 230                 235
```

<210> SEQ ID NO 27
<211> LENGTH: 1077
<212> TYPE: DNA
<213> ORGANISM: Arabidopsis thaliana

<400> SEQUENCE: 27

```
ctacaggaac tctcttcctt gcaaaaaaaa taaaacacta tttcctccaa atacacgtag    60
```

-continued

```
agagatacat atatacatat agagatcaac aaagatggga agatcaccat gctgcgagaa    120
agctcacatg aacaaggag cttggactaa agaagaagat cagcttcttg ttgattacat    180
ccgtaaacac ggtgaaggtt gctggcgatc tctccctcgc gccgctggat tacaaagatg    240
tggtaagagt tgtagattga gatggatgaa ttatctaaga ccagatctca aaagaggcaa    300
ttttactgaa gaagaagatg aactcatcat caagctccat agcttgctcg gtaacaaatg    360
gtctttaata gctgggagat taccaggaag aacagataac gagatcaaga actattggaa    420
cactcatatc aagaggaagc ttctcagccg tgggattgat ccaaactctc accgtctgat    480
caacgaatcc gtcgtgtctc cgtcgtctct tcaaaacgat gtcgttgaga ctatacatct    540
tgatttctct ggaccggtta aaccggaacc ggtgcgtgaa gagattggta tggttaataa    600
ttgtgagagt agtggaacga cgtcggagaa ggattatggg aacgaggaag attgggtgtt    660
gaatttggaa ctctctgttg gaccgagtta tcggtacgag tcgactcgga aagtgagtgt    720
tgttgactcg gctgagtcga ctcgacggtg gggttccgag ttgtttggag ctcatgagag    780
tgatgcggtg tgtttgtgtt gtcggattgg gttgtttcgt aatgagtcgt gtcggaattg    840
tcgggtttct gatgttagaa ctcattagag agtcaatcga gaattcttta ggaatctttt    900
tatatattta gatcgtcaat tgtgtttttt ttttgttcac atttgttatg taacatcaag    960
taagaaacta gcataattat ttgatggcaa agccaaaaga ttgtgctcaa agaaatttat   1020
aaaaacaaca attagggcat gttgtacttg cagatgctaa aaaacggtaa tttttat     1077
```

<210> SEQ ID NO 28
<211> LENGTH: 257
<212> TYPE: PRT
<213> ORGANISM: Arabidopsis thaliana

<400> SEQUENCE: 28

```
Met Gly Arg Ser Pro Cys Cys Glu Lys Ala His Met Asn Lys Gly Ala
1               5                   10                  15

Trp Thr Lys Glu Glu Asp Gln Leu Leu Val Asp Tyr Ile Arg Lys His
                20                  25                  30

Gly Glu Gly Cys Trp Arg Ser Leu Pro Arg Ala Ala Gly Leu Gln Arg
            35                  40                  45

Cys Gly Lys Ser Cys Arg Leu Arg Trp Met Asn Tyr Leu Arg Pro Asp
        50                  55                  60

Leu Lys Arg Gly Asn Phe Thr Glu Glu Glu Asp Glu Leu Ile Ile Lys
65                  70                  75                  80

Leu His Ser Leu Leu Gly Asn Lys Trp Ser Leu Ile Ala Gly Arg Leu
                85                  90                  95

Pro Gly Arg Thr Asp Asn Glu Ile Lys Asn Tyr Trp Asn Thr His Ile
            100                 105                 110

Lys Arg Lys Leu Leu Ser Arg Gly Ile Asp Pro Asn Ser His Arg Leu
        115                 120                 125

Ile Asn Glu Ser Val Val Ser Pro Ser Leu Gln Asn Asp Val Val
    130                 135                 140

Glu Thr Ile His Leu Asp Phe Ser Gly Pro Val Lys Pro Glu Pro Val
145                 150                 155                 160

Arg Glu Glu Ile Gly Met Val Asn Asn Cys Glu Ser Ser Gly Thr Thr
                165                 170                 175

Ser Glu Lys Asp Tyr Gly Asn Glu Glu Asp Trp Val Leu Asn Leu Glu
            180                 185                 190

Leu Ser Val Gly Pro Ser Tyr Arg Tyr Glu Ser Thr Arg Lys Val Ser
```

|  |  |  | 195 |  |  | 200 |  |  | 205 |  |  |
|--|--|--|--|--|--|--|--|--|--|--|--|

Val Val Asp Ser Ala Glu Ser Thr Arg Arg Trp Gly Ser Glu Leu Phe
    210                215                220

Gly Ala His Glu Ser Asp Ala Val Cys Leu Cys Cys Arg Ile Gly Leu
225                230                235              240

Phe Arg Asn Glu Ser Cys Arg Asn Cys Arg Val Ser Asp Val Arg Thr
              245                250              255

His

```
<210> SEQ ID NO 29
<211> LENGTH: 1636
<212> TYPE: DNA
<213> ORGANISM: Arabidopsis thaliana

<400> SEQUENCE: 29
ccttctttct tcttcactc tctcctgtct cctcttctca ctgtttccta tttcgtaatt      60
ttctcgagaa atcgtctttt cttgtttacg ctaatttgat ttctcgagaa aaaaaaaagg    120
aagcagaaga agattcttat tttatcttta cactgttcag aaatcttcgg tggacggata    180
acttgcagag ttctgattga ggtttctttt tcttttccct gttttctctt ggatcttgtt    240
tcttcatgtg cggactatac aaaaaactga ttcggtgaaa ttaatcagct ttatgctctg    300
ttttgttcgc tttcaggctg gttttgtgag aattatagtt gcagcaagaa agcgtttcag    360
atatttttta atggccgctg aggatcgaag tgaggaacta gcagcaatg tagaaaatgg     420
aagttgcaat tccaatgaag gaattaatcc tgaaaccagc agtcattgga ttgaaaacgt    480
tgtcaaggtt aggaaaccgt acacagtaac taagcagaga gagaagtgga gtgaggaaga    540
gcatgatagg tttcttgaag ctatcaagct ttatggtcgt ggttggcgtc aaatccaaga    600
acacataggt acaaaaaccg ctgtacagat acgaagccat gctcaaaagt tcttctccaa    660
gatggctcag gaagctgaca gtagaagtga aggatcggtt aaagcgattg tgatcccgcc    720
tcctcgtcca aagagaaaac cggcacatcc ttatcctcgg aaatcgcctg ttccatatac    780
tcagtctcct ccaccaaatt tgtcagctat ggagaaagga accaagtctc caacctcagt    840
gttatcatcg tttggttcag aggatcaagt caatagatgc tcttcgccta attcgtgtac    900
cagtgacatc caatccattg gtgcaacttc cattgataaa aagaataact acacaacatc    960
caagcaacct ttcaaagatg attctgacat tggttcaaca cccatttcaa gcattactct    1020
tttcgggaag attgtccttg tcgcggaaga atctcacaaa ccatcctctt acaatgatga    1080
tgatcttaaa caaatgacgt gtcaggagaa tcactactca gggatgctag ttgacactaa    1140
tttatctctt ggtgtatggg aaacgttttg tactggttct aatgcatttg gctcggttac    1200
agaagcatct gagaacttgg agaaaagtgc agagccgata agttcttcat ggaaacggtt    1260
aagctcctta gaaaaacaag gatcttgtaa tcctgtaaat gcaagtgggt tcaggccata    1320
caagagatgc ctatcagaaa gagaagtaac atcatcattg acgctggtag cttcagatga    1380
aaagaaaagc caaagagcac gtatatgcta gttttagcca ttgtacagtt tggagtcaat    1440
tttgatgatc cgtgaacatt gttttagcca tttgctgggt gacttggatc atagcattcc    1500
acgaaccaaa tcctaaatcc gagttggtaa gtggtttac ttgtccgcca catgtaattc    1560
ttgtaatgaa gtttctcctg ctgtctcacg ttaagaagac acttctttttt tcttcatat   1620
acaaatcagt tttaac                                                   1636

<210> SEQ ID NO 30
```

```
<211> LENGTH: 372
<212> TYPE: PRT
<213> ORGANISM: Arabidopsis thaliana

<400> SEQUENCE: 30

Met Leu Cys Phe Val Arg Phe Gln Ala Gly Phe Val Arg Ile Ile Val
1               5                   10                  15

Ala Ala Arg Lys Arg Phe Arg Tyr Phe Leu Met Ala Ala Glu Asp Arg
            20                  25                  30

Ser Glu Glu Leu Ser Ser Asn Val Glu Asn Gly Ser Cys Asn Ser Asn
        35                  40                  45

Glu Gly Ile Asn Pro Glu Thr Ser Ser His Trp Ile Glu Asn Val Val
    50                  55                  60

Lys Val Arg Lys Pro Tyr Thr Val Thr Lys Gln Arg Glu Lys Trp Ser
65                  70                  75                  80

Glu Glu Glu His Asp Arg Phe Leu Glu Ala Ile Lys Leu Tyr Gly Arg
                85                  90                  95

Gly Trp Arg Gln Ile Gln Glu His Ile Gly Thr Lys Thr Ala Val Gln
            100                 105                 110

Ile Arg Ser His Ala Gln Lys Phe Phe Ser Lys Met Ala Gln Glu Ala
        115                 120                 125

Asp Ser Arg Ser Glu Gly Ser Val Lys Ala Ile Val Ile Pro Pro Pro
    130                 135                 140

Arg Pro Lys Arg Lys Pro Ala His Pro Tyr Pro Arg Lys Ser Pro Val
145                 150                 155                 160

Pro Tyr Thr Gln Ser Pro Pro Asn Leu Ser Ala Met Glu Lys Gly
                165                 170                 175

Thr Lys Ser Pro Thr Ser Val Leu Ser Ser Phe Gly Ser Glu Asp Gln
            180                 185                 190

Val Asn Arg Cys Ser Ser Pro Asn Ser Cys Thr Ser Asp Ile Gln Ser
        195                 200                 205

Ile Gly Ala Thr Ser Ile Asp Lys Lys Asn Asn Tyr Thr Thr Ser Lys
    210                 215                 220

Gln Pro Phe Lys Asp Asp Ser Asp Ile Gly Ser Thr Pro Ile Ser Ser
225                 230                 235                 240

Ile Thr Leu Phe Gly Lys Ile Val Leu Val Ala Glu Glu Ser His Lys
                245                 250                 255

Pro Ser Ser Tyr Asn Asp Asp Leu Lys Gln Met Thr Cys Gln Glu
                260                 265                 270

Asn His Tyr Ser Gly Met Leu Val Asp Thr Asn Leu Ser Leu Gly Val
            275                 280                 285

Trp Glu Thr Phe Cys Thr Gly Ser Asn Ala Phe Gly Ser Val Thr Glu
        290                 295                 300

Ala Ser Glu Asn Leu Glu Lys Ser Ala Glu Pro Ile Ser Ser Ser Trp
305                 310                 315                 320

Lys Arg Leu Ser Ser Leu Glu Lys Gln Gly Ser Cys Asn Pro Val Asn
                325                 330                 335

Ala Ser Gly Phe Arg Pro Tyr Lys Arg Cys Leu Ser Glu Arg Glu Val
            340                 345                 350

Thr Ser Ser Leu Thr Leu Val Ala Ser Asp Glu Lys Lys Ser Gln Arg
        355                 360                 365

Ala Arg Ile Cys
    370
```

<210> SEQ ID NO 31
<211> LENGTH: 1728
<212> TYPE: DNA
<213> ORGANISM: Hevea brasiliensis

<400> SEQUENCE: 31

| | | | | | |
|---|---|---|---|---|---|
| atggacacca | ccggccggct | ccaccaccga | aagcatgcta | cacccgttga | ggaccgttct | 60 |
| ccgaccactc | cgaaagcgtc | ggacgcgctt | ccgcttcccc | tctacctgac | caacgcggtt | 120 |
| ttcttcacgc | tgttcttctc | ggtggcgtat | acctccttc | accggtggcg | cgacaagatc | 180 |
| cgcaactcca | ctccccttca | tatcgttact | ctctctgaaa | ttgttgctat | tgtctccctc | 240 |
| attgcctctt | tcatttacct | cctaggattc | ttcggtatcg | attttgtgca | gtcattcatt | 300 |
| gcacgcgcct | cccatgacgt | gtgggacctc | gaagatacgg | atcccaacta | cctcatcgat | 360 |
| gaagatcacc | gtctcgttac | ttgccctccc | gctaatatat | ctactaagac | taccattatt | 420 |
| gccgcaccta | ccaaattgcc | tacctcggaa | cccttaattg | cacccttagt | ctcggaggaa | 480 |
| gacgaaatga | tcgtcaactc | cgtcgtggat | gggaagatac | cctcctattc | tctggagtcg | 540 |
| aagctcgggg | actgcaaacg | agcggctgcg | attcgacgcg | aggctttgca | gaggatgaca | 600 |
| aggaggtcgc | tggaaggctt | gccagtagaa | gggttcgatt | acgagtcgat | tttaggacaa | 660 |
| tgctgtgaaa | tgccagtggg | atacgtgcag | attccggtgg | ggattgcggg | gccgttgttg | 720 |
| ctgaacgggc | gggagtactc | tgttccaatg | gcgaccacgg | agggttgttt | ggtggcgagc | 780 |
| actaatagag | ggtgtaaggc | gatttacttg | tcaggtgggg | ccaccagcgt | cttgttgaag | 840 |
| gatggcatga | caagagcgcc | tgttgtaaga | ttcgcgtcgg | cgactagagc | cgcggagttg | 900 |
| aagttcttct | tggaggatcc | tgacaatttt | gataccttgg | ccgtagtttt | taacaagtcc | 960 |
| agtagatttg | cgaggctcca | aggcattaaa | tgctcaattg | ctggtaagaa | tctttatata | 1020 |
| agattcagct | gcagcactgg | cgatgcaatg | gggatgaaca | tggtttctaa | aggggttcaa | 1080 |
| aacgttcttg | aatttcttca | aagtgatttt | tctgatatgg | atgtcattgg | aatctcagga | 1140 |
| aatttttgtt | cggataagaa | gcctgctgct | gtaaattgga | ttgaaggacg | tggcaaatca | 1200 |
| gttgtttgtg | aggcaattat | caaggaagag | gtggtgaaga | aggtgttgaa | accaatgtg | 1260 |
| gcctccctag | tggagcttaa | catgctcaag | aatcttgctg | gttctgctgt | tgctggtgct | 1320 |
| ttgggtggat | ttaatgccca | tgcaggcaac | atcgtatctg | caatctttat | tgccactggc | 1380 |
| caggatccag | cacagaatgt | tgagagttct | cattgcatta | ccatgatgga | agctgtcaat | 1440 |
| gatggaaagg | atctccatat | ctctgtgacc | atgccctcca | ttgaggtggg | tacagtcgga | 1500 |
| ggtggaactc | aacttgcatc | tcagtctgct | tgtctcaatt | tgcttggggt | gaagggtgca | 1560 |
| aacaaagagt | cgccaggatc | aaactcaagg | ctccttgctg | ccatcgtagc | tggttcagtt | 1620 |
| ttggctggtg | agctctcctt | gatgtctgcc | attgcagctg | ggcagcttgt | caagagtcac | 1680 |
| atgaagtaca | cagctccag | caaagatatg | tctaaagctg | catcttag | | 1728 |

<210> SEQ ID NO 32
<211> LENGTH: 575
<212> TYPE: PRT
<213> ORGANISM: Hevea brasiliensis

<400> SEQUENCE: 32

Met Asp Thr Thr Gly Arg Leu His His Arg Lys His Ala Thr Pro Val
1               5                   10                  15

Glu Asp Arg Ser Pro Thr Thr Pro Lys Ala Ser Asp Ala Leu Pro Leu
            20                  25                  30

-continued

Pro Leu Tyr Leu Thr Asn Ala Val Phe Phe Thr Leu Phe Ser Val
            35                  40                  45

Ala Tyr Tyr Leu Leu His Arg Trp Arg Asp Lys Ile Arg Asn Ser Thr
 50                  55                  60

Pro Leu His Ile Val Thr Leu Ser Glu Ile Val Ala Ile Val Ser Leu
 65                  70                  75                  80

Ile Ala Ser Phe Ile Tyr Leu Leu Gly Phe Phe Gly Ile Asp Phe Val
                85                  90                  95

Gln Ser Phe Ile Ala Arg Ala Ser His Asp Val Trp Asp Leu Glu Asp
            100                 105                 110

Thr Asp Pro Asn Tyr Leu Ile Asp Glu Asp His Arg Leu Val Thr Cys
            115                 120                 125

Pro Pro Ala Asn Ile Ser Thr Lys Thr Thr Ile Ile Ala Ala Pro Thr
130                 135                 140

Lys Leu Pro Thr Ser Glu Pro Leu Ile Ala Pro Leu Val Ser Glu Glu
145                 150                 155                 160

Asp Glu Met Ile Val Asn Ser Val Val Asp Gly Lys Ile Pro Ser Tyr
                165                 170                 175

Ser Leu Glu Ser Lys Leu Gly Asp Cys Lys Arg Ala Ala Ile Arg
            180                 185                 190

Arg Glu Ala Leu Gln Arg Met Thr Arg Arg Ser Leu Glu Gly Leu Pro
            195                 200                 205

Val Glu Gly Phe Asp Tyr Glu Ser Ile Leu Gly Gln Cys Cys Glu Met
            210                 215                 220

Pro Val Gly Tyr Val Gln Ile Pro Val Gly Ile Ala Gly Pro Leu Leu
225                 230                 235                 240

Leu Asn Gly Arg Glu Tyr Ser Val Pro Met Ala Thr Thr Glu Gly Cys
                245                 250                 255

Leu Val Ala Ser Thr Asn Arg Gly Cys Lys Ala Ile Tyr Leu Ser Gly
            260                 265                 270

Gly Ala Thr Ser Val Leu Leu Lys Asp Gly Met Thr Arg Ala Pro Val
            275                 280                 285

Val Arg Phe Ala Ser Ala Thr Arg Ala Ala Glu Leu Lys Phe Phe Leu
            290                 295                 300

Glu Asp Pro Asp Asn Phe Asp Thr Leu Ala Val Val Phe Asn Lys Ser
305                 310                 315                 320

Ser Arg Phe Ala Arg Leu Gln Gly Ile Lys Cys Ser Ile Ala Gly Lys
                325                 330                 335

Asn Leu Tyr Ile Arg Phe Ser Tyr Ser Thr Gly Asp Ala Met Gly Met
            340                 345                 350

Asn Met Val Ser Lys Gly Val Gln Asn Val Leu Glu Phe Leu Gln Ser
            355                 360                 365

Asp Phe Ser Asp Met Asp Val Ile Gly Ile Ser Gly Asn Phe Cys Ser
            370                 375                 380

Asp Lys Lys Pro Ala Ala Val Asn Trp Ile Glu Gly Arg Gly Lys Ser
385                 390                 395                 400

Val Val Cys Glu Ala Ile Ile Lys Glu Val Val Lys Val Leu
                405                 410                 415

Lys Thr Asn Val Ala Ser Leu Val Glu Leu Asn Met Leu Lys Asn Leu
            420                 425                 430

Ala Gly Ser Ala Val Ala Gly Ala Leu Gly Gly Phe Asn Ala His Ala
            435                 440                 445

Gly Asn Ile Val Ser Ala Ile Phe Ile Ala Thr Gly Gln Asp Pro Ala

```
            450                 455                 460
Gln Asn Val Glu Ser Ser His Cys Ile Thr Met Met Glu Ala Val Asn
465                 470                 475                 480

Asp Gly Lys Asp Leu His Ile Ser Val Thr Met Pro Ser Ile Glu Val
                485                 490                 495

Gly Thr Val Gly Gly Gly Thr Gln Leu Ala Ser Gln Ser Ala Cys Leu
            500                 505                 510

Asn Leu Leu Gly Val Lys Gly Ala Asn Lys Glu Ser Pro Gly Ser Asn
        515                 520                 525

Ser Arg Leu Leu Ala Ala Ile Val Ala Gly Ser Val Leu Ala Gly Glu
    530                 535                 540

Leu Ser Leu Met Ser Ala Ile Ala Ala Gly Gln Leu Val Lys Ser His
545                 550                 555                 560

Met Lys Tyr Asn Arg Ser Ser Lys Asp Met Ser Lys Ala Ala Ser
                565                 570                 575

<210> SEQ ID NO 33
<211> LENGTH: 15
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (1)..(1)
<223> OTHER INFORMATION: n is a, c, g, or t

<400> SEQUENCE: 33
ntcgastwts gwgtt                                                   15

<210> SEQ ID NO 34
<211> LENGTH: 16
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (11)..(11)
<223> OTHER INFORMATION: n is a, c, g, or t

<400> SEQUENCE: 34
ngtcgtswga nawgaa                                                  16

<210> SEQ ID NO 35
<211> LENGTH: 15
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (5)..(5)
<223> OTHER INFORMATION: n is a, c, g, or t
<220> FEATURE:
<221> NAME/KEY: misc_feature
<222> LOCATION: (10)..(10)
<223> OTHER INFORMATION: n is a, c, g, or t
<220> FEATURE:
<221> NAME/KEY: misc_feature
<222> LOCATION: (13)..(13)
<223> OTHER INFORMATION: n is a, c, g, or t
```

```
<400> SEQUENCE: 35
wgtgnagwan canag                                                    15

<210> SEQ ID NO 36
<211> LENGTH: 15
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t

<400> SEQUENCE: 36
sttntastnc tntgc                                                    15

<210> SEQ ID NO 37
<211> LENGTH: 17
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (9)..(9)
<223> OTHER INFORMATION: n is a, c, g, or t

<400> SEQUENCE: 37
sstggstana twatwct                                                  17

<210> SEQ ID NO 38
<211> LENGTH: 16
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (5)..(5)
<223> OTHER INFORMATION: n is a, c, g, or t
<220> FEATURE:
<221> NAME/KEY: misc_feature
<222> LOCATION: (10)..(10)
<223> OTHER INFORMATION: n is a, c, g, or t
<220> FEATURE:
<221> NAME/KEY: misc_feature
<222> LOCATION: (13)..(13)
<223> OTHER INFORMATION: n is a, c, g, or t

<400> SEQUENCE: 38
agwgnagwan canaga                                                   16

<210> SEQ ID NO 39
<211> LENGTH: 1565
<212> TYPE: DNA
<213> ORGANISM: Hevea brasiliensis

<400> SEQUENCE: 39
ctctgcttcg cacgagtagc gttctaaatc taccaaggat gattacgaaa ggggaagcaa    60
tccttccagg aatcaaaaaa agggacatgc caatgaatgc tcgttttatt accctacaag   120
```

| | |
|---|---|
| tacagtgcaa ggttgggtca gtgaatagag ttattggcac agccatgttt cctgtttcta | 180 |
| attcttggga ggttatacac aagtgaattt tgagttacag gctgagggat gaaaagaatg | 240 |
| gaattgttac actgtatttg gtagggagaa aagtaagaga ggaaagaaaa tataaagaaa | 300 |
| aaataagttt atttttttatt gttttgttta aattgaataa aaaataaaga agcgtaaaaa | 360 |
| tattaaaagg aaaataaaaa tattttatct ttttttttctt ttctctttaa aatagagaaa | 420 |
| aatgagagga aaatatttaa aagtataaat ataactctat atttaataat ttttttttaaa | 480 |
| atttaaaaat aaaattataa ttttattatt cataaaataa ttttttctca aatatttttc | 540 |
| tctttcaatc cagataaaaa gaaaaaaaat aatttttatt ttcattcttt attttctctc | 600 |
| ttttaattt ctttctccct gaaatattcc caaacacagt gttaatgttt ttgtaaaaag | 660 |
| gggcaagcag tagcagatca cgtgagaaag aatttgccta tagtattgcc cgtgttcttc | 720 |
| ctcgtcatcg ttgttgcggc caacctaatt tatcatggag gagtagtgcc agggatttca | 780 |
| cgtttggcgt acttctggtg cttaattaat ttatttgggg ttttgtattt taaaattagg | 840 |
| taaaatttct ataattttac aaaaattaac ttattttatt aaaaattaaa agatttagac | 900 |
| taaatagcaa aatcacgcaa tgggtttagt gttttaatac gagattagac ataataataa | 960 |
| taacacctga tggtcctcta ttttcaatta tttgccaact aaaccacaat caaccatgtt | 1020 |
| caacacaatt ggaattctac tgatatatca ttacagctgc caaaacattt atttaggcca | 1080 |
| ttaatcaatt ttaattgaac atgctatttt tctatcatca attcagcttc ttttttttata | 1140 |
| ttaatttaat ttataattaa cactaatgac aaaattagat attaaattta tgagaatgaa | 1200 |
| acataaaatt aatatataaa aaatatatta gttttaaaaa taattttaaa tattaaactc | 1260 |
| aaaatattat atatatatat atatatatat atatatgaaa ttaaaattttt aaattaaaaa | 1320 |
| aatgcagtaa aaaaaaaaaa aataataaag tagctattgg atccaagggt ggtttagaac | 1380 |
| gctactcgtg cgaagcaaga gtgaggaaaa tgccaaggac ccgtcacgca cgccacatgt | 1440 |
| gtggggagga ggctcccgtt ctcgcattct tataaaaatg tcccagatcc aaatctcctg | 1500 |
| aaactaagct catcattccc tcttcctcct ctcccttct ctctcctgcg ccggcatatt | 1560 |
| tttac | 1565 |

<210> SEQ ID NO 40
<211> LENGTH: 2202
<212> TYPE: DNA
<213> ORGANISM: Arabidopsis thaliana

<400> SEQUENCE: 40

| | |
|---|---|
| cagtgttttg tgattatata cagtgtacac acacctaaaa taagtatcca taaagagatt | 60 |
| tggtcattcg gacaccgtcc ttttctctca actcaaagct caattcaacc acaacgata | 120 |
| gtaacttgaa agtcacaaat atttaatatt ttcccattat agaaggttaa aaaaaataaa | 180 |
| tatattctgg gttttgttgt cttcttcttt cttcctcagg aaaccaaacc aatgtcataa | 240 |
| acaatggcaa ccggagaaaa cagaacggtg ccggacaatc taaagaaaca gctcgcagtt | 300 |
| tcagttcgaa acattcaatg gagttatgga atcttctggt ctgtctctgc ttctcaacca | 360 |
| ggagtgttgg agtggggaga tggatattac aatggagaca taaagacaag gaagacgatt | 420 |
| caagcagcag aagtcaaaat tgaccagtta ggtcttgaga gaagtgagca gcttagagag | 480 |
| ctttatgaat ctctctccct cgctgaatcc tcagcttccg gtagctctca ggtcactaga | 540 |
| cgagcttccg ccgccgctct ctcaccggag gacctcaccg acaccgagtg gtactactta | 600 |

-continued

```
gtatgcatgt ctttcgtctt caacatcggt gaaggaatcc ccggaggagc gttatccaat      660
ggagaaccaa tatggctttg taacgctgaa accgccgata gcaaagtctt cactcgttct      720
cttctagcta aaagtgcttc gcttcagaca gtggttttgct tcccgtttct tggaggagtc     780
cttgagattg gcacgaccga acatattaaa gaggacatga acgtgataca aagtgttaag      840
acgttgttcc ttgaagctcc tccatatact acaatatcga caagatcaga ctatcaagaa      900
atttttgatc ccttaagtga cgataaatac actccggtgt ttataaccga agcttttcca      960
acaacttcta ctagcgggtt tgagcaagaa cctgaggatc atgattcgtt catcaacgat     1020
ggtggtgcgt ctcaggtaca aagctggcag tttgtgggtg aagaaatcag taactgcatt     1080
caccaatcgt taaattcaag cgattgcgtt tcccaaacgt tgttggaac aaccgggaga      1140 cttgcttgcg atccaaggaa gagtaggatt caacggttag gtcagattca agaacagagt     1200
aaccatgtaa atatggacga cgatgttcat taccaaggcg tgatatcgac gattttcaaa    1260
acaacgcatc agctaatact cggaccgcag tttcagaact tcgataagcg gtctagcttc    1320
acaaggtgga agcgatcatc atctgtgaaa acattgggag agaaatcgca gaagatgata    1380
aagaagatac tcttcgaggt tcctttgatg aacaagaaag aagagttgtt accggacaca    1440
ccagaggaaa ccgggaacca tgccttgtcc gagaagaaac gccgcgagaa attgaatgaa    1500
cggtttatga cattgagatc aatcattccc tcaattagta agattgataa agtgtcgatt    1560
cttgatgata caattgagta tcttcaagat ttacagaaac gggttcaaga gttggaatct    1620
tgtagagaat ctgctgatac agagacacgg ataacgatga tgaagaggaa gaaaccggat    1680
gatgaggagg aaagagcatc agcgaattgt atgaacagca aaaggaaggg gagtgatgtg    1740
aatgtaggag aagatgaacc agctgatatc ggttatgctg gtctaacgga taacttaagg    1800
atcagttcat taggtaacga ggtggttatt gagcttagat gcgcttggag agaagggata    1860
ttgcttgaga taatggatgt gattagtgat ctcaacttgg attctcactc ggttcagtcg    1920
tcaaccggag acggtttact ctgcttaact gtcaattgca agcataaagg gacaaaaata    1980
gcaacaacag gaatgatcca agaggcactt caaagggttg catggatatg ttaaggattc    2040
aaggtttaga tttgacaaaa ttagcttttt ctctggtttg gtttcccaat tttcggtaat    2100
cagtgattct aaccgagttt ttgtgatttt gaagttttgg aagatcctta agaattcttg    2160
aaaaatcgtt cctttttggct cattacgtag gagaagacaa ta                      2202
```

<210> SEQ ID NO 41
<211> LENGTH: 596
<212> TYPE: PRT
<213> ORGANISM: Arabidopsis thaliana

<400> SEQUENCE: 41

```
Met Ala Thr Gly Glu Asn Arg Thr Val Pro Asp Asn Leu Lys Lys Gln
1               5                   10                  15

Leu Ala Val Ser Val Arg Asn Ile Gln Trp Ser Tyr Gly Ile Phe Trp
            20                  25                  30

Ser Val Ser Ala Ser Gln Pro Gly Val Leu Glu Trp Gly Asp Gly Tyr
        35                  40                  45

Tyr Asn Gly Asp Ile Lys Thr Arg Lys Thr Ile Gln Ala Ala Glu Val
    50                  55                  60

Lys Ile Asp Gln Leu Gly Leu Glu Arg Ser Glu Gln Leu Arg Glu Leu
65                  70                  75                  80

Tyr Glu Ser Leu Ser Leu Ala Glu Ser Ser Ala Ser Gly Ser Ser Gln
                85                  90                  95
```

-continued

Val Thr Arg Arg Ala Ser Ala Ala Ala Leu Ser Pro Glu Asp Leu Thr
            100                 105                 110

Asp Thr Glu Trp Tyr Tyr Leu Val Cys Met Ser Phe Val Phe Asn Ile
            115                 120                 125

Gly Glu Gly Ile Pro Gly Gly Ala Leu Ser Asn Gly Glu Pro Ile Trp
            130                 135                 140

Leu Cys Asn Ala Glu Thr Ala Asp Ser Lys Val Phe Thr Arg Ser Leu
145                 150                 155                 160

Leu Ala Lys Ser Ala Ser Leu Gln Thr Val Val Cys Phe Pro Phe Leu
                165                 170                 175

Gly Gly Val Leu Glu Ile Gly Thr Thr Glu His Ile Lys Glu Asp Met
            180                 185                 190

Asn Val Ile Gln Ser Val Lys Thr Leu Phe Leu Glu Ala Pro Pro Tyr
                195                 200                 205

Thr Thr Ile Ser Thr Arg Ser Asp Tyr Gln Glu Ile Phe Asp Pro Leu
            210                 215                 220

Ser Asp Asp Lys Tyr Thr Pro Val Phe Ile Thr Glu Ala Phe Pro Thr
225                 230                 235                 240

Thr Ser Thr Ser Gly Phe Glu Gln Glu Pro Glu Asp His Asp Ser Phe
                245                 250                 255

Ile Asn Asp Gly Gly Ala Ser Gln Val Gln Ser Trp Gln Phe Val Gly
            260                 265                 270

Glu Glu Ile Ser Asn Cys Ile His Gln Ser Leu Asn Ser Ser Asp Cys
            275                 280                 285

Val Ser Gln Thr Phe Val Gly Thr Thr Gly Arg Leu Ala Cys Asp Pro
            290                 295                 300

Arg Lys Ser Arg Ile Gln Arg Leu Gly Gln Ile Gln Glu Gln Ser Asn
305                 310                 315                 320

His Val Asn Met Asp Asp Val His Tyr Gln Gly Val Ile Ser Thr
                325                 330                 335

Ile Phe Lys Thr Thr His Gln Leu Ile Leu Gly Pro Gln Phe Gln Asn
            340                 345                 350

Phe Asp Lys Arg Ser Ser Phe Thr Arg Trp Lys Arg Ser Ser Ser Val
            355                 360                 365

Lys Thr Leu Gly Glu Lys Ser Gln Lys Met Ile Lys Lys Ile Leu Phe
            370                 375                 380

Glu Val Pro Leu Met Asn Lys Lys Glu Glu Leu Leu Pro Asp Thr Pro
385                 390                 395                 400

Glu Glu Thr Gly Asn His Ala Leu Ser Glu Lys Lys Arg Arg Glu Lys
                405                 410                 415

Leu Asn Glu Arg Phe Met Thr Leu Arg Ser Ile Pro Ser Ile Ser
            420                 425                 430

Lys Ile Asp Lys Val Ser Ile Leu Asp Asp Thr Ile Glu Tyr Leu Gln
            435                 440                 445

Asp Leu Gln Lys Arg Val Gln Glu Leu Glu Ser Cys Arg Glu Ser Ala
            450                 455                 460

Asp Thr Glu Thr Arg Ile Thr Met Met Lys Arg Lys Pro Asp Asp
465                 470                 475                 480

Glu Glu Glu Arg Ala Ser Ala Asn Cys Met Asn Ser Lys Arg Lys Gly
                485                 490                 495

Ser Asp Val Asn Val Gly Glu Asp Glu Pro Ala Asp Ile Gly Tyr Ala
            500                 505                 510

```
Gly Leu Thr Asp Asn Leu Arg Ile Ser Ser Leu Gly Asn Glu Val Val
            515                 520                 525

Ile Glu Leu Arg Cys Ala Trp Arg Gly Ile Leu Leu Glu Ile Met
        530                 535                 540

Asp Val Ile Ser Asp Leu Asn Leu Asp Ser His Ser Val Gln Ser Ser
545                 550                 555                 560

Thr Gly Asp Gly Leu Leu Cys Leu Thr Val Asn Cys Lys His Lys Gly
                565                 570                 575

Thr Lys Ile Ala Thr Thr Gly Met Ile Gln Glu Ala Leu Gln Arg Val
            580                 585                 590

Ala Trp Ile Cys
        595

<210> SEQ ID NO 42
<211> LENGTH: 1201
<212> TYPE: DNA
<213> ORGANISM: Arabidopsis thaliana

<400> SEQUENCE: 42
aagattcccc aattcgtctc ctccaacagt tttcttcttc tcttcttctt tgggtgttcc      60
ttccaccaac ggcagaaatc gatttggctt aaatctcccc ctcctttcga tctctctgat    120
cgccgccggg aacattcaat ttcccgggag ttcaacaaaa aaaaaactct ccgttttat     180
ttttcccccct ttttcaccgg tggaagtttc cggagatggt gtcacccgaa acgctaatt    240
ggatttgtga cttgatcgat gctgattacg gaagtttcac aatccaaggt cctggtttct    300
cttggcctgt tcagcaacct attggtgttt cttctaactc cagtgctgga gttgatggct    360
cggctggaaa ctcagaagct agcaaagaac ctggatccaa aagagggggg agatgtgaat    420
catcctctgc cactagctcg aaagcatgta gagagaagca gcgacgggac aggttgaatg    480
acaagtttat ggaattgggt gcaattttgg agcctggaaa tcctcccaaa acagacaagg    540
ctgctatctt ggttgatgct gtccgcatgg tgacacagct acggggcgag gcccagaagc    600
tgaaggactc caattcaagt cttcaggaca aaatcaaaga gttaaagact gagaaaaacg    660
agctgcgaga tgagaaacag aggctgaaga cagagaaaga aaagctggag cagcagctga    720
aagccatgaa tgctcctcaa ccaagttttt tcccagcccc acctatgatg cctactgctt    780
ttgcttcagc gcaaggccaa gctcctggaa acaagatggt gccaatcatc agttacccag    840
gagttgccat gtggcagttc atgcctcctg cttcagtcga tacttctcag gatcatgtcc    900
ttcgtcctcc tgttgcttaa tcaagaaaaa tcatcaaccg gtttgcttct gcttccgct    960
taaaagaaaa gtctccattt gttttgctct cctctctttc tcggctttct tagtcttatc   1020
cttttgcttt gtcgtgttat catcgtaact gttatctgtt gaacaatgat atgacattgt   1080
aaactccaat tgcttcgcgc aatgttatct attcacatgt aaatttaagt agagtttggc   1140
agatcgtctc tcactttatg tgttcttaca ttaatacata gaatgtggtt acttcctcgc   1200
c                                                                   1201

<210> SEQ ID NO 43
<211> LENGTH: 234
<212> TYPE: PRT
<213> ORGANISM: Arabidopsis thaliana

<400> SEQUENCE: 43

Met Val Ser Pro Glu Asn Ala Asn Trp Ile Cys Asp Leu Ile Asp Ala
1               5                   10                  15
```

```
Asp Tyr Gly Ser Phe Thr Ile Gln Gly Pro Gly Phe Ser Trp Pro Val
             20                  25                  30

Gln Gln Pro Ile Gly Val Ser Ser Asn Ser Ser Ala Gly Val Asp Gly
         35                  40                  45

Ser Ala Gly Asn Ser Glu Ala Ser Lys Glu Pro Gly Ser Lys Lys Arg
 50                  55                  60

Gly Arg Cys Glu Ser Ser Ala Thr Ser Ser Lys Ala Cys Arg Glu
65              70                  75                  80

Lys Gln Arg Arg Asp Arg Leu Asn Asp Lys Phe Met Glu Leu Gly Ala
                 85                  90                  95

Ile Leu Glu Pro Gly Asn Pro Pro Lys Thr Asp Lys Ala Ala Ile Leu
            100                 105                 110

Val Asp Ala Val Arg Met Val Thr Gln Leu Arg Gly Glu Ala Gln Lys
            115                 120                 125

Leu Lys Asp Ser Asn Ser Ser Leu Gln Asp Lys Ile Lys Glu Leu Lys
            130                 135                 140

Thr Glu Lys Asn Glu Leu Arg Asp Glu Lys Gln Arg Leu Lys Thr Glu
145                 150                 155                 160

Lys Glu Lys Leu Glu Gln Gln Leu Lys Ala Met Asn Ala Pro Gln Pro
                165                 170                 175

Ser Phe Phe Pro Ala Pro Pro Met Met Pro Thr Ala Phe Ala Ser Ala
            180                 185                 190

Gln Gly Gln Ala Pro Gly Asn Lys Met Val Pro Ile Ile Ser Tyr Pro
            195                 200                 205

Gly Val Ala Met Trp Gln Phe Met Pro Pro Ala Ser Val Asp Thr Ser
            210                 215                 220

Gln Asp His Val Leu Arg Pro Pro Val Ala
225                 230

<210> SEQ ID NO 44
<211> LENGTH: 1253
<212> TYPE: DNA
<213> ORGANISM: Arabidopsis thaliana

<400> SEQUENCE: 44
taagtgggtc accaatgtag ctgacaacta taccatctat ctgatccgat cgctcttata      60
acataagcgt atgggatacc attttctcgg acaaagctga atccctaaa gaaaaaacac     120 ttctccaaac ttttcatctc cgatatctct taactaaca tgtcgaataa tcaagctttc     180
atggaattgg gatggagaaa cgacgtcgga tcacttgctg tgaaagatca gggcatgatg     240
tcagaaagag caagaagtga tgaagatcgt ctaatcaacg gtctaaaatg gggctacggc     300
tactttgatc atgatcaaac tgataattat cttcagattg ttccagagat tcataaagaa     360
gtagaaaatg cgaaggagga tttattggtt gttgtccctg atgaacattc tgaaactgat     420
gatcatcatc atattaaaga tttttcagag agatcagatc atcgatttta tctgagaaac     480
aaacatgaga accccaaaaa acgtcgtatc caggtcttaa gtagtgatga tgaatcggag     540
gagtttacaa gagaagttcc ttcagttact cgaaaaggtt ccaagagaag aagaagagac     600
gagaagatga gtaataagat gcgtaagcta cagcaactcg tacctaattg tcacaagacg     660
gacaaggttt cggttctcga caagaccata gagtatatga aaaaccttca acttcaactt     720
cagatgatgt caacagtggg ggtgaatcct tattttcttc cggcgacatt aggatttgga     780
atgcacaacc acatgctgac ggcaatggct tcggctcacg gcctaaatcc ggcgaatcac     840
atgatgccat cgccgctaat tccggcgtta aattggccat taccaccgtt tactaatatt     900
```

-continued

```
tcattcccac attcatctag tcaatctcta tttcttacaa catcatcacc agcttcttct    960
cctcagtctc ttcacggttt ggttccttat ttcccaagtt tcttggattt ttcttcccat   1020
gcgatgagaa gactatgata agtaagtagc tcgataaaag tttatgtgaa atgatcgttg   1080
actaattaag agagaaaaga gttccaaatt aggacagttt gtgtgaacca tttgtgtcat   1140
atactttttt ttccgggtgg ttttgtatat taataataat caataagtta aaacttttg    1200 tataaattct tgcatgtaac aatttttca tttatctgat attttgtaaa ata           1253
```

<210> SEQ ID NO 45
<211> LENGTH: 292
<212> TYPE: PRT
<213> ORGANISM: Arabidopsis thaliana

<400> SEQUENCE: 45

```
Met Ser Asn Asn Gln Ala Phe Met Glu Leu Gly Trp Arg Asn Asp Val
1               5                   10                  15

Gly Ser Leu Ala Val Lys Asp Gln Gly Met Met Ser Glu Arg Ala Arg
            20                  25                  30

Ser Asp Glu Asp Arg Leu Ile Asn Gly Leu Lys Trp Gly Tyr Gly Tyr
        35                  40                  45

Phe Asp His Asp Gln Thr Asp Asn Tyr Leu Gln Ile Val Pro Glu Ile
    50                  55                  60

His Lys Glu Val Glu Asn Ala Lys Glu Asp Leu Val Val Val Pro
65                  70                  75                  80

Asp Glu His Ser Glu Thr Asp His His Ile Lys Asp Phe Ser
                85                  90                  95

Glu Arg Ser Asp His Arg Phe Tyr Leu Arg Asn Lys His Glu Asn Pro
            100                 105                 110

Lys Lys Arg Arg Ile Gln Val Leu Ser Ser Asp Asp Glu Ser Glu Glu
        115                 120                 125

Phe Thr Arg Glu Val Pro Ser Val Thr Arg Lys Gly Ser Lys Arg Arg
    130                 135                 140

Arg Arg Asp Glu Lys Met Ser Asn Lys Met Arg Lys Leu Gln Gln Leu
145                 150                 155                 160

Val Pro Asn Cys His Lys Thr Asp Lys Val Ser Val Leu Asp Lys Thr
                165                 170                 175

Ile Glu Tyr Met Lys Asn Leu Gln Leu Gln Leu Gln Met Met Ser Thr
            180                 185                 190

Val Gly Val Asn Pro Tyr Phe Leu Pro Ala Thr Leu Gly Phe Gly Met
        195                 200                 205

His Asn His Met Leu Thr Ala Met Ala Ser Ala His Gly Leu Asn Pro
    210                 215                 220

Ala Asn His Met Met Pro Ser Pro Leu Ile Pro Ala Leu Asn Trp Pro
225                 230                 235                 240

Leu Pro Pro Phe Thr Asn Ile Ser Phe Pro His Ser Ser Ser Gln Ser
                245                 250                 255

Leu Phe Leu Thr Thr Ser Ser Pro Ala Ser Pro Gln Ser Leu His
            260                 265                 270

Gly Leu Val Pro Tyr Phe Pro Ser Phe Leu Asp Phe Ser Ser His Ala
        275                 280                 285

Met Arg Arg Leu
    290
```

<210> SEQ ID NO 46
<211> LENGTH: 1728
<212> TYPE: DNA
<213> ORGANISM: Hevea brasiliensis

<400> SEQUENCE: 46

| | | | | | |
|---|---|---|---|---|---|
| atggacacca | ccggccggct | ccaccaccga | aagcatgcta | cacccgttga | ggaccgttct | 60 |
| ccgaccactc | cgaaagcgtc | ggacgcgctt | ccgcttcccc | tctacctgac | caacgcggtt | 120 |
| ttcttcacgc | tgttcttctc | ggtggcgtat | acctccttc | accggtggcg | cgacaagatc | 180 |
| cgcaactcca | ctccccttca | tatcgttact | ctctctgaaa | ttgttgctat | tgtctccctc | 240 |
| attgcctctt | tcatttacct | cctaggattc | ttcggtatcg | attttgtgca | gtcattcatt | 300 |
| gcacgcgcct | cccatgacgt | gtgggacctc | gaagatacgg | atcccaacta | cctcatcgat | 360 |
| gaagatcacc | gtctcgttac | ttgccctccc | gctaatatat | ctactaagac | taccattatt | 420 |
| gccgcaccta | ccaaattgcc | tacctcggaa | cccttaattg | cacccttagt | ctcggaggaa | 480 |
| gacgaaatga | tcgtcaactc | cgtcgtggat | gggaagatac | cctcctattc | tctggagtcg | 540 |
| aagctcgggg | actgcaaacg | agcggctgcg | attcgacgcg | aggctttgca | gaggatgaca | 600 |
| aggaggtcgc | tggaaggctt | gccagtagaa | gggttcgatt | acgagtcgat | tttaggacaa | 660 |
| tgctgtgaaa | tgccagtggg | atacgtgcag | attccggtgg | ggattgcggg | gccgttgttg | 720 |
| ctgaacgggc | gggagtactc | tgttccaatg | gcgaccacgg | agggttgttt | ggtggcgagc | 780 |
| actaatagag | ggtgtaaggc | gatttacttg | tcaggtgggg | ccaccagcgt | cttgttgaag | 840 |
| gatggcatga | caagagcgcc | tgttgtaaga | ttcgcgtcgg | cgactagagc | cgcggagttg | 900 |
| aagttcttct | tggaggatcc | tgacaatttt | gataccttgg | ccgtagtttt | taacaagtcc | 960 |
| agtagatttg | cgaggctcca | aggcattaaa | tgctcaattg | ctggtaagaa | tctttatata | 1020 |
| agattcagct | gcagcactgg | cgatgcaatg | gggatgaaca | tggtttctaa | aggggttcaa | 1080 |
| aacgttcttg | aatttcttca | aagtgatttt | tctgatatgg | atgtcattgg | aatctcagga | 1140 |
| aattttgtt | cggataagaa | gcctgctgct | gtaaattgga | ttgaaggacg | tggcaaatca | 1200 |
| gttgtttgtg | aggcaattat | caaggaagag | gtggtgaaga | aggtgttgaa | aaccaatgtg | 1260 |
| gcctccctag | tggagcttaa | catgctcaag | aatcttgctg | gttctgctgt | tgctggtgct | 1320 |
| ttgggtggat | ttaatgccca | tgcaggcaac | atcgtatctg | caatctttat | tgccactggc | 1380 |
| caggatccag | cacagaatgt | tgagagttct | cattgcatta | ccatgatgga | agctgtcaat | 1440 |
| gatggaaagg | atctccatat | ctctgtgacc | atgccctcca | ttgaggtggg | tacagtcgga | 1500 |
| ggtggaactc | aacttgcatc | tcagtctgct | tgtctcaatt | tgcttggggt | gaagggtgca | 1560 |
| aacaaagagt | cgccaggatc | aaactcaagg | ctccttgctg | ccatcgtagc | tggttcagtt | 1620 |
| ttggctggtg | agctctcctt | gatgtctgcc | attgcagctg | ggcagcttgt | caagagtcac | 1680 |
| atgaagtaca | acagctccag | caaagatatg | tctaaagctg | catcttag | | 1728 |

<210> SEQ ID NO 47
<211> LENGTH: 575
<212> TYPE: PRT
<213> ORGANISM: Hevea brasiliensis

<400> SEQUENCE: 47

Met Asp Thr Thr Gly Arg Leu His His Arg Lys His Ala Thr Pro Val
1               5                   10                  15

Glu Asp Arg Ser Pro Thr Thr Pro Lys Ala Ser Asp Ala Leu Pro Leu
            20                  25                  30

```
Pro Leu Tyr Leu Thr Asn Ala Val Phe Phe Thr Leu Phe Ser Val
         35                  40                  45

Ala Tyr Tyr Leu Leu His Arg Trp Arg Asp Lys Ile Arg Asn Ser Thr
 50                  55                  60

Pro Leu His Ile Val Thr Leu Ser Glu Ile Val Ala Ile Val Ser Leu
 65                  70                  75                  80

Ile Ala Ser Phe Ile Tyr Leu Leu Gly Phe Phe Gly Ile Asp Phe Val
                 85                  90                  95

Gln Ser Phe Ile Ala Arg Ala Ser His Asp Val Trp Asp Leu Glu Asp
            100                 105                 110

Thr Asp Pro Asn Tyr Leu Ile Asp Glu Asp His Arg Leu Val Thr Cys
        115                 120                 125

Pro Pro Ala Asn Ile Ser Thr Lys Thr Thr Ile Ile Ala Ala Pro Thr
    130                 135                 140

Lys Leu Pro Thr Ser Glu Pro Leu Ile Ala Pro Leu Val Ser Glu Glu
145                 150                 155                 160

Asp Glu Met Ile Val Asn Ser Val Val Asp Gly Lys Ile Pro Ser Tyr
                165                 170                 175

Ser Leu Glu Ser Lys Leu Gly Asp Cys Lys Arg Ala Ala Ile Arg
            180                 185                 190

Arg Glu Ala Leu Gln Arg Met Thr Arg Arg Ser Leu Glu Gly Leu Pro
        195                 200                 205

Val Glu Gly Phe Asp Tyr Glu Ser Ile Leu Gly Gln Cys Cys Glu Met
    210                 215                 220

Pro Val Gly Tyr Val Gln Ile Pro Val Gly Ile Ala Gly Pro Leu Leu
225                 230                 235                 240

Leu Asn Gly Arg Glu Tyr Ser Val Pro Met Ala Thr Thr Glu Gly Cys
                245                 250                 255

Leu Val Ala Ser Thr Asn Arg Gly Cys Lys Ala Ile Tyr Leu Ser Gly
            260                 265                 270

Gly Ala Thr Ser Val Leu Leu Lys Asp Gly Met Thr Arg Ala Pro Val
        275                 280                 285

Val Arg Phe Ala Ser Ala Thr Arg Ala Ala Glu Leu Lys Phe Phe Leu
    290                 295                 300

Glu Asp Pro Asp Asn Phe Asp Thr Leu Ala Val Val Phe Asn Lys Ser
305                 310                 315                 320

Ser Arg Phe Ala Arg Leu Gln Gly Ile Lys Cys Ser Ile Ala Gly Lys
                325                 330                 335

Asn Leu Tyr Ile Arg Phe Ser Tyr Ser Thr Gly Asp Ala Met Gly Met
            340                 345                 350

Asn Met Val Ser Lys Gly Val Gln Asn Val Leu Glu Phe Leu Gln Ser
        355                 360                 365

Asp Phe Ser Asp Met Asp Val Ile Gly Ile Ser Gly Asn Phe Cys Ser
    370                 375                 380

Asp Lys Lys Pro Ala Ala Val Asn Trp Ile Glu Gly Arg Gly Lys Ser
385                 390                 395                 400

Val Val Cys Glu Ala Ile Ile Lys Glu Val Val Lys Lys Val Leu
                405                 410                 415

Lys Thr Asn Val Ala Ser Leu Val Glu Leu Asn Met Leu Lys Asn Leu
            420                 425                 430

Ala Gly Ser Ala Val Ala Gly Ala Leu Gly Gly Phe Asn Ala His Ala
        435                 440                 445

Gly Asn Ile Val Ser Ala Ile Phe Ile Ala Thr Gly Gln Asp Pro Ala
```

```
                    450                 455                 460
Gln Asn Val Glu Ser Ser His Cys Ile Thr Met Met Glu Ala Val Asn
465                 470                 475                 480

Asp Gly Lys Asp Leu His Ile Ser Val Thr Met Pro Ser Ile Glu Val
                485                 490                 495

Gly Thr Val Gly Gly Thr Gln Leu Ala Ser Gln Ser Ala Cys Leu
            500                 505                 510

Asn Leu Leu Gly Val Lys Gly Ala Asn Lys Glu Ser Pro Gly Ser Asn
            515                 520                 525

Ser Arg Leu Leu Ala Ala Ile Val Ala Gly Ser Val Leu Ala Gly Glu
        530                 535                 540

Leu Ser Leu Met Ser Ala Ile Ala Ala Gly Gln Leu Val Lys Ser His
545                 550                 555                 560

Met Lys Tyr Asn Arg Ser Ser Lys Asp Met Ser Lys Ala Ala Ser
                565                 570                 575

<210> SEQ ID NO 48
<211> LENGTH: 15
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (1)..(1)
<223> OTHER INFORMATION: n is a, c, g, or t

<400> SEQUENCE: 48
ntcgastwts gwgtt                                                          15

<210> SEQ ID NO 49
<211> LENGTH: 16
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (11)..(11)
<223> OTHER INFORMATION: n is a, c, g, or t

<400> SEQUENCE: 49
ngtcgtswga nawgaa                                                         16

<210> SEQ ID NO 50
<211> LENGTH: 15
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (5)..(5)
<223> OTHER INFORMATION: n is a, c, g, or t
<220> FEATURE:
<221> NAME/KEY: misc_feature
<222> LOCATION: (10)..(10)
<223> OTHER INFORMATION: n is a, c, g, or t
<220> FEATURE:
<221> NAME/KEY: misc_feature
<222> LOCATION: (13)..(13)
<223> OTHER INFORMATION: n is a, c, g, or t
```

<400> SEQUENCE: 50
wgtgnagwan canag                                                15

<210> SEQ ID NO 51
<211> LENGTH: 15
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t

<400> SEQUENCE: 51
sttntastnc tntgc                                                15

<210> SEQ ID NO 52
<211> LENGTH: 17
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (9)..(9)
<223> OTHER INFORMATION: n is a, c, g, or t

<400> SEQUENCE: 52
sstggstana twatwct                                              17

<210> SEQ ID NO 53
<211> LENGTH: 16
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (5)..(5)
<223> OTHER INFORMATION: n is a, c, g, or t
<220> FEATURE:
<221> NAME/KEY: misc_feature
<222> LOCATION: (10)..(10)
<223> OTHER INFORMATION: n is a, c, g, or t
<220> FEATURE:
<221> NAME/KEY: misc_feature
<222> LOCATION: (13)..(13)
<223> OTHER INFORMATION: n is a, c, g, or t

<400> SEQUENCE: 53
agwgnagwan canaga                                               16

<210> SEQ ID NO 54
<211> LENGTH: 1565
<212> TYPE: DNA
<213> ORGANISM: Hevea brasiliensis

<400> SEQUENCE: 54
ctctgcttcg cacgagtagc gttctaaatc taccaaggat gattacgaaa ggggaagcaa      60
tccttccagg aatcaaaaaa agggacatgc caatgaatgc tcgttttatt accctacaag    120

-continued

```
tacagtgcaa ggttgggtca gtgaatagag ttattggcac agccatgttt cctgtttcta      180
attcttggga ggttatacac aagtgaattt tgagttacag gctgagggat gaaaagaatg      240
gaattgttac actgtatttg gtagggagaa aagtaagaga ggaaagaaaa tataaagaaa      300
aaataagttt atttttatt gttttgttta aattgaataa aaaataaaga agcgtaaaaa       360
tattaaaagg aaaataaaaa tattttatct ttttttctt ttctctttaa aatagagaaa       420
aatgagagga aaatatttaa aagtataaat ataactctat atttaataat ttttttaaa      480 atttaaaaat aaaattataa ttttattatt cataaaataa ttttttctca aatatttttc     540
tctttcaatc cagataaaaa gaaaaaaaat aattttatt ttcattcttt attttctctc      600
ttttaatttt ctttctccct gaaatattcc caaacacagt gttaatgttt ttgtaaaaag     660
gggcaagcag tagcagatca cgtgagaaag aatttgccta tagtattgcc cgtgttcttc     720
ctcgtcatcg ttgttgcggc caacctaatt tatcatggag gagtagtgcc agggatttca     780
cgtttggcgt acttctggtg cttaattaat ttatttgggg ttttgtattt taaaattagg    840
taaaatttct ataattttac aaaaattaac ttattttatt aaaaattaaa agatttagac    900
taaatagcaa aatcacgcaa tgggtttagt gttttaatac gagattagac ataataataa    960
taacacctga tggtcctcta ttttcaatta tttgccaact aaaccacaat caaccatgtt   1020
caacacaatt ggaattctac tgatatatca ttacagctgc caaaacattt atttaggcca   1080
ttaatcaatt ttaattgaac atgctatttt tctatcatca attcagcttc tttttttata   1140
ttaatttaat ttataattaa cactaatgac aaaattagat attaaattta tgagaatgaa   1200
acataaaatt aatatataaa aaatatatta gttttaaaaa taattttaaa tattaaactc   1260
aaaatattat atatatatat atatatatat atatatgaaa ttaaaatttt aaattaaaaa   1320
aatgcagtaa aaaaaaaaaa aataataaag tagctattgg atccaagggt ggtttagaac   1380
gctactcgtg cgaagcaaga gtgaggaaaa tgccaaggac ccgtcacgca cgccacatgt    1440
gtggggagga ggctcccgtt ctcgcattct tataaaaatg tcccagatcc aaatctcctg    1500
aaactaagct catcattccc tcttcctcct ctccctttct ctctcctgcg ccggcatatt    1560
tttac                                                               1565
```